(12) United States Patent
Treu

(10) Patent No.: US 9,150,578 B2
(45) Date of Patent: *Oct. 6, 2015

(54) 5,8-DIHYDRO-6H-PYRAZOLO[3,4-H] QUINAZOLINES AS IGF-1R/IR INHIBITORS

(71) Applicant: Matthias Treu, Vienna (AT)

(72) Inventor: Matthias Treu, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 326 days.

This patent is subject to a terminal disclaimer.

(21) Appl. No.: 13/746,411

(22) Filed: Jan. 22, 2013

(65) Prior Publication Data

US 2013/0190305 A1  Jul. 25, 2013

(30) Foreign Application Priority Data

Jan. 23, 2012  (EP) .................................. 12152193

(51) Int. Cl.
*A61K 31/535* (2006.01)
*C07D 487/04* (2006.01)
*C07D 487/14* (2006.01)

(52) U.S. Cl.
CPC ............ *C07D 487/04* (2013.01); *C07D 487/14* (2013.01)

(58) Field of Classification Search
CPC ............................ C07D 487/04; C07D 487/14
USPC ........... 514/232.8, 252.16, 267; 544/115, 251
See application file for complete search history.

(56) References Cited

U.S. PATENT DOCUMENTS

2005/0148603 A1* 7/2005 Jimenez et al. ............ 514/260.1

FOREIGN PATENT DOCUMENTS

WO  2004104007 A1  12/2004
WO  2007134259 A2  11/2007

OTHER PUBLICATIONS

International Search Report, Form PCT/ISA/210, and Writen Opinion, Form PCT/ISA/237, for corresponding application PCT/EP/213/051097, date of mailing Mar. 26, 2013.

* cited by examiner

*Primary Examiner* — Jason Sims
*Assistant Examiner* — Ibrahim D Bori
(74) *Attorney, Agent, or Firm* — Michael P. Morris; Alan R. Stempel

(57) ABSTRACT

The present invention encompasses compounds of general formula (I)

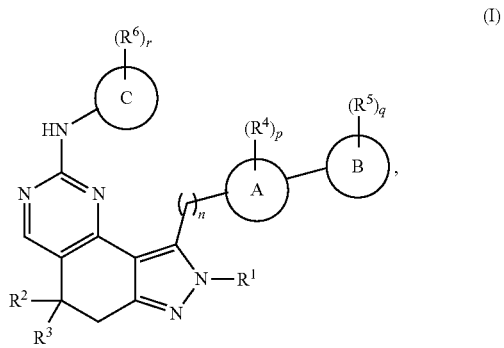

wherein the groups $R^1$ to $R^6$, A, B, C, n, p, q and r are defined as in claim 1, which are suitable for the treatment of diseases characterized by excessive or abnormal cell proliferation, pharmaceutical preparations which contain compounds of this kind and their use as medicaments.

30 Claims, No Drawings

5,8-DIHYDRO-6H-PYRAZOLO[3,4-H]QUINAZOLINES AS IGF-1R/IR INHIBITORS

The present invention relates to new 5,8-dihydro-6H-pyrazolo[3,4-h]quinazolines of general formula (I)

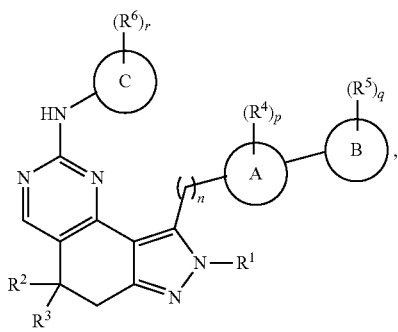

wherein the groups $R^1$ to $R^6$, A, B, C, n, p, q and r have the meanings given below in this specification, pharmaceutical preparations which contain compounds of this kind and their use as medicaments.

BACKGROUND TO THE INVENTION

WO 2005/037843 describes partially saturated quinazolines anellated with heteroaryls as kinase inhibitors.

WO 2012/010704 describes 5,8-dihydro-6H-pyrazolo[3,4-h]quinazolines as IGF-1R/IR inhibitors The aim of the present invention is to provide new compounds which can be used for the prevention and/or treatment of diseases characterised by excessive or abnormal cell proliferation. The compounds according to the invention are characterised by a powerful inhibitory effect on the phosphorylation activity of the IGF-1 receptor (IGF1-R) and insulin receptor (IR) located in cell membranes and a potent efficacy against tumour cells, e.g. glioblastoma, colorectal cancer etc., which is mediated through the inhibition of phosphorylation of the receptor. In addition to the inhibitory effect and cell activity the compounds have acceptable solubility, PK properties and selectivity over other kinases (Invitrogen panel).

The insulin-like growth factor (IGF) and insulin signalling network is a highly conserved and essential pathway involved in biological processes including growth, metabolism and homeostasis. In addition, deregulated signalling via this network can enhance tumorigenesis and metastasis of certain cancers.

The ligands IGF-1, IGF-2 and insulin are highly homologous and activate specific hetero or homodimers of the IGF-1R and IR. Following ligand binding, the IGF-1R and IR undergo autophosphorylation mediated via the receptor tyrosine kinase domains. The phosphorylated receptors activate the canonical Ras-Raf-MEK-ERK1/2 and PI3K-PDK1-Akt intracellular signaling cascades, which leads to cell proliferation and survival. In addition, activation of the IR by insulin stimulates the uptake of glucose and storage of glycogen in metabolic tissues such as the liver, adipose and muscle.

Published research articles as well as medical and epidemiological investigations have identified a strong correlation between expression of the IGF-1R and IR and ligands for these receptors in tumor development and progression. Developing a small molecule competitive inhibitor of the ATP-binding pocket of the IGF-1R and IR as a means of blocking growth and survival signaling cascades in cancer is therefore desirable. The anticipated clinical benefit of blocking such an interaction would be to reduce tumor growth rate and potentially sensitize tumors to cytotoxic agents or targeted therapies.

DETAILED DESCRIPTION OF THE INVENTION

It has now been found that, surprisingly, compounds of general formula (I) wherein the groups $R^1$ to $R^6$, A, B, C, n, p, q and r have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to a compound of general formula (I)

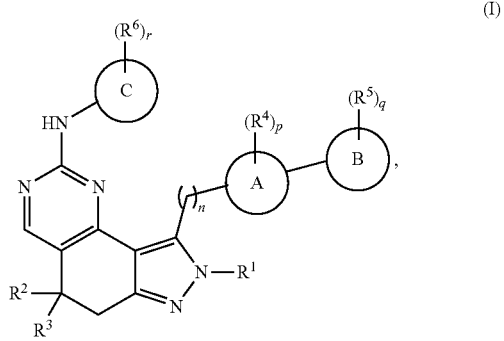

wherein

[A0]

$R^1$ denotes $C_{1-4}$alkyl;

[B0]

$R^2$ denotes hydrogen or $C_{1-4}$alkyl;

$R^3$ denotes hydrogen or $C_{1-4}$alkyl;

[C0]

n denotes 0 or 1;

[D0]

ring A is phenyl or 5-6 membered heteroaryl;

each $R^4$ is independently of one another selected from among halogen, $C_{1-4}$alkoxy, $C_{1-4}$alkyl and —CN;

p denotes 0, 1 or 2;

[E0]

ring B is a 5-membered heteroaryl;

each $R^5$ independently is $R^{b1}$ or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{d1}$ is independently selected from among —$OR^{e1}$, —$NR^{e1}R^{e1}$, halogen, —CN, —C(O)$R^{e1}$, —C(O)O$R^{e1}$, —C(O)N$R^{e1}R^{e1}$, —S(O)$_2R^{e1}$, —S(O)$_2$N$R^{e1}R^{e1}$, —NHC(O)$R^{e1}$ and —N(C$_{1-4}$alkyl)C(O)$R^{e1}$, each $R^{e1}$ independently of one another denotes hydrogen or a group, optionally substituted by one or more, identical or different $R^{f1}$ and/or $R^{g1}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{f1}$ is independently selected from among —$OR^{g1}$, —$NR^{g1}R^{g1}$, halogen, —CN, —C(O)$R^{g1}$, —C(O)O$R^{g1}$, —C(O)N$R^{g1}R^{g1}$, —S(O)$_2R^{g1}$, —S(O)$_2$N$R^{g1}R^{g1}$, —NHC(O)$R^{g1}$ and —N(C$_{1-4}$alkyl)C(O)$R^{g1}$;

each $R^{g1}$ independently of one another denotes hydrogen or C$_{1-6}$alkyl;

q denotes 0, 1 or 2;

[F0]
ring C is phenyl or 5-6 membered heteroaryl;

each $R^6$ independently is $R^{b2}$ or a group, optionally substituted by one or more, identical or different $R^{b2}$ and/or $R^{c2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$ and —N(C$_{1-4}$alkyl)C(O)$R^{c2}$;

each $R^{c2}$ independently of one another denotes hydrogen or a group, optionally substituted by one or more, identical or different $R^{d2}$ and/or $R^{e2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2$N$R^{e2}R^{e2}$, —NHC(O)$R^{e2}$ and —N(C$_{1-4}$alkyl)C(O)$R^{e2}$;

each $R^{e2}$ independently of one another denotes hydrogen or a group, optionally substituted by one or more, identical or different $R^{f2}$ and/or $R^{g2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2$N$R^{g2}R^{g2}$, —NHC(O)$R^{g2}$ and —N(C$_{1-4}$alkyl)C(O)$R^{g2}$;

each $R^{g2}$ independently of one another denotes hydrogen or C$_{1-6}$alkyl;

r denotes 0, 1 or 2;

wherein the compound (I) may optionally also be present in the form of the tautomers, racemates, enantiomers, diastereomers and the mixtures thereof or as the respective salt of all the above-mentioned forms.

In one aspect [A1] the invention relates to a compound (I), wherein $R^1$ is methyl.

In another aspect [B1] the invention relates to a compound (I), wherein $R^2$ and $R^3$ both denote hydrogen.

In another aspect [B2] the invention relates to a compound (I), wherein $R^2$ is hydrogen and $R^3$ is C$_{1-4}$alkyl.

In another aspect [B3] the invention relates to a compound (I), wherein $R^2$ is hydrogen and $R^3$ is methyl.

In another aspect [D1] the invention relates to a compound (I), wherein ring A is phenyl or pyridyl;

each $R^4$ is independently of one another selected from among halogen, C$_{1-4}$alkoxy, C$_{1-4}$alkyl and —CN;

p denotes 0, 1 or 2.

In another aspect [D2] the invention relates to a compound (I), wherein ring A is phenyl or pyridyl;

p is 0.

In another aspect [F1] the invention relates to a compound (I), wherein ring C is phenyl;

each $R^6$ independently is $R^{b2}$ or a group, optionally substituted by one or more, identical or different $R^{b2}$ and/or $R^{c2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$ and —N(C$_{1-4}$alkyl)C(O)$R^{c2}$;

each $R^{c2}$ independently of one another denotes hydrogen or a group, optionally substituted by one or more, identical or different $R^{d2}$ and/or $R^{e2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2$N$R^{e2}R^{e2}$, —NHC(O)$R^{e2}$ and —N(C$_{1-4}$alkyl)C(O)$R^{e2}$;

each $R^{e2}$ independently of one another denotes hydrogen or a group, optionally substituted by one or more, identical or different $R^{f2}$ and/or $R^{g2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2$N$R^{g2}R^{g2}$, —NHC(O)$R^{g2}$ and —N(C$_{1-4}$alkyl)C(O)$R^{g2}$;

each $R^{g2}$ independently of one another denotes hydrogen or C$_{1-6}$alkyl;

r denotes 0, 1 or 2.

In another aspect [F2] the invention relates to a compound (I), wherein ring C is phenyl;

each $R^6$ independently is $R^{b2}$ or a group, optionally substituted by one or more, identical or different $R^{b2}$ and/or $R^{c2}$, selected from among C$_{1-6}$alkyl, C$_{3-6}$cycloalkyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$ and —N(C$_{1-4}$alkyl)C(O)$R^{c2}$;

each $R^{c2}$ independently of one another denotes hydrogen or a group, optionally substituted by one or more, identical or different $R^{d2}$ and/or $R^{e2}$, selected from among C$_{1-6}$alkyl, C$_{3-6}$cycloalkyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2$N$R^{e2}R^{e2}$, —NHC(O)$R^{e2}$ and —N(C$_{1-4}$alkyl)C(O)$R^{e2}$;

each $R^{e2}$ independently of one another denotes hydrogen or a group, optionally substituted by one or more, identical or different $R^{f2}$ and/or $R^{g2}$, selected from among C$_{1-6}$alkyl, C$_{3-6}$cycloalkyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2$N$R^{g2}R^{g2}$, —NHC(O)$R^{g2}$ and —N(C$_{1-4}$alkyl)C(O)$R^{g2}$;

each $R^{g2}$ independently of one another denotes hydrogen or C$_{1-6}$alkyl;

r denotes 0, 1 or 2.

In another aspect [F3] the invention relates to a compound (I), wherein ring C is phenyl;

each $R^6$ independently is $R^{b2}$ or 3-7 membered heterocyclyl, the heterocyclyl optionally substituted by one or more, identical or different $R^{b2}$ and/or $R^{c2}$;

each $R^{b2}$ is independently selected from among —$OR^{c2}$, —$C(O)R^{c2}$, —$C(O)OR^{c2}$, —$C(O)NR^{c2}R^{c2}$ and —$S(O)_2NR^{c2}R^{c2}$;

each $R^{c2}$ independently of one another denotes hydrogen or a group, optionally substituted by one or more, identical or different $R^{d2}$ and/or $R^{e2}$, selected from among $C_{1-6}$alkyl and 3-7 membered heterocyclyl;

each $R^{d2}$ is independently selected from among —$OR^{e2}$ and —$NR^{e2}R^{e2}$;

each $R^{e2}$ independently of one another denotes hydrogen or a group, optionally substituted by one or more, identical or different $R^{f2}$ and/or $R^{g2}$, selected from among $C_{1-6}$alkyl and 3-7 membered heterocyclyl;

each $R^{f2}$ is —$OR^{g2}$;

each $R^{g2}$ independently of one another denotes hydrogen or $C_{1-6}$alkyl;

r denotes 0, 1 or 2.

In another aspect [F4] the invention relates to a compound (I), wherein ring C is phenyl;

each $R^6$ independently is —$C(O)NR^{c2}R^{c2}$, —$C(O)R^{c2}$ or —$OR^{c2}$;

each $R^{c2}$ independently of one another denotes hydrogen or a group, optionally substituted by one or more, identical or different $R^{d2}$ and/or $R^{e2}$, selected from among $C_{1-6}$alkyl and 3-7 membered heterocyclyl;

each $R^{d2}$ is independently selected from among —$OR^{e2}$ and —$NR^{e2}R^{e2}$;

each $R^{e2}$ independently of one another denotes hydrogen or a group, optionally substituted by one or more, identical or different $R^{f2}$ and/or $R^{g2}$, selected from among $C_{1-6}$alkyl and 3-7 membered heterocyclyl;

each $R^{f2}$ is —$OR^{g2}$;

each $R^{g2}$ independently of one another denotes hydrogen or $C_{1-6}$alkyl;

r denotes 0, 1 or 2.

In further aspects [F5][F6][F7][F8] the invention relates to a compound (I) with structural aspects [F1][F2][F3][F4], wherein r is 2.

In another aspect [F9] the invention relates to a compound (I), wherein ring C is 5-6 membered heteroaryl;

each $R^6$ independently is $R^{b2}$ or a group, optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;

each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;

each $R^{e2}$ independently of one another denotes hydrogen or a group, optionally substituted by one or more, identical or different $R^{f2}$ and/or $R^{g2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;

each $R^{g2}$ independently of one another denotes hydrogen or $C_{1-6}$alkyl;

r denotes 0, 1 or 2.

In another aspect [F10] the invention relates to a compound (I), wherein ring C is 5-6 membered heteroaryl;

each $R^6$ independently is $R^{b2}$ or a group, optionally substituted by one or more, identical or different $R^{b2}$ and/or $R^{c2}$, selected from among $C_{1-6}$alkyl, $C_{3-6}$cycloalkyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^2$;

each $R^{c2}$ independently of one another denotes hydrogen or a group, optionally substituted by one or more, identical or different $R^{d2}$ and/or $R^{e2}$, selected from among $C_{1-6}$alkyl, $C_{3-6}$cycloalkyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;

each $R^{e2}$ independently of one another denotes hydrogen or a group, optionally substituted by one or more, identical or different $R^{f2}$ and/or $R^{g2}$, selected from among $C_{1-6}$alkyl, $C_{3-6}$cycloalkyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;

each $R^{g2}$ independently of one another denotes hydrogen or $C_{1-6}$alkyl;

r denotes 0, 1 or 2.

In another aspect [F11] the invention relates to a compound (I), wherein ring C is pyrazolyl;

each $R^6$ independently is $R^{b2}$ or a group, optionally substituted by one or more, identical or different $R^{b2}$ and/or $R^{c2}$, selected from among $C_{1-6}$alkyl, $C_{3-6}$cycloalkyl, phenyl, 5-6 membered heteroaryl and 3-7 membered heterocyclyl;

each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;

each $R^{c2}$ independently of one another denotes hydrogen or a group, optionally substituted by one or more, identical or different $R^{d2}$ and/or $R^{e2}$, selected from among $C_{1-6}$alkyl, $C_{3-6}$cycloalkyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;

each $R^{e2}$ independently of one another denotes hydrogen or a group, optionally substituted by one or more, identical or different $R^{f2}$ and/or $R^{g2}$, selected from among $C_{1-6}$alkyl, $C_{3-6}$cycloalkyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2NR^{g2}R^{g2}$, —NHC(O)$R^{g2}$ and —N($C_{1-4}$alkyl)C(O)$R^{g2}$;

each $R^{g2}$ independently of one another denotes hydrogen or $C_{1-6}$alkyl;

r denotes 0, 1 or 2.

In another aspect [F12] the invention relates to a compound (I), wherein ring C is pyrazolyl;

each $R^6$ independently is a group, optionally substituted by one or more, identical or different $R^{b2}$ and/or $R^{c2}$, selected from among $C_{1-6}$alkyl and 3-7 membered heterocyclyl;

each $R^{b2}$ is independently selected from among —$OR^{c2}$, —$NR^{c2}R^{c2}$, —C(O)$R^{c2}$, —C(O)O$R^{c2}$, —C(O)N$R^{c2}R^{c2}$, —S(O)$_2R^{c2}$ and —S(O)$_2NR^{c2}R^{c2}$;

each $R^{c2}$ independently of one another denotes hydrogen or a group, optionally substituted by one or more, identical or different $R^{d2}$ and/or $R^{e2}$, selected from among $C_{1-6}$alkyl, 5-6 membered heteroaryl and 3-7 membered heterocyclyl;

each $R^{d2}$ is independently selected from among —$OR^{e2}$ and —$NR^{e2}R^{e2}$;

each $R^{e2}$ independently of one another denotes hydrogen or $C_{1-6}$alkyl optionally substituted by one or more, identical or different $R^{f2}$ and/or $R^{g2}$;

each $R^{f2}$ is —$OR^{g2}$;

each $R^{g2}$ independently of one another denotes hydrogen or $C_{1-6}$alkyl;

r denotes 0, 1 or 2.

In further aspects [F13][F14][F15][F16] the invention relates to a compound (I) with structural aspects [F9][F10][F11][F12], wherein r is 1.

In another aspect [F17] the invention relates to a compound (I), wherein r is 1 and ring C and $R^6$ altogether is

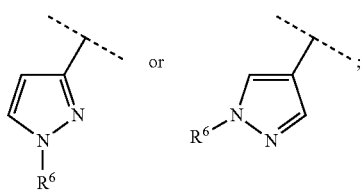

$R^6$ independently is a group, optionally substituted by one or more, identical or different $R^{b2}$ and/or $R^{c2}$, selected from among $C_{1-6}$alkyl and 3-7 membered heterocyclyl;

each $R^{b2}$ is independently selected from among —$OR^{c2}$, —$NR^{c2}R^{c2}$, —C(O)$R^{c2}$, —C(O)O$R^{c2}$, —C(O)N$R^{c2}R^{c2}$, —S(O)$_2R^{c2}$ and —S(O)$_2NR^{c2}R^{c2}$;

each $R^{c2}$ independently of one another denotes hydrogen or a group, optionally substituted by one or more, identical or different $R^{d2}$ and/or $R^{e2}$, selected from among $C_{1-6}$alkyl, 5-6 membered heteroaryl and 3-7 membered heterocyclyl;

each $R^{d2}$ is independently selected from among —$OR^{e2}$ and —$NR^{e2}R^{e2}$;

each $R^{e2}$ independently of one another denotes hydrogen or $C_{1-6}$alkyl optionally substituted by one or more, identical or different $R^{f2}$ and/or $R^{g2}$;

each $R^{f2}$ is —$OR^{g2}$;

each $R^{g2}$ independently of one another denotes hydrogen or $C_{1-6}$alkyl.

In another aspect [F18] the invention relates to a compound (I), wherein r is 1 and ring C and $R^6$ altogether is

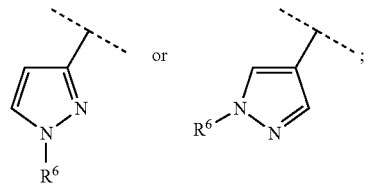

$R^6$ independently is selected from among $C_{1-4}$alkyl, hydroxy-$C_{2-4}$alkyl, $C_{1-4}$alkoxy-$C_{2-4}$alkyl and $(C_{1-4}$alkyl)$_2$N—$C_{2-4}$alkyl.

In another aspect [F19] the invention relates to a compound (I), wherein r is 1 and ring C and $R^6$ altogether is selected from among

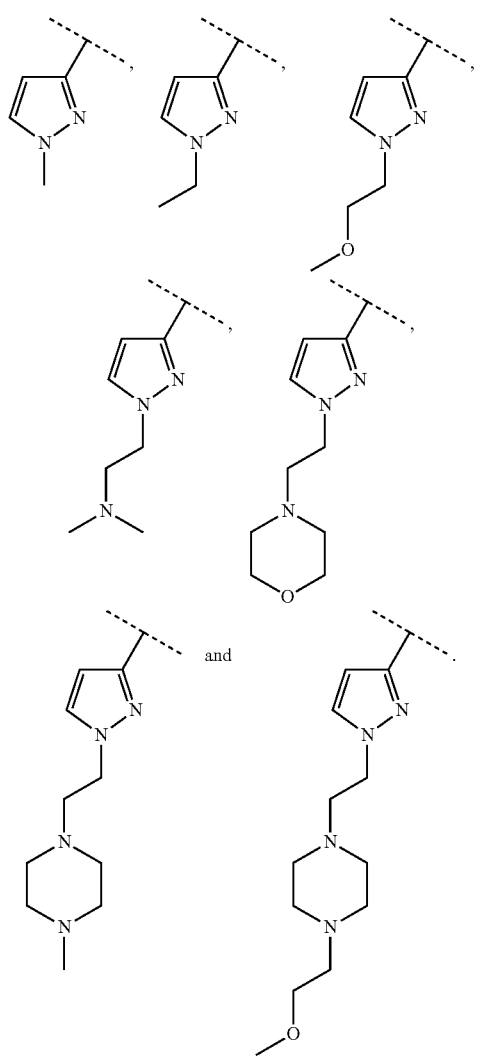

In another aspect [E1] the invention relates to a compound (I), wherein ring B is a 5-membered heteroaryl;

each $R^5$ independently is $R^{b1}$ or a group, optionally substituted by one or more, identical or different $R^{b1}$ and/or $R^{c1}$, selected from among $C_{1-6}$alkyl, $C_{3-6}$cycloalkyl, phenyl, 5-6 membered heteroaryl and 3-7 membered heterocyclyl;

- each $R^{b1}$ is independently selected from among $-OR^{c1}$, $-NR^{c1}R^{c1}$, halogen, $-CN$, $-C(O)R^{c1}$, $-C(O)OR^{c1}$, $-C(O)NR^{c1}R^{c1}$, $-S(O)_2R^{c1}$, $-S(O)_2NR^{c1}R^{c1}$, $-NHC(O)R^{c1}$ and $-N(C_{1-4}$alkyl$)C(O)R^{c1}$;
- each $R^{c1}$ independently of one another denotes hydrogen or a group, optionally substituted by one or more, identical or different $R^{d1}$ and/or $R^{e1}$, selected from among $C_{1-6}$alkyl, $C_{3-6}$cycloalkyl, phenyl, 5-6 membered heteroaryl and 3-7 membered heterocyclyl;
- each $R^{d1}$ is independently selected from among $-OR^{e1}$, $-NR^{e1}R^{e1}$, halogen, $-CN$, $-C(O)R^{e1}$, $-C(O)OR^{e1}$, $-C(O)NR^{e1}R^{e1}$, $-S(O)_2R^{e1}$, $-S(O)_2NR^{e1}R^{e1}$, $-NHC(O)R^{e1}$ and $-N(C_{1-4}$alkyl$)C(O)R^{e1}$,
- each $R^{e1}$ independently of one another denotes hydrogen or a group, optionally substituted by one or more, identical or different $R^{f1}$ and/or $R^{g1}$, selected from among $C_{1-6}$alkyl, $C_{3-6}$cycloalkyl, phenyl, 5-6 membered heteroaryl and 3-7 membered heterocyclyl;
- each $R^{f1}$ is independently selected from among $-OR^{g1}$, $-NR^{g1}R^{g1}$, halogen, $-CN$, $-C(O)R^{g1}$, $-C(O)OR^{g1}$, $-C(O)NR^{g1}R^{g1}$, $-S(O)_2R^{g1}$, $-S(O)_2NR^{g1}R^{g1}$, $-NHC(O)R^{g1}$ and $-N(C_{1-4}$alkyl$)C(O)R^{g1}$;
- each $R^{g1}$ independently of one another denotes hydrogen or $C_{1-6}$alkyl;
- q denotes 0, 1 or 2.

In another aspect [E2] the invention relates to a compound (I), wherein ring B is pyrazolyl;

each $R^5$ independently is $R^{b1}$ or a group, optionally substituted by one or more, identical or different $R^{b1}$ and/or $R^{c1}$, selected from among $C_{1-6}$alkyl, $C_{3-6}$cycloalkyl, phenyl, 5-6 membered heteroaryl and 3-7 membered heterocyclyl;

- each $R^{b1}$ is independently selected from among $-OR^{c1}$, $-NR^{c1}R^{c1}$, halogen, $-CN$, $-C(O)R^{c1}$, $-C(O)OR^{c1}$, $-C(O)NR^{c1}R^{c1}$, $-S(O)_2R^{c1}$, $-S(O)_2NR^{c1}R^{c1}$, $-NHC(O)R^{c1}$ and $-N(C_{1-4}$alkyl$)C(O)R^{c1}$;
- each $R^{c1}$ independently of one another denotes hydrogen or a group, optionally substituted by one or more, identical or different $R^{d1}$ and/or $R^{e1}$, selected from among $C_{1-6}$alkyl, $C_{3-6}$cycloalkyl, phenyl, 5-6 membered heteroaryl and 3-7 membered heterocyclyl;
- each $R^{d1}$ is independently selected from among $-OR^{e1}$, $-NR^{e1}R^{e1}$, halogen, $-CN$, $-C(O)R^{e1}$, $-C(O)OR^{e1}$, $-C(O)NR^{e1}R^{e1}$, $-S(O)_2R^{e1}$, $-S(O)_2NR^{e1}R^{e1}$, $-NHC(O)R^{e1}$ and $-N(C_{1-4}$alkyl$)C(O)R^{e1}$;
- each $R^{e1}$ independently of one another denotes hydrogen or a group, optionally substituted by one or more, identical or different $R^{f1}$ and/or $R^{g1}$, selected from among $C_{1-6}$alkyl, $C_{3-6}$cycloalkyl, phenyl, 5-6 membered heteroaryl and 3-7 membered heterocyclyl;
- each $R^{f1}$ is independently selected from among $-OR^{g1}$, $-NR^{g1}R^{g1}$, halogen, $-CN$, $-C(O)R^{g1}$, $-C(O)OR^{g1}$, $-C(O)NR^{g1}R^{g1}$, $-S(O)_2R^{g1}$, $-S(O)_2NR^{g1}R^{g1}$, $-NHC(O)R^{g1}$ and $-N(C_{1-4}$alkyl$)C(O)R^{g1}$;
- each $R^{g1}$ independently of one another denotes hydrogen or $C_{1-6}$alkyl;
- q denotes 0, 1 or 2.

In another aspect [E3] the invention relates to a compound (I), wherein ring B is pyrazolyl;

each $R^5$ independently is a group, optionally substituted by one or more, identical or different $R^{b1}$ and/or $R^{c1}$, selected from among $C_{1-6}$alkyl and 3-7 membered heterocyclyl;

- each $R^{b1}$ is independently selected from among $-OR^{c1}$, $NR^{c1}R^{c1}$, halogen, $-C(O)OR^{c1}$ and $-C(O)NR^{c1}R^{c1}$;
- each $R^{c1}$ independently of one another denotes hydrogen or a group, optionally substituted by one or more, identical or different $R^{d1}$ and/or $R^{e1}$, selected from among $C_{1-6}$alkyl, phenyl and 3-7 membered heterocyclyl;
- each $R^{d1}$ is independently selected from among $-OR^{e1}$ and $-NR^{e1}R^{e1}$;
- each $R^{e1}$ independently of one another denotes hydrogen or $C_{1-6}$alkyl optionally substituted by one or more, identical or different $R^{f1}$ and/or $R^{g1}$;
- each $R^{f1}$ is $-OR^{g1}$;
- each $R^{g1}$ independently of one another denotes hydrogen or $C_{1-6}$alkyl;
- q denotes 0, 1 or 2.

In further aspects [E4][E5][E6] the invention relates to a compound (I) with structural aspects [E1][E2][E3], wherein q is 1.

In another aspect [E7] the invention relates to a compound (I), wherein q is 1 and ring B and $R^5$ altogether is

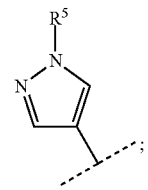

$R^5$ is a group, optionally substituted by one or more, identical or different $R^{b1}$ and/or $R^{c1}$, selected from among $C_{1-6}$alkyl and 3-7 membered heterocyclyl;

- each $R^{b1}$ is independently selected from among $-OR^{c1}$, $-NR^{c1}R^{c1}$, halogen, $-C(O)OR^{c1}$ and $-C(O)NR^{c1}R^{c1}$;
- each $R^{c1}$ independently of one another denotes hydrogen or a group, optionally substituted by one or more, identical or different $R^{d1}$ and/or $R^{e1}$, selected from among $C_{1-6}$alkyl, phenyl and 3-7 membered heterocyclyl;
- each $R^{d1}$ is independently selected from among $-OR^{e1}$ and $-NR^{e1}R^{e1}$,
- each $R^{e1}$ independently of one another denotes hydrogen or $C_{1-6}$alkyl optionally substituted by one or more, identical or different $R^{f1}$ and/or $R^{g1}$;
- each $R^{f1}$ is $-OR^{g1}$;
- each $R^{g1}$ independently of one another denotes hydrogen or $C_{1-6}$alkyl;

In another aspect [E8] the invention relates to a compound (I), wherein q is 1 and ring B and $R^5$ altogether is

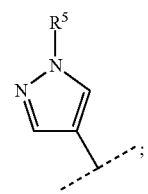

$R^5$ independently is selected from among $C_{1-4}$alkyl, hydroxy-$C_{2-4}$alkyl, $C_{1-4}$alkoxy-$C_{2-4}$alkyl and $(C_{1-4}$alkyl$)_2$N—$C_{2-4}$alkyl.

In another aspect [E9] the invention relates to a compound (I), wherein
q is 1 and ring B and R⁵ altogether is selected from among

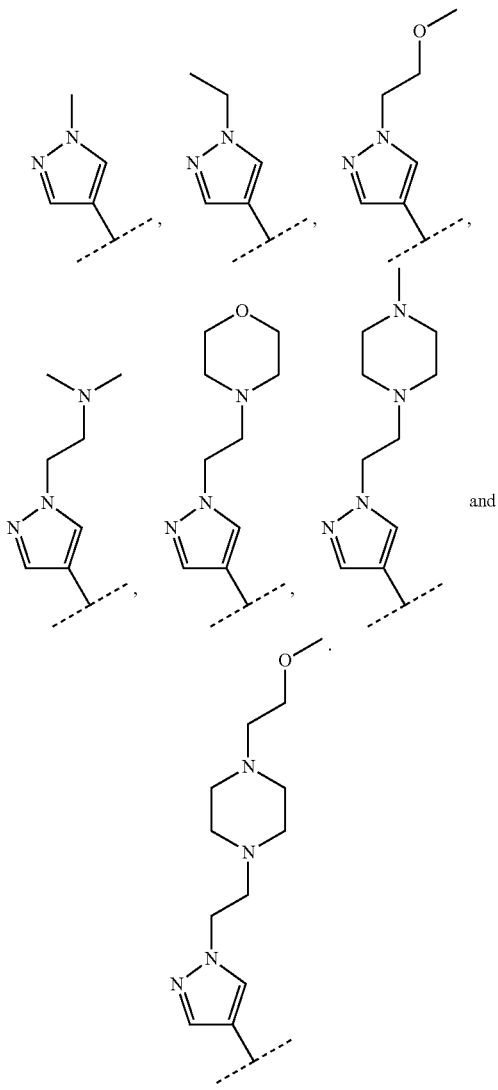

All the above-mentioned structural aspects A1, B1 to B3, D1 and D2, E1 to E9 and F1 to F19 are preferred embodiments of the various aspects A0, B0, D0, E0 and F0, respectively. The structural aspects A0 and A1, B0 to B3, C0, D0 to D2, E0 to E9 and F0 to F19 relating to different molecular parts of the compounds (I) according to the invention may be permutated with one another as desired in combinations ABCDEF, so as to obtain preferred compounds (I). Each combination ABCDEF represents and defines individual embodiments or generic amounts of compounds according to the invention.

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to the use of compounds of general formula (I)—or the pharmaceutically acceptable salts thereof—for preparing a pharmaceutical composition for the treatment and/or prevention of cancer, infections, inflammations and autoimmune diseases.

In another aspect the invention relates to compounds of general formula (I)—or the pharmaceutically acceptable salts thereof—for use in the treatment and/or prevention of cancer.

In another aspect the invention relates to the use of compounds of general formula (I)—or the pharmaceutically acceptable salts thereof—for preparing a pharmaceutical composition for the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of hepatocellular carcinomas (HCC), non-small cell lung cancer (NSCLC), breast cancer and prostate cancer.

In another aspect the invention relates to the use of compounds of general formula (I)—or the pharmaceutically acceptable salts thereof—for preparing a pharmaceutical composition for the treatment and/or prevention of hepatocellular carcinomas (HCC), non-small cell lung cancer (NSCLC), breast cancer and prostate cancer.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise:

The use of the prefix $C_{x\text{-}y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (cycloalkylalkyl, arylalkyl) relates to the total number of carbon atoms of all the carbon ring and carbon chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH$$(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH$$(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x\text{-}y}$alkenyleneamino or $H_2N$—$C_{x\text{-}y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x\text{-}y}$alkynylamino or $C_{x\text{-}y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x\text{-}y}$alkynyleneamino or $H_2N$—$C_{x\text{-}y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF{=}CF_2$, —$CCl{=}CH_2$, —$CBr{=}CH_2$, —$C{\equiv}C$—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x\text{-}y}$cycloalkylamino, $C_{x\text{-}y}$cycloalkyloxy or $C_{x\text{-}y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl.

Corresponding groups are for example:
cyclohexyl and

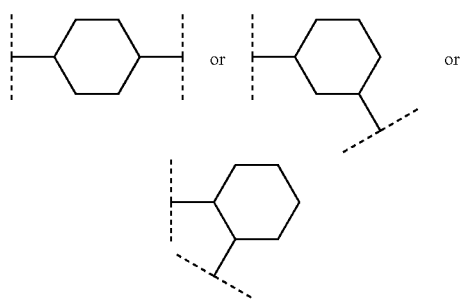

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners.

Formally, the second valency is obtained by removing a hydrogen atom from a cycloalkenyl. Corresponding groups are for example:
cyclopentenyl and

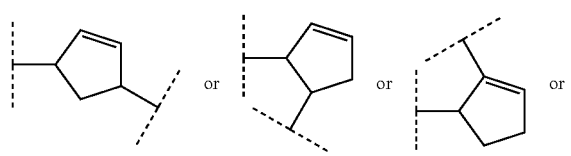

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:
phenyl and (o, m, p-phenylene),
naphthyl and

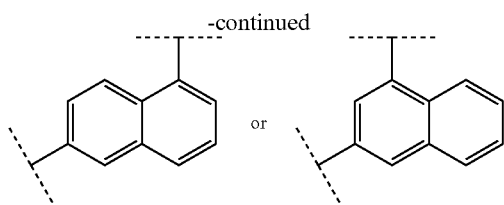

etc.

The above definition for arylene also applies if arylene is part of another (combined) group as for example in HO-aryleneamino or H₂N-aryleneoxy.

Heterocyclyl denotes ring systems, which are derived from the previously defined cycloalkyl, cycloalkenyl and aryl by replacing one or more of the groups —CH₂-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO₂—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-5,5-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-5-oxide, tetrahydrothienyl-S,S-dioxide, homothiomorpholinyl-5-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1] octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

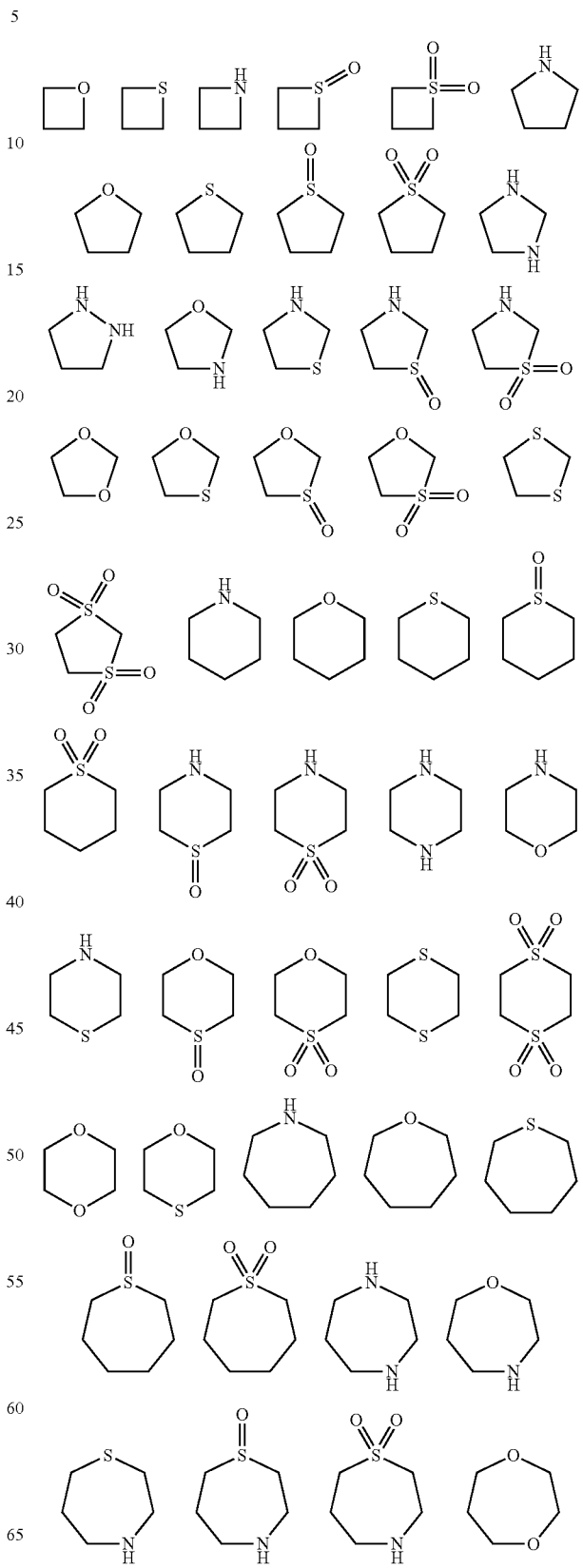

21
-continued
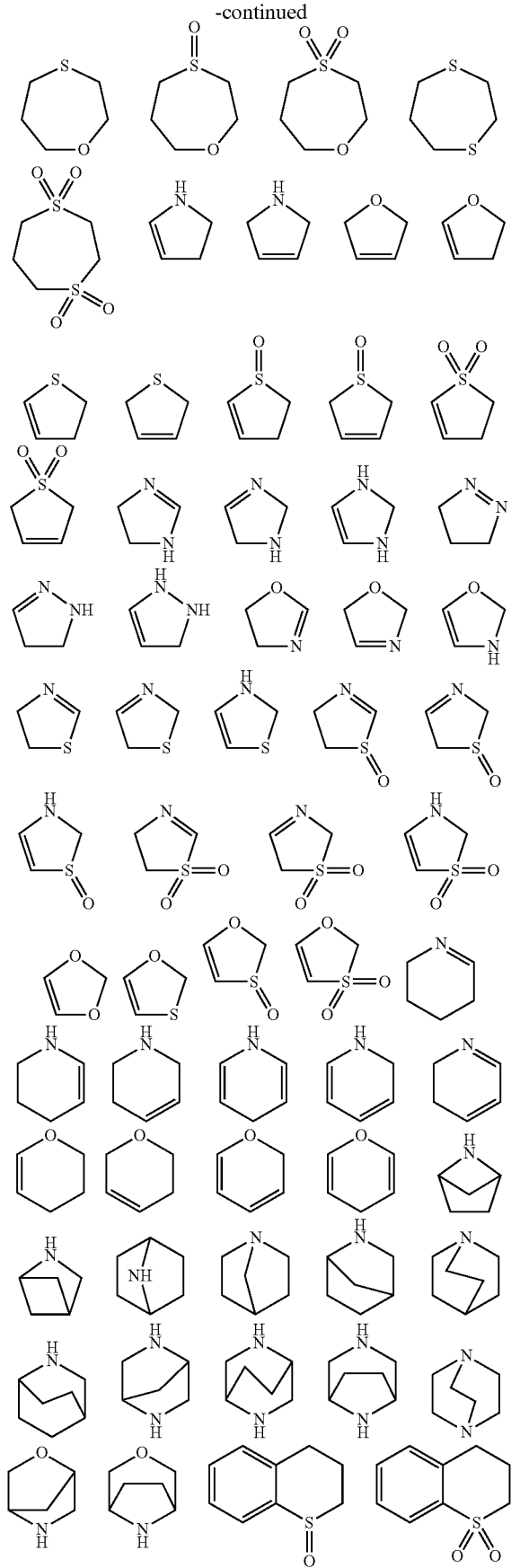
22
-continued
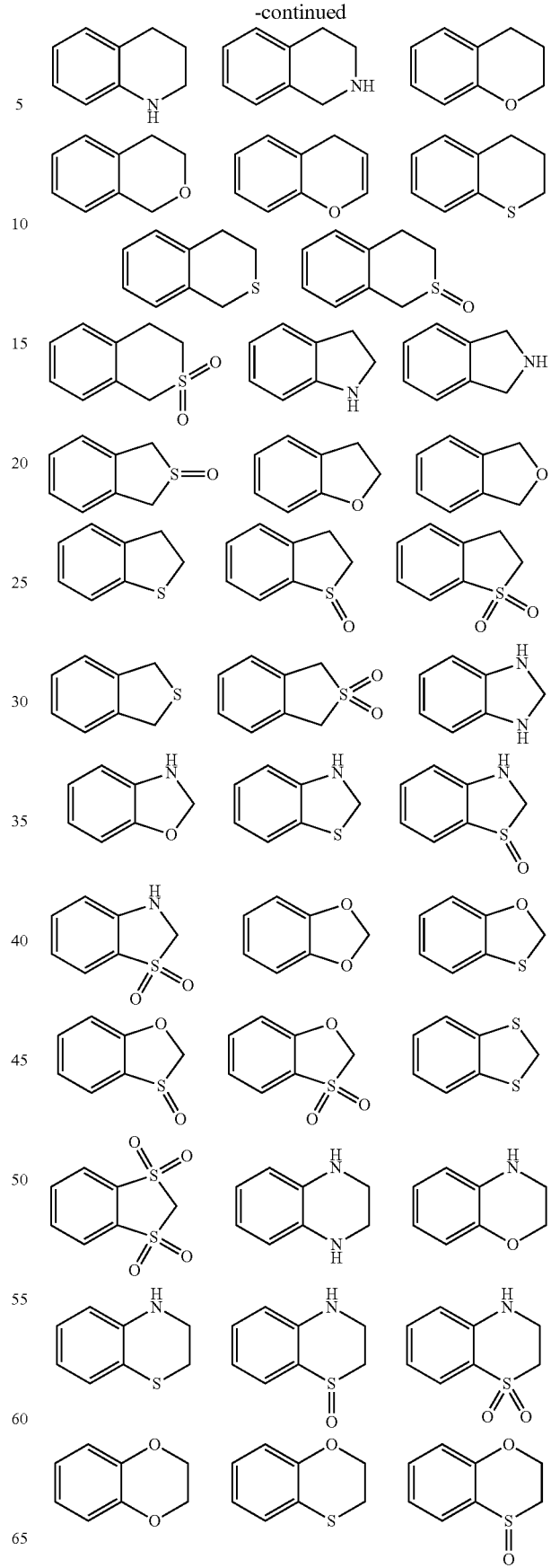

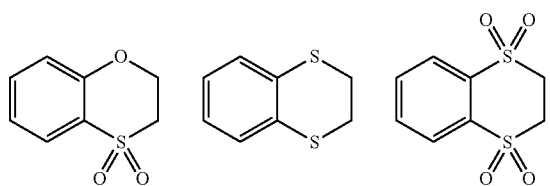

Preferred heterocyclyls in compounds (I) are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

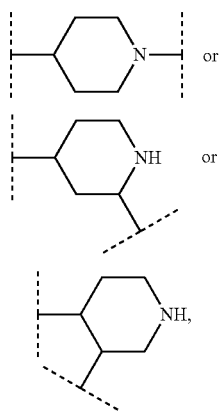

2,3-dihydro-1H-pyrrolyl and

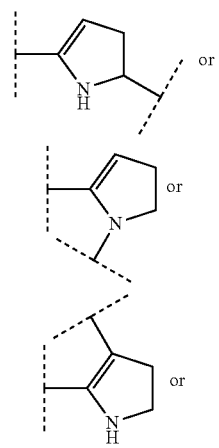

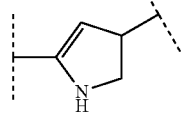

etc.

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

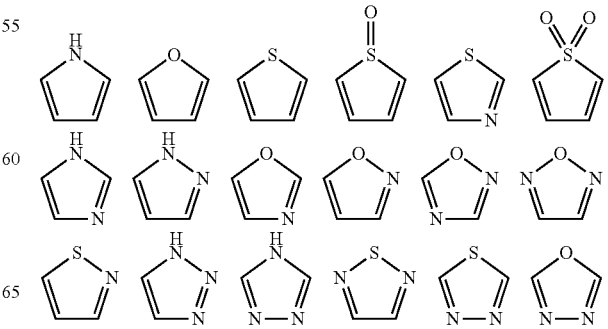

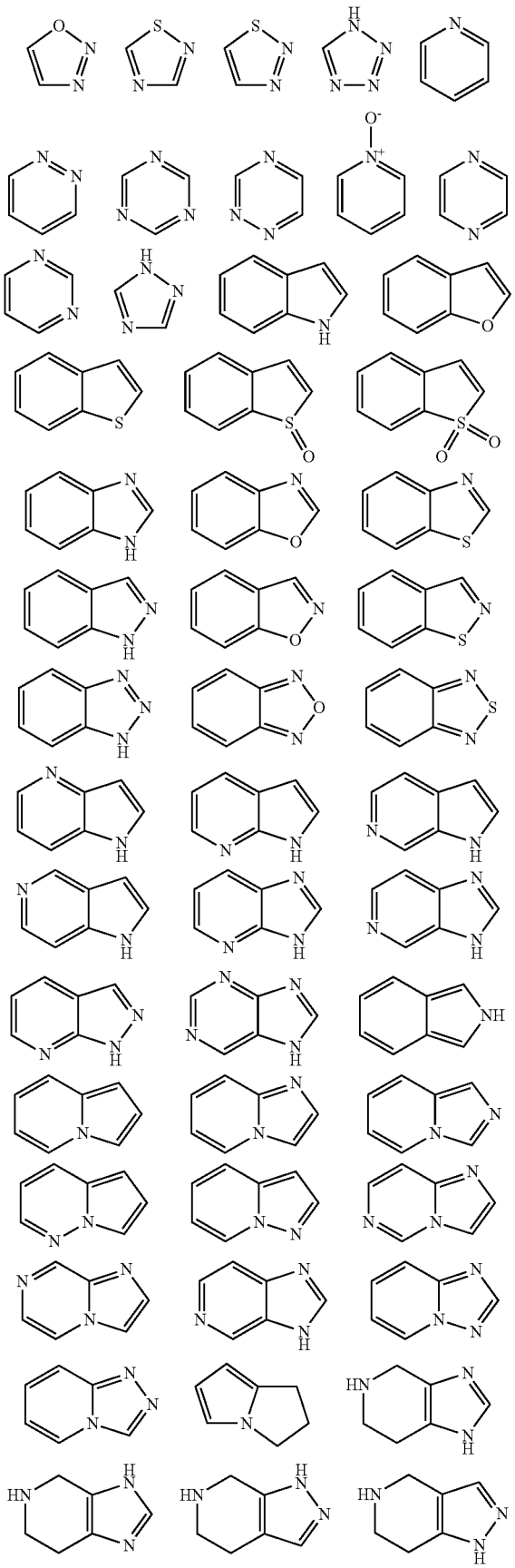

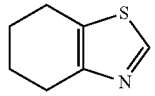

Preferred heteroaryls in compounds (I) are: pyridinyl, pyrimidyl, pyrazolyl, oxazolyl.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

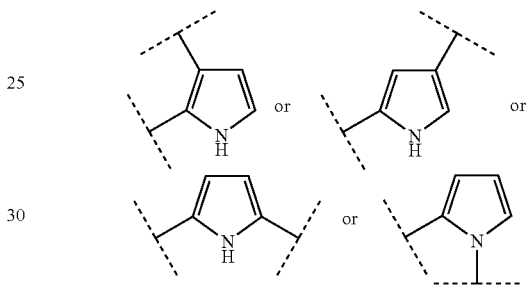

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

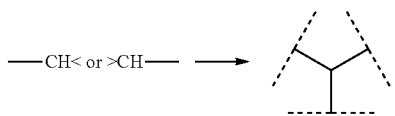

-continued

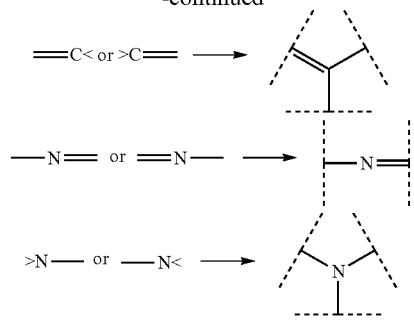

If for example in the sequence X—Y—Z the component Y is supposed to correspond to the structural section —N═, this means both X═N—Z and also X—N═Z.

In a representation such as for example

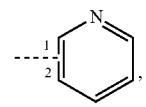

the dotted line means that the ring system may be attached to the molecule via the carbon atom 1 or 2, and is thus equivalent to the following representation

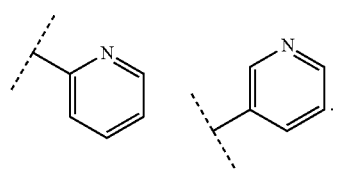

In a representation such as for example

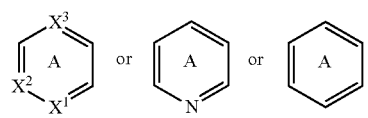

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

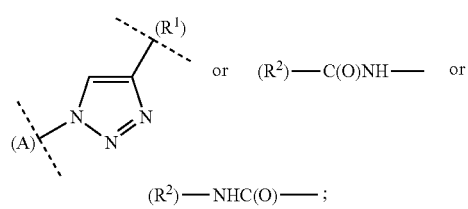

Groups or substituents are frequently selected from among a number of alternative groups/substituents with a corresponding group designation (e.g. $R^a$, $R^b$ etc). If such a group is used repeatedly to define a compound according to the invention in different parts of the molecule, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| Ac | acetyl |
| AcCN | acetonitrile |
| aq. | aquatic, aqueous |
| ATP | adenosine triphosphate |
| BiPh | biphenyl |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| Et$_2$O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| Kat., kat. | catalyst, catalytic |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf (R$_f$) | retention factor |
| RP | reversed phase |
| rt | ambient temperature |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| t$_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the fundamentals of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out with columns made by Waters (names: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm) or X-Bridge Prep C18 10 µm OBD 50×150 mm), Agilent (name: Zorbax SB-C8 5 µm PrepHT 21.2×50 mm) and Phenomenex (names: Gemini C18 5 µm AXIA 21.2×50 mm or Gemini C18 10 µm 50×150 mm). Different gradients of H$_2$O/acetonitrile or H$_2$O/MeOH are used to elute the compounds, while 0.1% HCOOH is added to the water (acidic conditions). For the chromatography under basic conditions H$_2$O/acetonitrile gradients are used as well, while the water is made alkaline as follows: 5 mL NH$_4$HCO$_3$ solution (158 g in 1 L H$_2$O) and 2 mL NH$_3$ (7 M in MeOH) are replenished to 1 L with H$_2$O.

The analytical HPLC (reaction control) of intermediate compounds is carried out using columns made by Agilent (names: Zorbax SB-C8, 5 µm, 21.2×50 mm or Zorbax SB-C8 3.5 µm 2.1×50 mm), Phenomenex (name: Gemini C18 3 µm 2×30 mm) and Waters (names: XBridge™ C18, 3.5 µm, 2.1× 50 mm, XBridge™ C18, 5 µm, 2.1×50 mm, XBridge™ C18, 2.5 μm, 2.1×20 mm or Sunfire™ C18, 3.5 m, 2.1×50 mm. The analytical equipment is also equipped with a mass detector in each case.

HPLC-Mass Spectroscopy/UV-Spectrometry

The retention times/MS-ESL for characterizing the example compounds according to the invention are produced using an HPLC-MS apparatus (high performance liquid chromatography with mass detector). Compounds that elute at the injection peak are given the retention time $t_{Ret.}$=0.00.

HPLC-Methods

Method A

| | | | |
|---|---|---|---|
| HPLC | Agilent 1100 Series | | |
| MS | 1200 Series LC/MSD (API-ES + 3000 V, Quadrupol, G6140A) | | |
| MSD signal settings | Scan pos 150-750 | | |
| column | Agilent. Zorbax SB, C8, 3.5 μm, 80 Å, 50 × 2.1 mm column, Part. No.: 871700-906 | | |
| eluant | A: water + 0.11% formic acid<br>B: acetonitrile (HPLC grade) + 0.1% formic acid | | |
| detection signal | UV 254/214/230 nm (bandwidth 8, reference off) | | |
| spectrum | range: 190-450 nm; step: 4.0 nm | | |
| peak width | >0.01 min (0.2 s) | | |
| injection | 1.5 μL standard injection | | |
| flow | 1.1 mL/min | | |
| column temperature | 45° C. | | |
| gradient | 0.0-1.75 min | 15% → 95% B | |
| | 1.75-1.9 min | 95% B | |
| | 1.9-1.92 min | 95% → 15% B | |
| | 1.92-2.1 min | 15% B | |

Method B

| | | | |
|---|---|---|---|
| HPLC | Agilent 1100 Series | | |
| MS | 1200 Series LC/MSD (API-ES + 3000 V, Quadrupol, G6140A) | | |
| MSD signal settings | Scan pos 150-750 | | |
| column | Agilent. Poroshell120 SB, C18, 2.7 μm, 120 Å, 30 × 2.1 mm column, Part. No.: 681775-902 | | |
| eluant | A: water + 0.11% formic acid<br>B: acetonitrile (HPLC grade) + 0.1% formic acid | | |
| detection signal | UV 254/214/230 nm (bandwidth 8, reference off) | | |
| spectrum | range: 190-450 nm; step: 4.0 nm | | |
| peak width | >0.01 min (0.2 s) | | |
| injection | 0.5 μL standard injection | | |
| flow | 1.1 mL/min | | |
| column temperature | 45° C. | | |
| gradient | 0.0-1.00 min | 15% → 95% B | |
| | 1.0-1.1 min | 95% B | |
| | 1.1-1.13 min | 95% → 15% B | |
| | 1.13-1.23 min | 15% B | |

Method C

| | | | |
|---|---|---|---|
| HPLC | LC-20AB | | |
| MS | Autoinjector CTC PAL HTS, LCMS2010EV, UV detector SPD-M20A PDA, ancillary detector PL2100 | | |
| MSD signal settings | Scan pos 100-1000 | | |
| column | Waters Atlantis dC18, 2.1 × 100 mm, 3 μm | | |
| eluant | A: water + 0.1% formic acid<br>B: acetonitrile (HPLC grade) + 0.1% formic acid | | |
| detection signal | UV 215 nm (bandwidth not set) | | |
| spectrum | range: 200-420 nm | | |
| peak width | not set | | |
| injection | 3 μL standard injection | | |
| flow | 1 mL/min | | |
| column temperature | 40° C. | | |
| gradient | 0.00-2.50 min | 5% → 100% B | |
| | 2.50-2.70 min | 100% B | |
| | 2.70-2.71 min | 100% → 5% B | |
| | 2.71-3.50 min | 5% B | |

Method D

| | | | |
|---|---|---|---|
| HPLC | Agilent G1312A | | |
| MS | Autoinjector CTC PAL HTC, MS ZQ, UV detector Waters 2996 PDA, ancillary detector Waters 2420 | | |
| MSD signal settings | Scan pos 150-850 | | |
| column | Waters Atlantis dC18, 2.1 × 100 mm, 3 μm | | |
| eluant | A: water + 0.1% formic acid<br>B: acetonitrile (HPLC grade) + 0.1% formic acid | | |
| detection signal | UV 215 nm (bandwidth not set) | | |
| spectrum | range: 200-420 nm | | |
| peak width | not set | | |
| injection | 3 μL standard injection | | |
| flow | 0.6 mL/min | | |
| column temperature | 40° C. | | |
| gradient | 0.00-5.00 min | 5% → 100% B | |
| | 5.00-5.40 min | 100% B | |
| | 5.40-5.42 min | 100% → 5% B | |
| | 5.42-7.00 min | 5% B | |

Method E

| | | | |
|---|---|---|---|
| HPLC | Agilent 1100 Series | | |
| MS | 1100 Series LC/MSD (API-ES +/− 3000 V, Quadrupol, G1946D) | | |
| MSD signal settings | Scan pos 120-900, Scan neg 120-900 | | |
| column | Phenomenex; Part. No. 00M-4439-BO-CE; Gemini 3 μm, C18, 110 Å; 20 × 2.0 mm column | | |
| eluant | A: 5 mM $NH_4HCO_3$/20 mM $NH_3$ (pH = 9.5)<br>B: acetonitrile (HPLC grade) | | |
| detection signal | UV 254 nm (bandwidth 1, reference off) | | |
| spectrum | range: 250-400 nm; step: 1 nm | | |
| peak width | <0.01 min (0.1 s) | | |
| injection | 10 μL standard injection | | |
| flow | 1.0 mL/min | | |
| column temperature | 40° C. | | |
| gradient | 0.0-2.5 min | 5% → 95% B | |
| | 2.5-2.8 min | 95% B | |
| | 2.8-3.1 min | 95% → 5% B | |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

General Reaction Scheme and Summary of the Synthesis Route
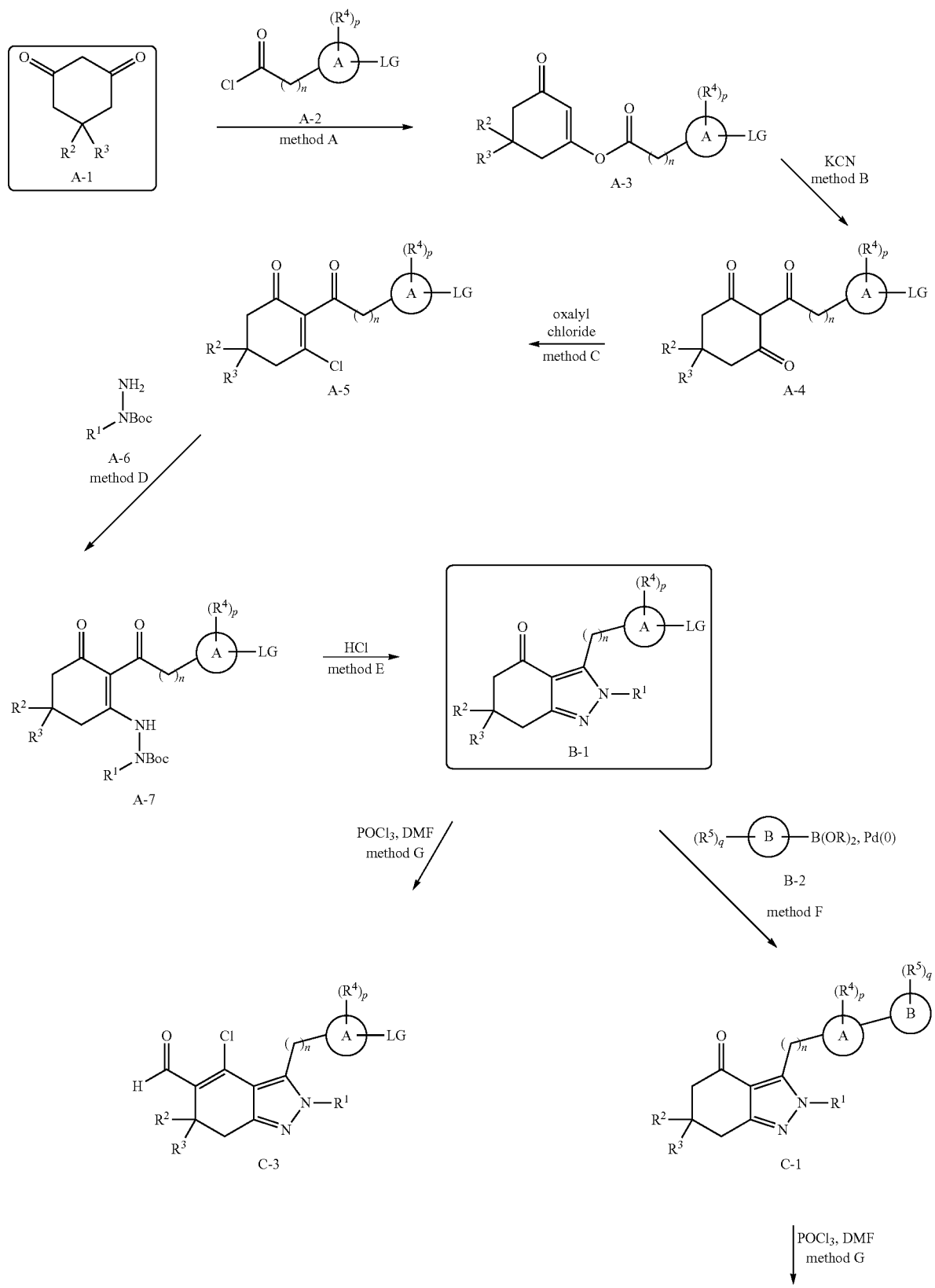

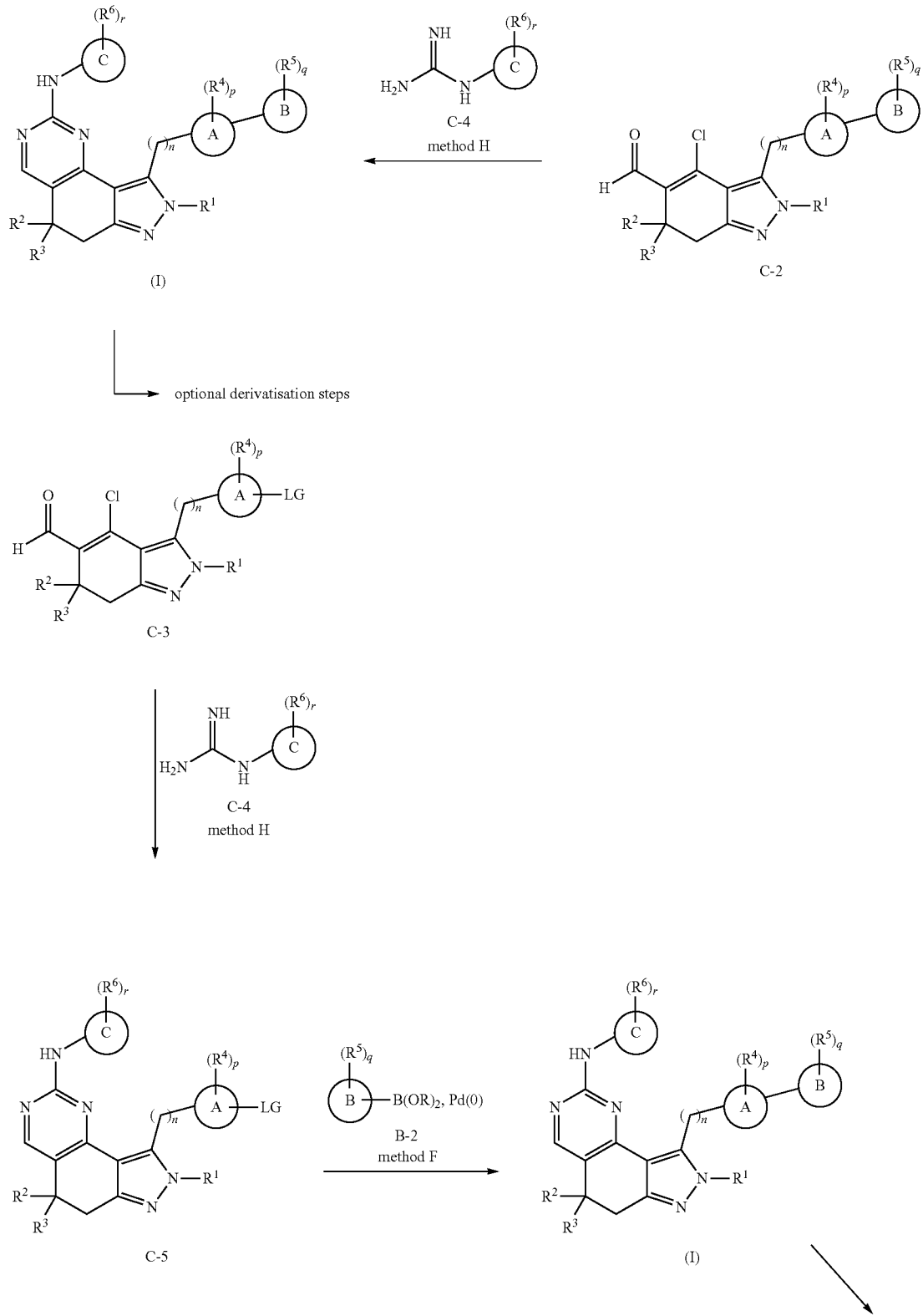

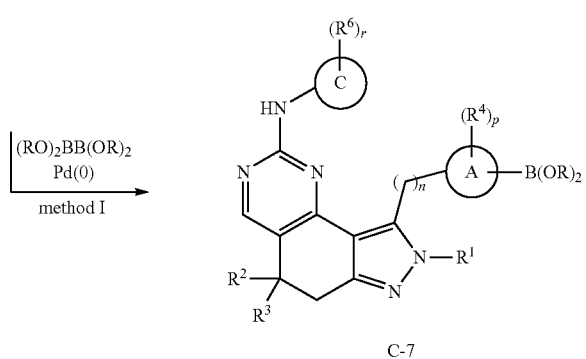
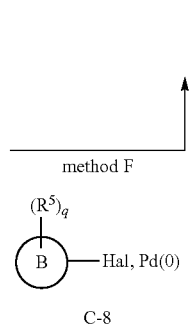

C-7 opt. derivatisation steps method F

C-8

Novel compounds of general structure (I) may be prepared starting from cyclic 1,3-diketones A-1 by a synthesis route leading to the central keto building block B-1:

Starting compounds A-1 are reacted with acid chlorides A-2 and the intermediate enol esters A-3 are subsequently rearranged into the triketones A-4, which can be converted with oxalyl chloride into the vinyl chlorides A-5. Alternatively, carboxylic acids can be activated (e.g. chlorides in situ) and acylate directly to triketones A-4. Substitution of A-5 with protected hydrazines $R^1NHNH_2$ (A-6) leads to the intermediates A-7, which cyclise in the hydrochloric acid medium after the cleaving of the protective group to form the central keto building block B-1.

B-1 may be either formylated with phosphorus oxychloride in the presence of DMF obtaining C-3 (VILSMEIER) or first coupled (SUZUKI) to form the bi(hetero)aryl C-1 which is than formylated as well to obtain C-2.

Intermediates C-2 may be ring closed directly with guanidines C-4 available from amines using known methods and compounds (I) are obtained.

Compounds (I) are also available from C-3 by the same pyrimidine ring closure with guanidines C-4 (→C-5) followed by bi(hetero)aryl formation with boronates B-2 (SUZUKI). Alternatively, the leaving group (LG) in intermediates C-5 may be replaced by a boronic acid functionality and then SUZUKI coupled with heteroaryl halides C-8.

Compounds (I) which are directly synthesized following the synthetic route depicted in the general reaction scheme and which carry functional groups, either on rings A, B or C, that can be further modified such as e.g. halogen atoms, amino and hydroxy groups (including cyclic amines), carboxylic acid or ester functions, nitrils etc. can be optionally derivatized to further compounds (I) by well established organic chemical transformations such as metal-catalyzed cross coupling reactions, acylation, amidation, addition, reduction or (reductive) alkylation or cleavage of protecting groups. These additional steps are not depicted in the general scheme. Likewise, it is also possible to include these additional steps in the synthetic routes depicted in the general scheme, i.e. to carry out derivatization reactions with intermediate compounds. In addition, it may also be possible that building blocks bearing protecting groups are used, i.e. further steps for deprotection are necessary.

A. Synthesis of the Central Keto Building Blocks B-1

A.1. Synthesis of Enol Esters A-3 (Method A)

A.1.1. Experimental Procedure for the Synthesis of A-3a

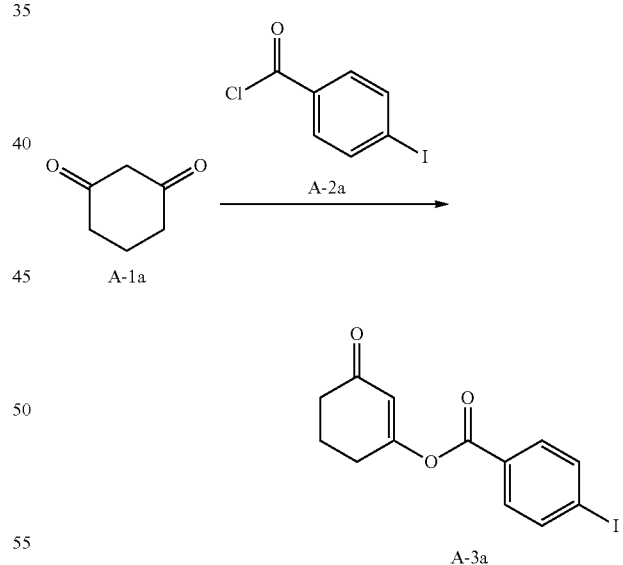

4-Iodobenzoylchloride (13.4 g, 50.4 mmol) in dry toluene (30 mL) is added to a mixture of 1,3-cyclohexanedione (5.65 g, 50.4 mmol) and N-ethyl diisopropylamine (17.0 mL, 99 mmol) in dry toluene (20 mL) and stirred for 1 h at rt. The reaction mixture is washed with water and brine, the organic layer is dried ($Na_2SO_4$), filtered and concentrated in vacuo.

The following enol esters A-3 (table 1) are available in an analogous manner starting from different diketones A-1 and acid chlorides A-2, respectively.

TABLE 1

| # | Structure | $t_{ret}$ [min] | [M + H]$^+$ | HPLC method |
|---|---|---|---|---|
| A-3a | 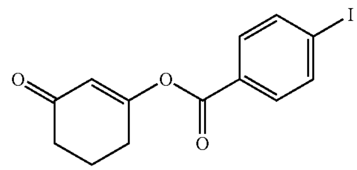 [SMILES: O=C1C=C(OC(=O)c2ccc(I)cc2)CCC1] | 1.21 | 343 | A |
| A-3b | 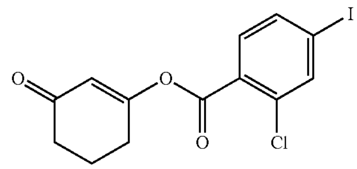 [SMILES: O=C1C=C(OC(=O)c2ccc(I)cc2Cl)CCC1] | 1.27 | 377 | A |
| A-3c | 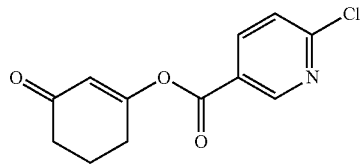 [SMILES: O=C1C=C(OC(=O)c2ccc(Cl)nc2)CCC1] | 0.48 | 252 | B |
| A-3d | 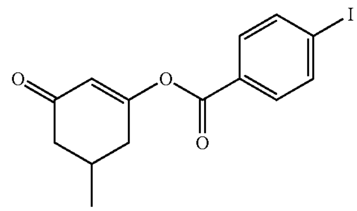 [SMILES: CC1CC(=O)C=C(OC(=O)c2ccc(I)cc2)C1] | 0.75 | 357 | B |

A.2. Synthesis of Triketones A-4 (Method B)

A.2.1. Experimental Procedure for the Synthesis of A-4a

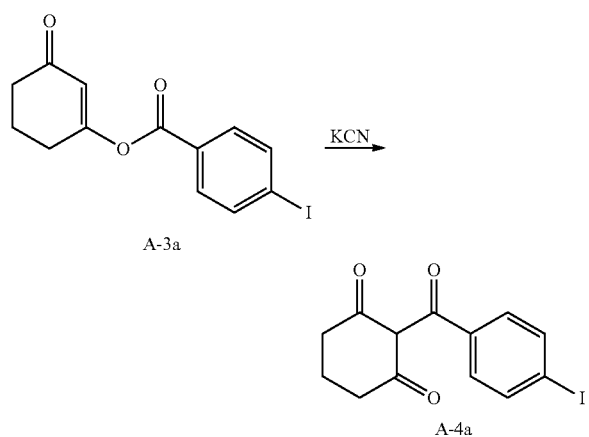

A-3a (16.1 g, 47.1 mmol), triethylamine (13.0 mL, 93.4 mmol) and KCN (500 mg, 7.68 mmol) in MeCN (25 mL) is stirred for 17 h at rt. Water (50 mL) is added, the mixture is neutralized with AcOH and extracted exhaustively with dichloromethane. The combined organic layer is washed with water and brine, dried (Na$_2$SO$_4$), filtered and concentrated in vacuo.

The following triketones A-4 (table 2) are available in an analogous manner starting from different enol esters A-3.

TABLE 2

| # | Structure | $t_{ret}$ [min] | [M + H]$^+$ | HPLC method |
|---|---|---|---|---|
| A-4a | 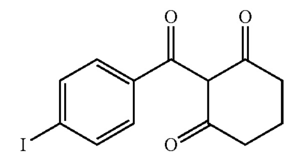 [SMILES: O=C1CCCC(=O)C1C(=O)c1ccc(I)cc1] | 1.03 | 343 | A |
| A-4b | 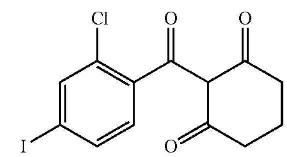 [SMILES: O=C1CCCC(=O)C1C(=O)c1ccc(I)cc1Cl] | 1.22 | 377 | A |
| A-4c | 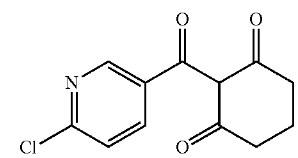 [SMILES: O=C1CCCC(=O)C1C(=O)c1ccc(Cl)nc1] | 0.36 | 252 | B |
| A-4d | 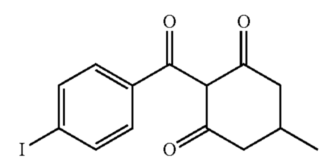 [SMILES: CC1CC(=O)C(C(=O)c2ccc(I)cc2)C(=O)C1] | 0.35 | 357 | B |
| A-4e | 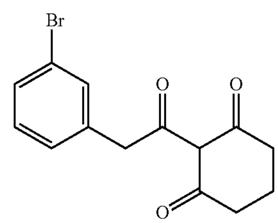 [SMILES: O=C1CCCC(=O)C1C(=O)Cc1cccc(Br)c1] | 0.70 | 309/311 | B |

A.3. Synthesis of Vinyl Chlorides A-5 (Method C)

A.3.1. Experimental Procedure for the Synthesis of A-5a

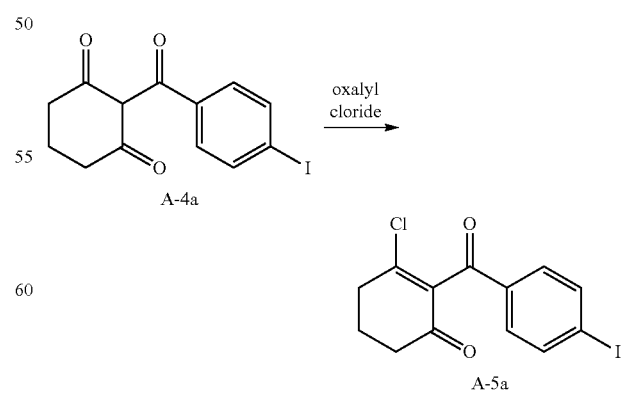

Oxalyl chloride (3.50 mL, 41.6 mmol) is added to A-4a (13.1 g, 38.3 mmol) in dry dichloromethane (25 mL) and stirred for 1.5 h at rt. The reaction mixture is concentrated in vacuo and used for the next step immediately without further purification. (Comment: For HPLC analysis a small sample is quenched with morpholine.)

The following vinyl chlorides A-5 (table 3) are available in an analogous manner starting from different triketones A-4.

TABLE 3

| # | Structure | $t_{ret}$ [min] | $[M + H]^+$ | HPLC method |
|---|---|---|---|---|
| A-5a | 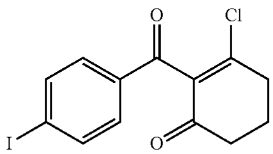 [SMILES: O=C1CCCC(Cl)=C1C(=O)c1ccc(I)cc1] | 0.80[1] | 412 | A |
| A-5b | 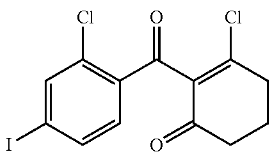 [SMILES: O=C1CCCC(Cl)=C1C(=O)c1ccc(I)cc1Cl] | 0.82[1] | 446 | A |
| A-5c | 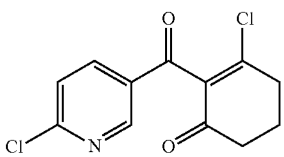 [SMILES: O=C1CCCC(Cl)=C1C(=O)c1ccc(Cl)nc1] | 0.23[1] | 321 | B |
| A-5d | 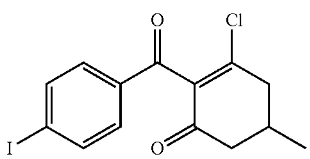 [SMILES: CC1CC(=O)C(C(=O)c2ccc(I)cc2)=C(Cl)C1] | 0.75 | 375 | B |
| A-5e | 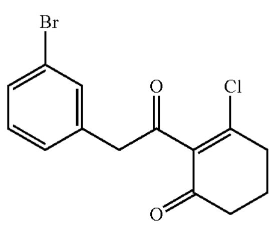 [SMILES: O=C1CCCC(Cl)=C1C(=O)Cc1cccc(Br)c1] | 0.47[1] | 378/380 | B |
| A-5f | 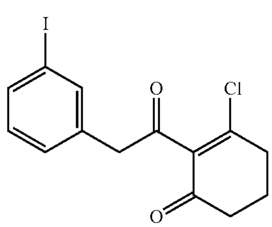 [SMILES: O=C1CCCC(Cl)=C1C(=O)Cc1cccc(I)c1] | 2.15 | 375 | C |

[1]HPLC samples are quenched with morpholine prior to HPLC analysis

A.4. Synthesis of Hydrazides A-7 (Method D)

A.4.1. Experimental Procedure for the Synthesis of A-7a

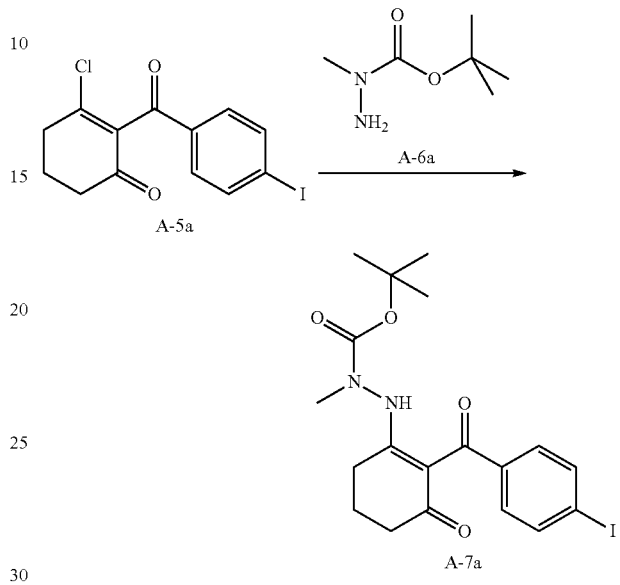

N-Ethyl diisopropylamine (13.2 mL, 77.1 mmol) and 1-Boc-1-methylhydrazine A-6a (6.20 mL, 41.1 mmol) is added to A-5a (13.8 g, 38.3 mmol) in dry THF (20 mL) and stirred for 18 h at rt. The reaction mixture is immediately used for the next step.

The following hydrazides A-7 (table 4) are available in an analogous manner starting from different vinyl chlorides A-5.

TABLE 4

| # | Structure | $t_{ret}$ [min] | $[M + H]^+$ | HPLC method |
|---|---|---|---|---|
| A-7a | 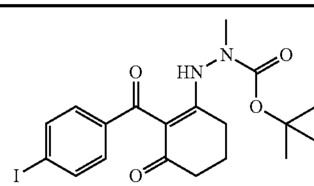 | 1.17 | 471 | A |
| A-7b | 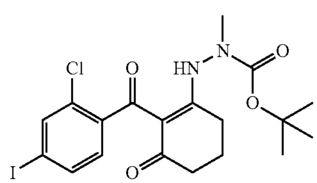 [SMILES: CN(NC1=C(C(=O)c2ccc(I)cc2Cl)C(=O)CCC1)C(=O)OC(C)(C)C] | 1.32 | 505 | A |
| A-7d | 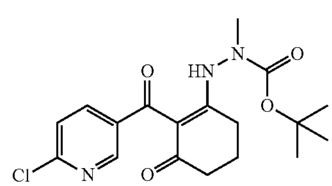 [SMILES: CN(NC1=C(C(=O)c2ccc(Cl)nc2)C(=O)CCC1)C(=O)OC(C)(C)C] | 0.54 | 380 | B |

TABLE 4-continued

| # | Structure | $t_{ret}$ [min] | $[M+H]^+$ | HPLC method |
|---|---|---|---|---|
| A-7e | 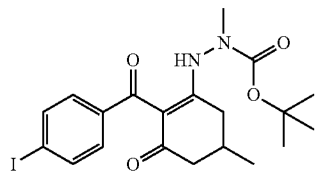 [SMILES: CC1CC(=O)C(C(=O)c2ccc(I)cc2)=C(NN(C)C(=O)OC(C)(C)C)C1] | 0.72 | 485 | B |
| A-7c | 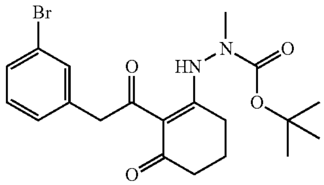 [SMILES: CN(NC1=C(C(=O)Cc2cccc(Br)c2)C(=O)CCC1)C(=O)OC(C)(C)C] | 0.77 | 437/439 | B |
| A-7f | 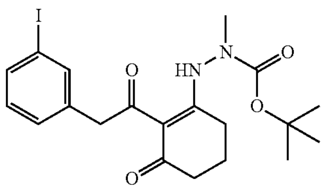 [SMILES: CN(NC1=C(C(=O)Cc2cccc(I)c2)C(=O)CCC1)C(=O)OC(C)(C)C] | 2.28 | 485 | C |

A.5. Synthesis of Pyrazoles B-1 (Method E)

A.5.1. Experimental Procedure for the Synthesis of B-1a

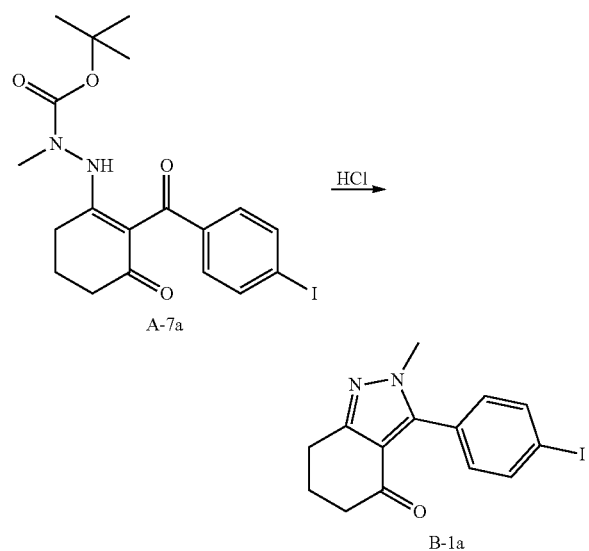

The reaction mixture containing A-7a is treated with conc. HCl (30 mL) and stirred for 2 h at rt. Dichloromethane is added and the organic layer is repeatedly washed with water, 1 N NaOH and brine, dried (Na$_2$SO$_4$), filtered and concentrated in vacuo. The crude product is purified by flash chromatography if necessary.

The following pyrazoles B-1 (table 5) are available in an analogous manner starting from different hydrazides A-7.

TABLE 5

| # | Structure | $t_{ret}$ [min] | $[M+H]^+$ | HPLC method |
|---|---|---|---|---|
| B-1a | 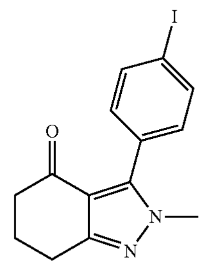 [SMILES: Cn1nc2c(c1-c1ccc(I)cc1)C(=O)CCC2] | 1.05 | 353 | A |
| B-1b | 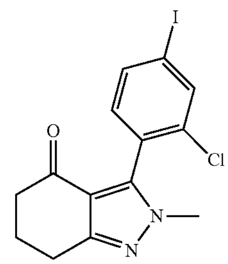 [SMILES: Cn1nc2c(c1-c1ccc(I)cc1Cl)C(=O)CCC2] | 1.11 | 387 | A |
| B-1c | 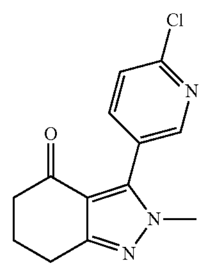 [SMILES: Cn1nc2c(c1-c1ccc(Cl)nc1)C(=O)CCC2] | 0.37 | 262 | B |
| B-1d | 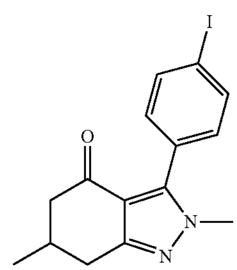 | 0.64 | 367 | B |
| B-1e | 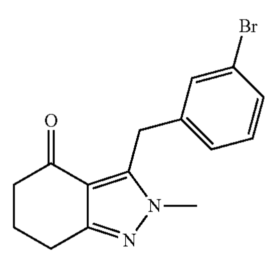 | 0.58 | 319/321 | B |
| B-1f | 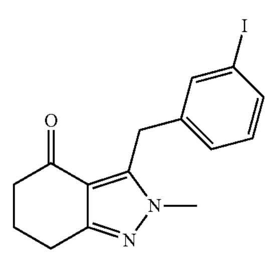 [SMILES: Cn1nc2c(c1Cc1cccc(I)c1)C(=O)CCC2] | 1.96 | 367 | C |

B. Synthesis of Functionalized Central Keto Building Blocks C-1

B.1. Suzuki Coupling (Method F)

B.1.1. Experimental Procedure for the Synthesis of C-1a

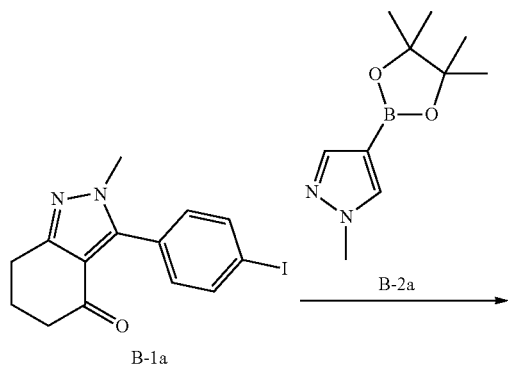

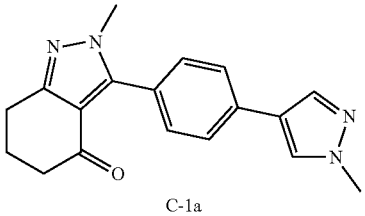

To B-1a (2.0 g, 5.68 mmol), 1-methyl-4-(4,4,5,5-tetramethyl-1,3,2-dioxoborolan-2-yl)-1H-pyrazole B-2a (1.35 g, 6.49 mmol) and tetrakis(triphenylphosphine)palladium(0) (75 mg, 65 µmol) in dioxane (7 mL)/methanol (7 mL) 2 M $K_2CO_3$ (5.7 mL, 11.4 mmol) is added, and the mixture is stirred for 15 min at 120° C. in a microwave reactor under an argon atmosphere. Water is added, and the reaction mixture is extracted exhaustively with dichloromethane. The combined organic layer is repeatedly washed with water and brine, dried ($Na_2SO_4$), filtered and concentrated in vacuo. The crude product is purified by flash chromatography or crystallization if necessary.

The following coupling products C-1 (table 6) are obtained in an analogous manner with different pyrazoles B-1 and boronic acid esters B-2, respectively.

TABLE 6

| # | Structure | $t_{ret}$ [min] | $[M + H]^+$ | HPLC method |
|---|---|---|---|---|
| C-1a | 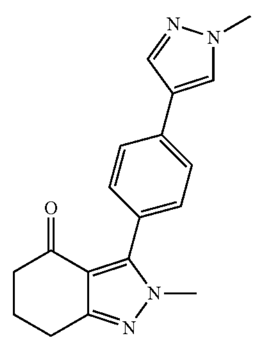 [SMILES: Cn1cc(-c2ccc(-c3c4c(nn3C)CCCC4=O)cc2)cn1] | 0.44 | 307 | B |
| C-1b | 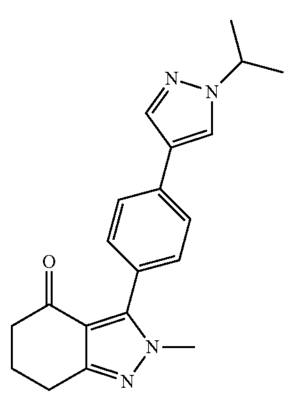 [SMILES: CC(C)n1cc(-c2ccc(-c3c4c(nn3C)CCCC4=O)cc2)cn1] | 1.00 | 335 | A |

TABLE 6-continued

| # | Structure | $t_{ret}$ [min] | [M + H]⁺ | HPLC method |
|---|---|---|---|---|
| C-1c | 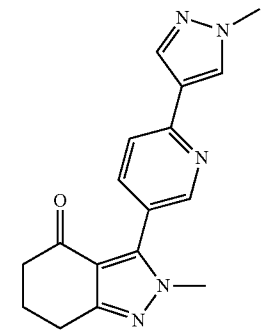 [SMILES: Cn1cc(-c2ccc(-c3c4c(nn3C)CCCC4=O)cn2)cn1] | 0.30 | 308 | B |
| C-1d | 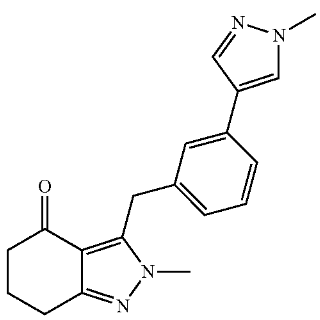 [SMILES: Cn1cc(-c2cccc(Cc3c4c(nn3C)CCCC4=O)c2)cn1] | 0.47 | 321 | B |

C. Synthesis of Example Compounds (I)

C.1. Vilsmeier Formylation (Method G)

C.1.1. Experimental Procedure for the Synthesis of C-3a

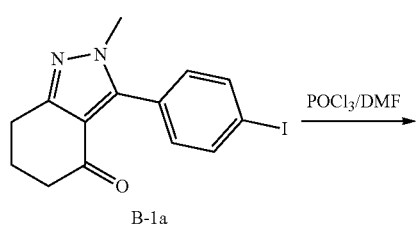

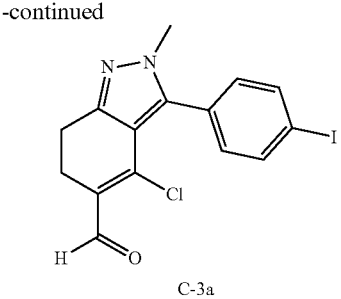

POCl₃ (1.45 mL, 15.8 mmol) is added to DMF (1.53 mL, 19.9 mmol) in dry dichloromethane (15 mL) at 0° C. and stirred for 5 min at rt. B-1a (2.0 g, 5.68 mmol) is added and stirred for 15 min at rt, then the mixture is stirred for 25 min at 110° C. in a microwave reactor. Dichloromethane and water are carefully added to the cold reaction mixture and the aqueous layer is extracted exhaustively with dichloromethane. The combined organic layer is repeatedly washed with water and brine, dried (Na₂SO₄), filtered and concentrated in vacuo. The crude product is used for the next step immediately.

The following formylation products C-2 and C-3 (table 7) are obtained in an analogous manner with different pyrazoles B-1 and C-1, respectively.

TABLE 7
| # | Structure | $t_{ret}$ [min] | $[M + H]^+$ | HPLC method |
|---|---|---|---|---|
| C-3a | 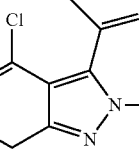 | 1.34 | 399 | A |
| C-3b | 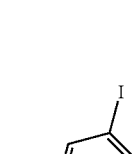 | 1.40 | 433 | A |
| C-3c | 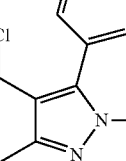 | 0.79 | 413 | B |
| C-3d | 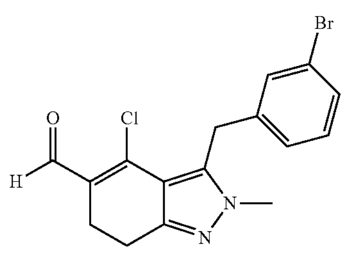 [SMILES: Cn1nc2c(c1Cc1cccc(Br)c1)C(Cl)=C(C=O)CC2] | 0.60 | 367 | B |
| C-3e | 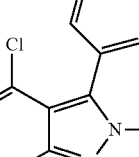 | 2.27 | 413 | C |

TABLE 7-continued
| # | Structure | $t_{ret}$ [min] | $[M + H]^+$ | HPLC method |
|---|---|---|---|---|
| C-2a | 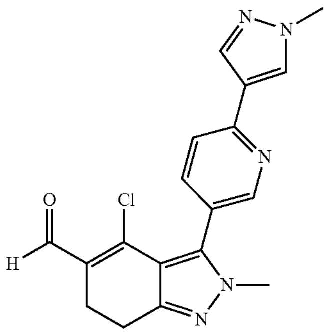 [SMILES: Cn1cc(-c2ccc(-c3c4c(nn3C)CCC(C=O)=C4Cl)cn2)cn1] | 0.47 | 354 | B |
| C-2b | 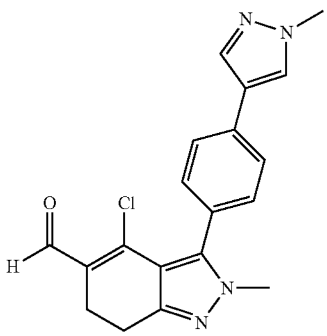 [SMILES: Cn1cc(-c2ccc(-c3c4c(nn3C)CCC(C=O)=C4Cl)cc2)cn1] | 1.13 | 353 | A |
| C-2c | 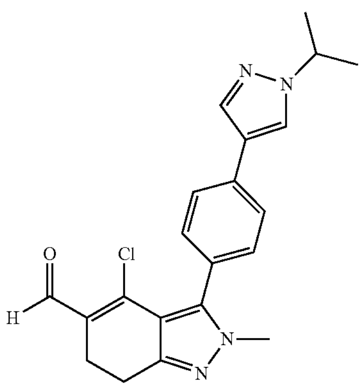 [SMILES: CC(C)n1cc(-c2ccc(-c3c4c(nn3C)CCC(C=O)=C4Cl)cc2)cn1] | 1.26 | 381 | A |
C.2. Pyrimidine Formation (Method H)
C.2.1. Experimental Procedure for the Synthesis of C-5a
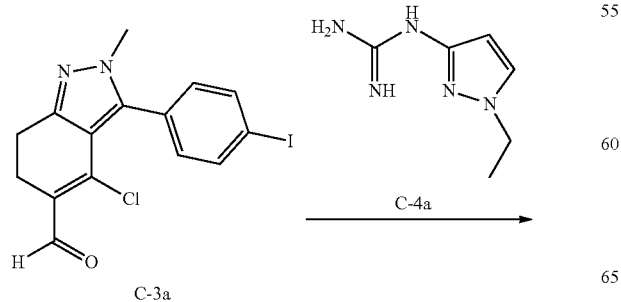
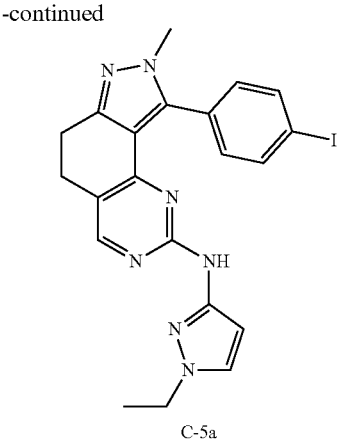
Morpholine (3.0 mL, 34.5 mmol) is added to N-(1-ethyl-1H-pyrazol-3-yl)-guanidine hydrochloride (1.15 g, 6.06 mmol) and C-3a (2.26 g, 5.67 mmol) in dry dioxane (10 mL) and stirred for 60 min at 135° C. in a microwave reactor. The product is isolated either by precipitation or by extraction. The crude product is purified by flash chromatography or crystallization if necessary.

Guanidine building blocks C-4 are prepared from the corresponding anilines or aminopyrazoles using cyanamide in dioxane/HCl[2] or 1H-pyrazole-1-carboxamidine hydrochloride[3] in the presence of a base. Complex guanidines are accessible using the procedures of Stephens et al.[4] or H. Ube et al.[5]

[2] WO200441810; US20049996
[3] Rai, R.; Katzenellenbogen, J. A. *J. Med. Chem.* 1992, 35 (22), 4150-4159; Maduskuie, T. P.; McNamara, K. J.; Ru, Y.; Knabb, R. M.; Stouten, P. F. W. *J. Med. Chem.* 1998, 41 (1), 53-62
[4] Stephens, C. E.; Tanious, F.; Kim, S.; Wilson, W. D.; Schell, W. A.; Perfect, J. R.; Franzblau, S. G.; Boykin, D. W. *J. Med. Chem.* 2001, 44 (11), 1741-1748
[5] Ube, H.; Uraguchi, D.; Terada, M. *J. Organomet. Chem.* 2007, 692 (1-3), 545-549

The following ring closure products C-5 (table 8) are obtained in an analogous manner with different vinylchlorides C-3.

TABLE 8

| # | Structure | $t_{ret}$ [min] | $[M + H]^+$ | HPLC method |
|---|---|---|---|---|
| C-5a | 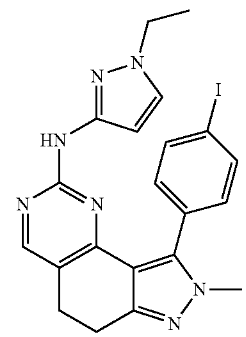 [SMILES: CCn1ccc(Nc2ncc3c(n2)-c2c(nn(C)c2-c2ccc(I)cc2)CC3)n1] | 1.21 | 498 | A |
| C-5b | 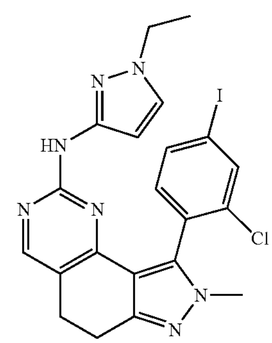 [SMILES: CCn1ccc(Nc2ncc3c(n2)-c2c(nn(C)c2-c2ccc(I)cc2Cl)CC3)n1] | 1.27 | 532 | A |
| C-5c | 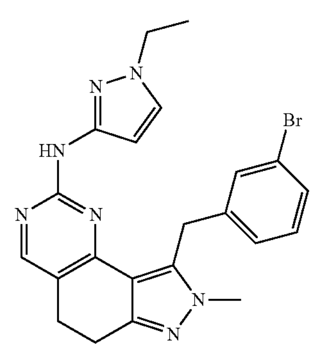 [SMILES: CCn1ccc(Nc2ncc3c(n2)-c2c(nn(C)c2Cc2cccc(Br)c2)CC3)n1] | 1.05 | 464/466 | A |

TABLE 8-continued
| # | Structure | t_ret [min] | [M + H]+ | HPLC method |
|---|---|---|---|---|
| C-5d | 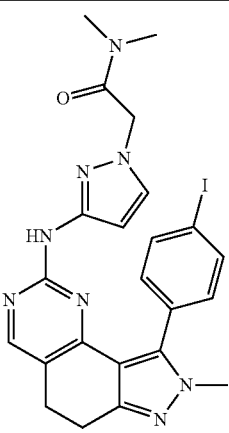 | 0.47 | 555 | B |
| C-5e | 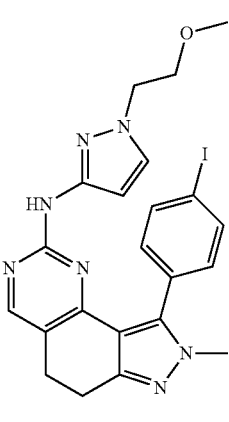 [SMILES: COCCn1ccc(Nc2ncc3c(n2)-c2c(nn(C)c2-c2ccc(I)cc2)CC3)n1] | 0.56 | 528 | B |
| C-5f | 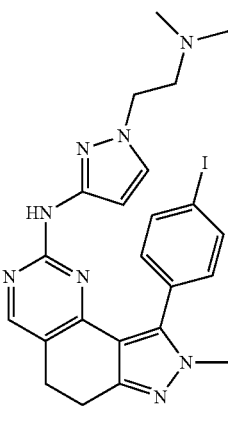 [SMILES: CN(C)CCn1ccc(Nc2ncc3c(n2)-c2c(nn(C)c2-c2ccc(I)cc2)CC3)n1] | 0.71 | 541 | A |
| C-5g | 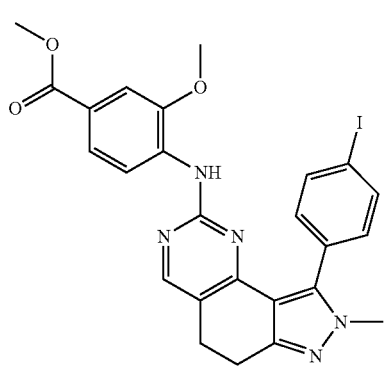 [SMILES: COC(=O)c1ccc(Nc2ncc3c(n2)-c2c(nn(C)c2-c2ccc(I)cc2)CC3)c(OC)c1] | 1.49 | 568 | A |

TABLE 8-continued

| # | Structure | $t_{ret}$ [min] | $[M + H]^+$ | HPLC method |
|---|---|---|---|---|
| C-5h | 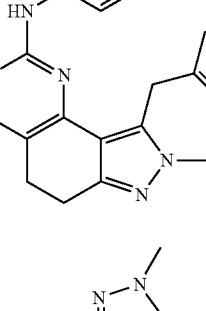 | 0.82 | 534/536 | B |
| C-5i | 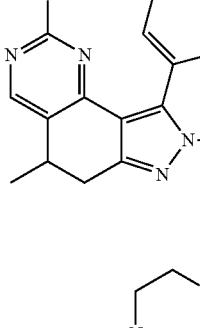 | 0.59 | 498 | B |
| C-5j | 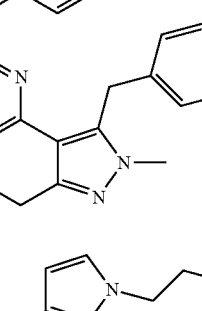 | 0.53 | 602/604 | B |
| C-5k | 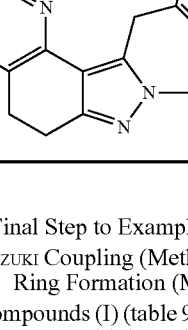 | 1.68 | 542 | C |

C.3. Final Step to Example Compounds (I)

C.3.1. Suzuki Coupling (Method F) or Pyrimidine Ring Formation (Method H)

Example Compounds (I) (table 9) are obtained by coupling the intermediates C-5 with boronic acid esters B-2 (Suzuki, conditions analogous to method F applied for C-1) or by pyrimidine ring formation on cyclic vinyl chlorides C-2 with guanidines C-4 (conditions analogous to method H applied for C-5).

TABLE 9

| # | Structure | $t_{ret}$ [min] | M + H⁺ | HPLC method |
|---|---|---|---|---|
| I-1 | 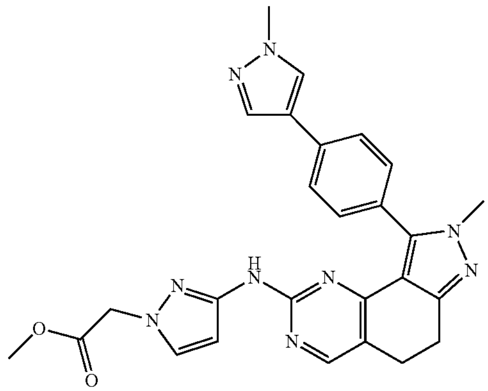 | 0.45 | 496 | B |
| I-2 | 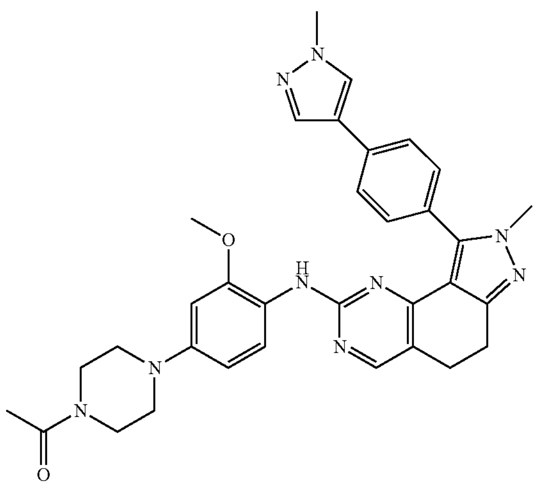 [SMILES: COc1cc(N2CCN(C(C)=O)CC2)ccc1Nc1ncc2c(n1)-c1c(nn(C)c1-c1ccc(-c3cnn(C)c3)cc1)CC2] | 0.45 | 590 | B |
| I-3 | 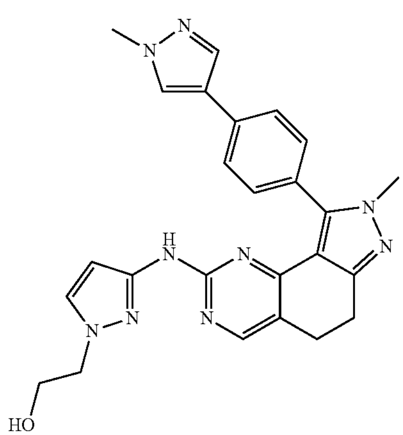 [SMILES: Cn1cc(-c2ccc(-c3c4c(nn3C)CCc3cnc(Nc5ccn(CCO)n5)nc3-4)cc2)cn1] | 1.07 | 468 | E |

TABLE 9-continued

| # | Structure | $t_{ret}$ [min] | M + H$^+$ | HPLC method |
|---|---|---|---|---|
| I-4 | 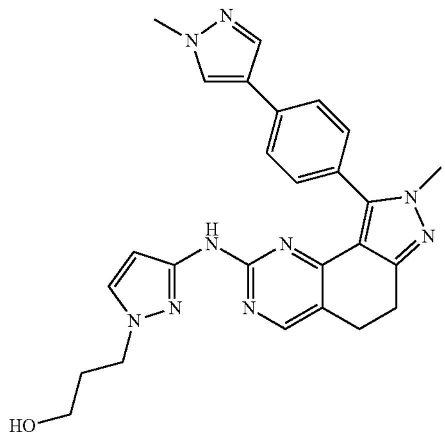 [SMILES: Cn1cc(-c2ccc(-c3c4c(nn3C)CCc3cnc(Nc5ccn(CCCO)n5)nc3-4)cc2)cn1] | 1.09 | 482 | E |
| I-5 | 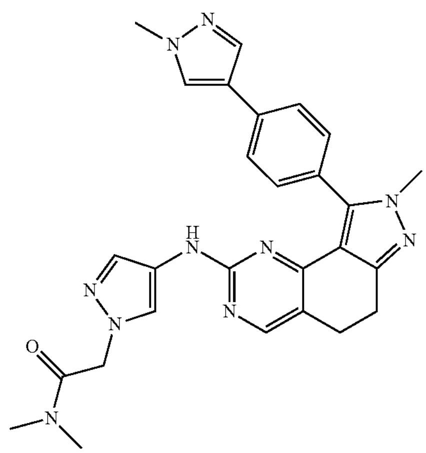 | 1.06 | 509 | E |
| I-6 | 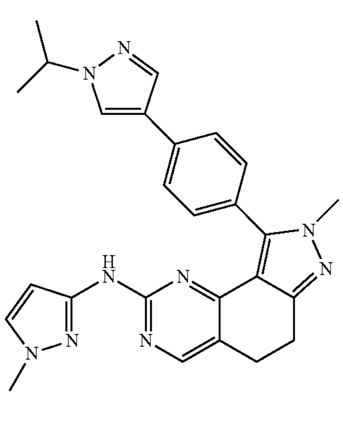 [SMILES: CC(C)n1cc(-c2ccc(-c3c4c(nn3C)CCc3cnc(Nc5ccn(C)n5)nc3-4)cc2)cn1] | 1.24 | 466 | E |

TABLE 9-continued

| # | Structure | $t_{ret}$ [min] | M + H⁺ | HPLC method |
|---|---|---|---|---|
| I-7 | 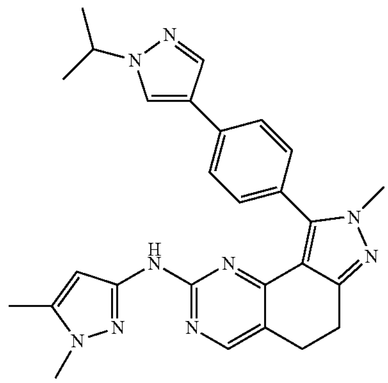 | 1.26 | 480 | E |
| I-8 | 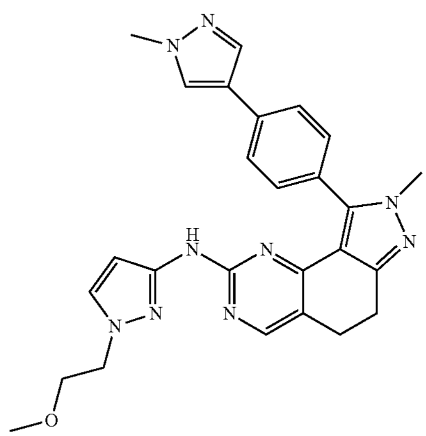 | 1.14 | 482 | E |
| I-9 | 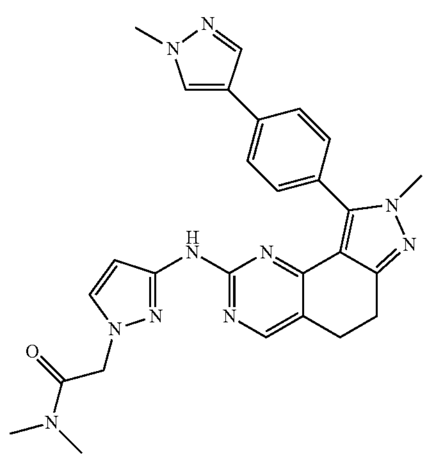 | 1.08 | 509 | E |

TABLE 9-continued
| # | Structure | $t_{ret}$ [min] | M + H⁺ | HPLC method |
|---|---|---|---|---|
| I-10 | 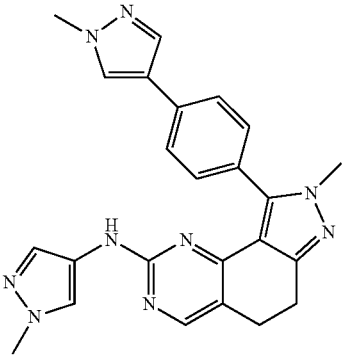 [SMILES: Cn1cc(Nc2ncc3c(n2)-c2c(nn(C)c2-c2ccc(-c4cnn(C)c4)cc2)CC3)cn1] | 1.13 | 438 | E |
| I-11 | 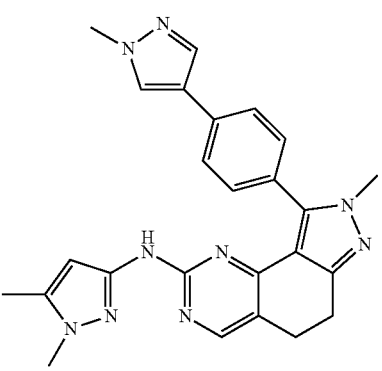 | 1.14 | 452 | E |
| I-12 | 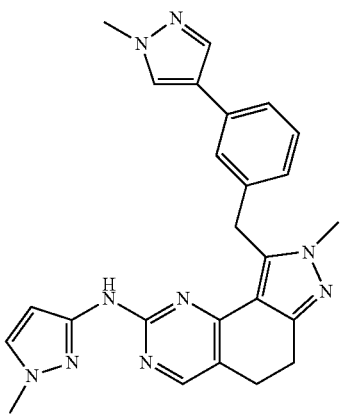 [SMILES: Cn1cc(-c2cccc(Cc3c4c(nn3C)CCc3cnc(Nc5ccn(C)n5)nc3-4)c2)cn1] | 1.16 | 452 | E |

TABLE 9-continued
| # | Structure | $t_{ret}$ [min] | M + H⁺ | HPLC method |
|---|---|---|---|---|
| I-13 | 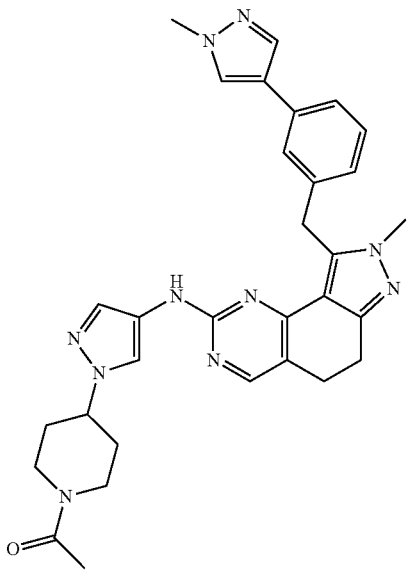 [SMILES: CC(=O)N1CCC(n2cc(Nc3ncc4c(n3)-c3c(nn(C)c3Cc3cccc(-c5cnn(C)c5)c3)CC4)cn2)CC1] | 1.11 | 563 | E |
| I-14 | 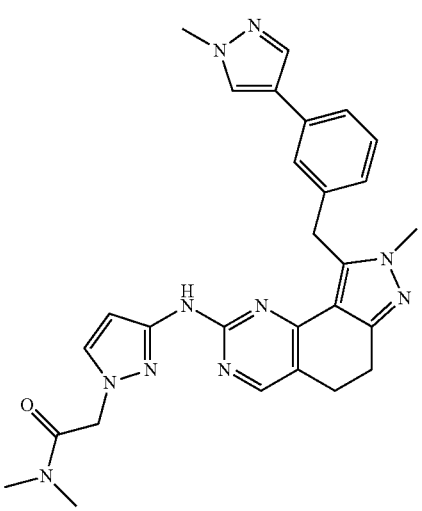 | 1.30 | 523 | E |
| I-15 | 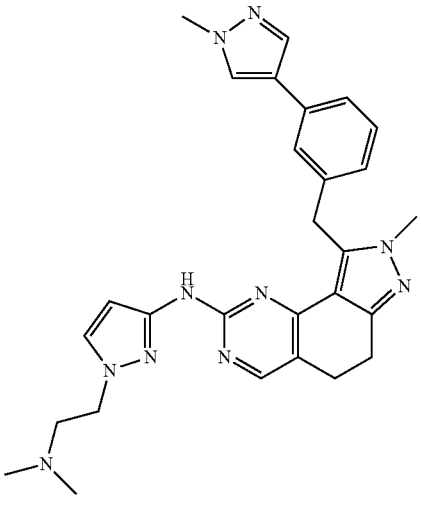 | 1.02 | 509 | E |

TABLE 9-continued
| # | Structure | $t_{ret}$ [min] | M + H$^+$ | HPLC method |
|---|---|---|---|---|
| I-16 | 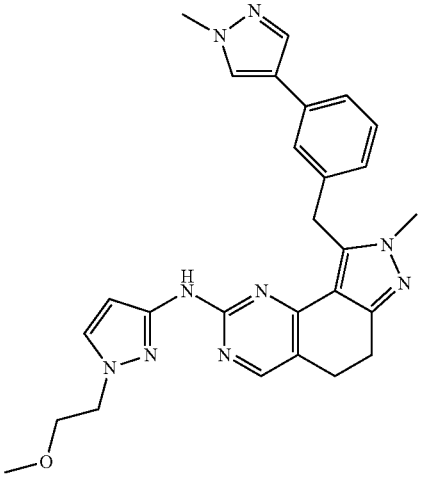 | 1.19 | 496 | E |
| I-17 | 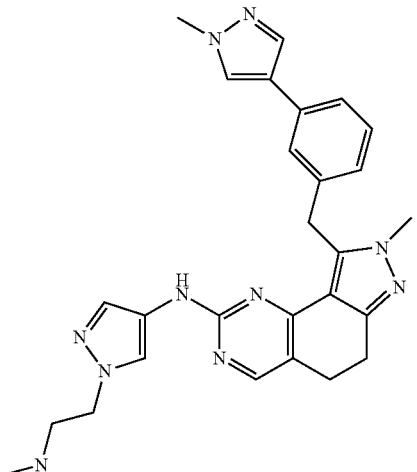 | 1.15 | 509 | E |
| I-18 | 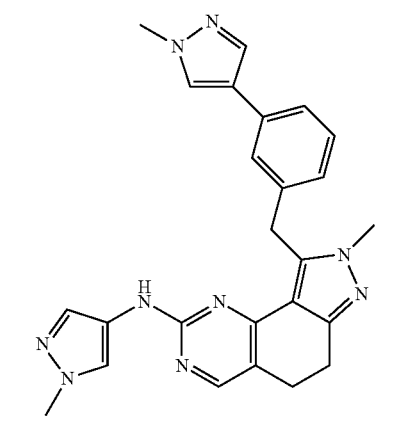 [SMILES: Cn1cc(Nc2ncc3c(n2)-c2c(nn(C)c2Cc2cccc(-c4cnn(C)c4)c2)CC3)cn1] | 1.13 | 452 | E |

TABLE 9-continued

| # | Structure | $t_{ret}$ [min] | M + H⁺ | HPLC method |
|---|---|---|---|---|
| I-19 | 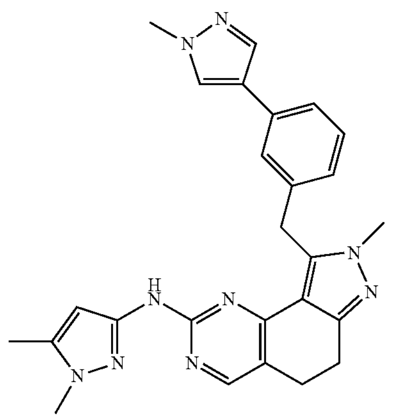 | 1.19 | 466 | E |
| I-20 | 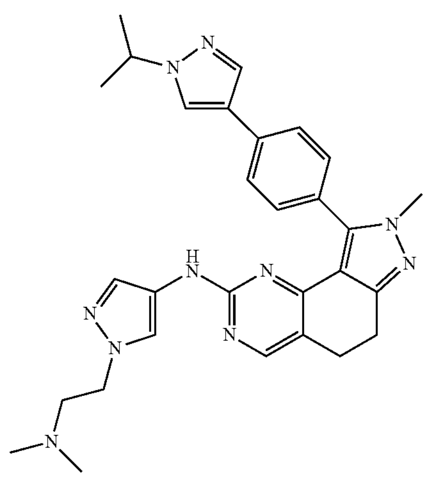 | 1.50 | 523 | E |
| I-21 | 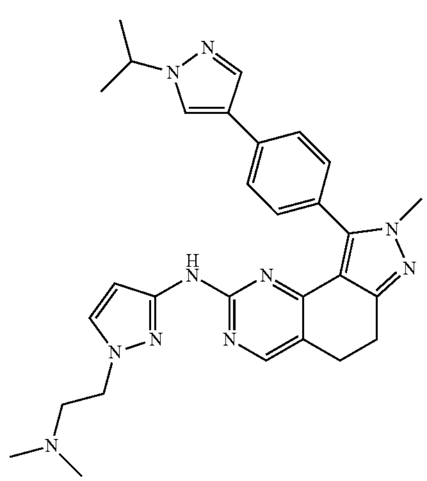 | 1.54 | 523 | E |

TABLE 9-continued
| # | Structure | $t_{ret}$ [min] | M + H⁺ | HPLC method |
|---|---|---|---|---|
| I-22 | 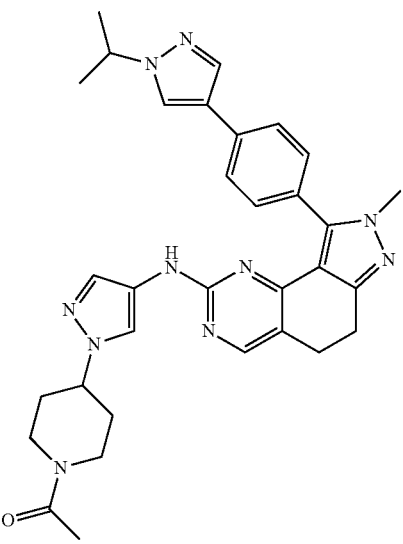 [SMILES: CC(=O)N1CCC(n2cc(Nc3ncc4c(n3)-c3c(nn(C)c3-c3ccc(-c5cnn(C(C)C)c5)cc3)CC4)cn2)CC1] | 1.45 | 577 | E |
| I-23 | 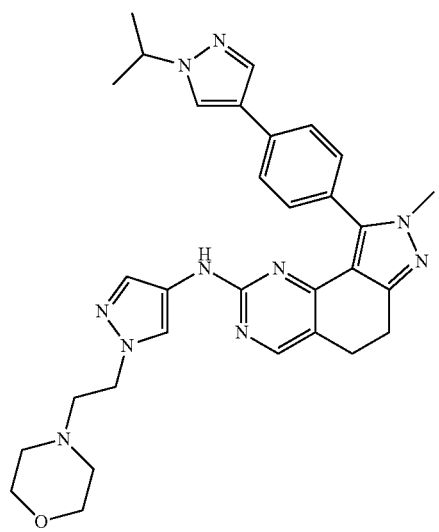 [SMILES: CC(C)n1cc(-c2ccc(-c3c4c(nn3C)CCc3cnc(Nc5cnn(CCN6CCOCC6)c5)nc3-4)cc2)cn1] | 1.47 | 565 | E |
| I-24 | 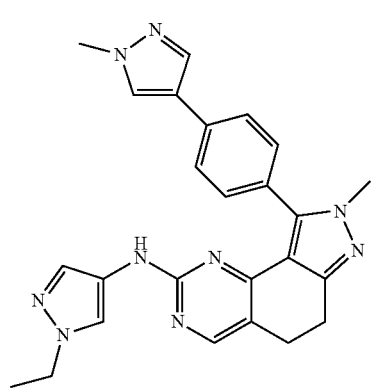 [SMILES: CCn1cc(Nc2ncc3c(n2)-c2c(nn(C)c2-c2ccc(-c4cnn(C)c4)cc2)CC3)cn1] | 1.31 | 452 | E |

TABLE 9-continued
| # | Structure | $t_{ret}$ [min] | M + H⁺ | HPLC method |
|---|---|---|---|---|
| I-25 | 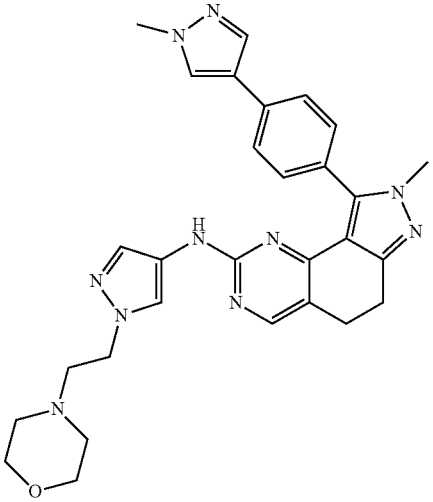 [SMILES: Cn1cc(-c2ccc(-c3c4c(nn3C)CCc3cnc(Nc5cnn(CCN6CCOCC6)c5)nc3-4)cc2)cn1] | 1.26 | 537 | E |
| I-26 | 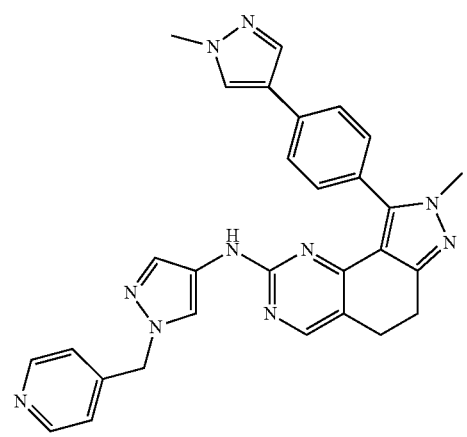 [SMILES: Cn1cc(-c2ccc(-c3c4c(nn3C)CCc3cnc(Nc5cnn(Cc6ccncc6)c5)nc3-4)cc2)cn1] | 1.21 | 515 | E |
| I-27 | 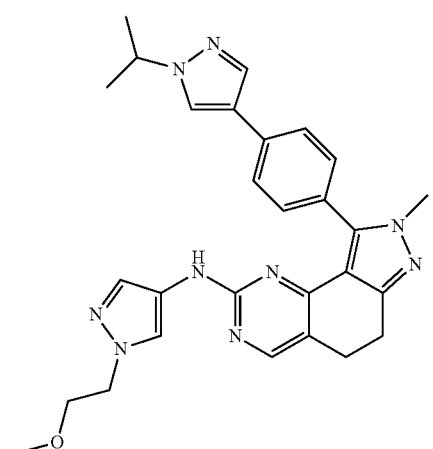 | 1.45 | 510 | E |

TABLE 9-continued
| # | Structure | t_ret [min] | M + H+ | HPLC method |
|---|---|---|---|---|
| I-28 | 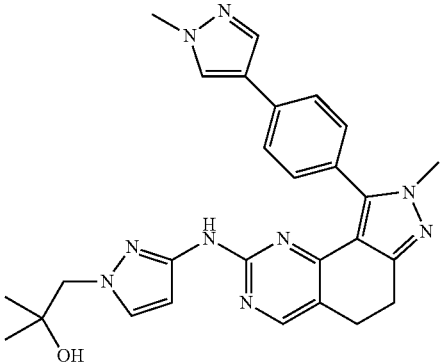 [SMILES: Cn1cc(-c2ccc(-c3c4c(nn3C)CCc3cnc(Nc5ccn(CC(C)(C)O)n5)nc3-4)cc2)cn1] | 0.98 | 496 | E |
| I-29 | 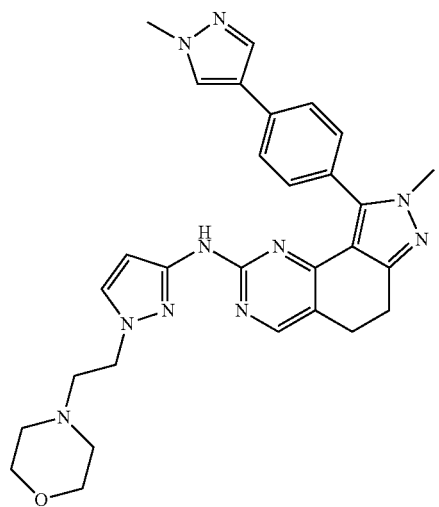 [SMILES: Cn1cc(-c2ccc(-c3c4c(nn3C)CCc3cnc(Nc5ccn(CCN6CCOCC6)n5)nc3-4)cc2)cn1] | 0.97 | 537 | E |
| I-30 | 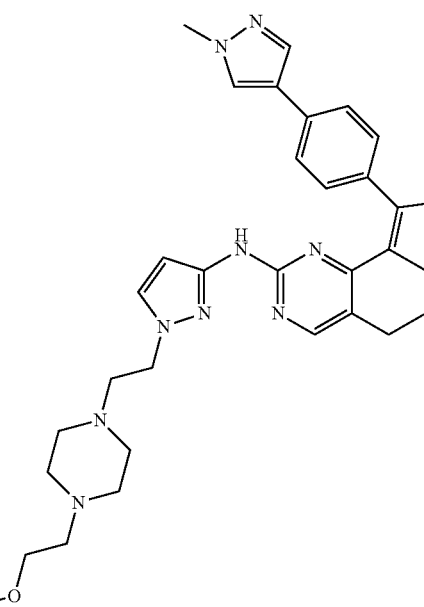 | 0.98 | 594 | E |

TABLE 9-continued
| # | Structure | $t_{ret}$ [min] | M + H⁺ | HPLC method |
|---|---|---|---|---|
| I-31 | 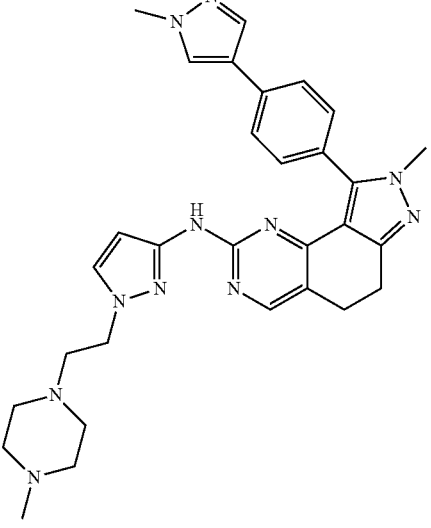 | 0.96 | 550 | E |
| I-32 | 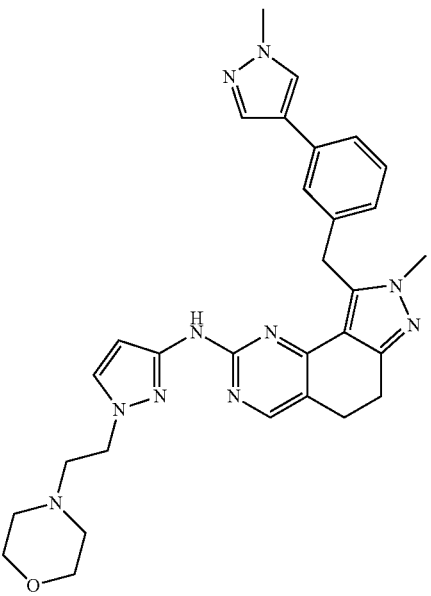 [SMILES: Cn1cc(-c2cccc(Cc3c4c(nn3C)CCc3cnc(Nc5ccn(CCN6CCOCC6)n5)nc3-4)c2)cn1] | 1.00 | 551 | E |

TABLE 9-continued
| # | Structure | $t_{ret}$ [min] | M + H⁺ | HPLC method |
|---|---|---|---|---|
| I-33 | 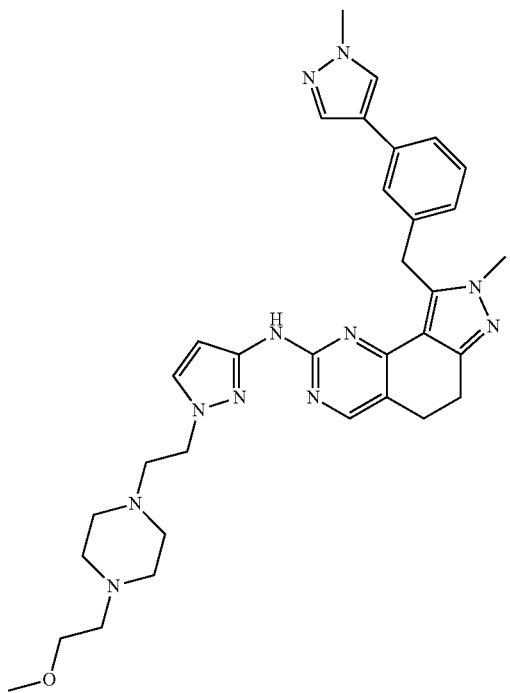 | 1.00 | 608 | E |
| I-34 | 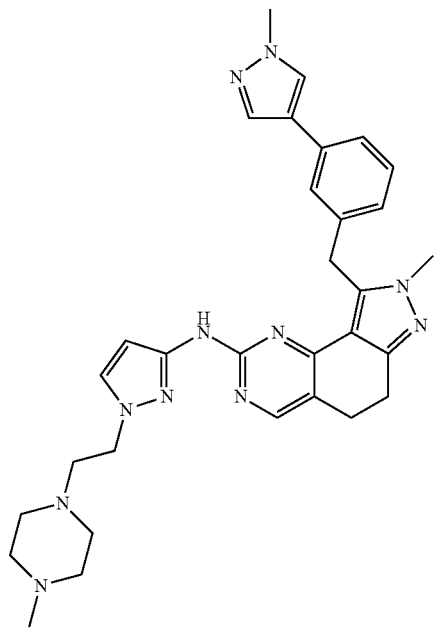 [SMILES: CN1CCN(CCn2ccc(Nc3ncc4c(n3)-c3c(nn(C)c3Cc3cccc(-c5cnn(C)c5)c3)CC4)n2)CC1] | 0.98 | 564 | E |

TABLE 9-continued
| # | Structure | $t_{ret}$ [min] | M + H$^+$ | HPLC method |
|---|---|---|---|---|
| I-35 | 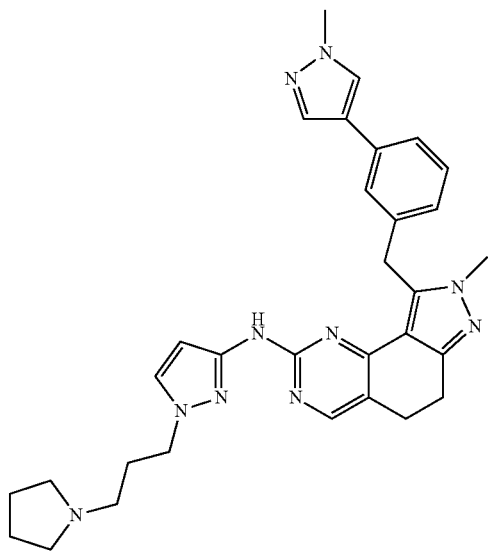 [SMILES: Cn1cc(-c2cccc(Cc3c4c(nn3C)CCc3cnc(Nc5ccn(CCCN6CCCC6)n5)nc3-4)c2)cn1] | 1.06 | 549 | E |
| I-36 | 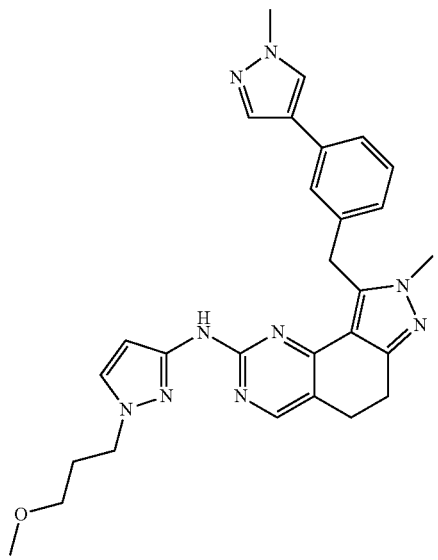 | 1.06 | 510 | E |

TABLE 9-continued
| # | Structure | $t_{ret}$ [min] | M + H⁺ | HPLC method |
|---|---|---|---|---|
| I-37 | 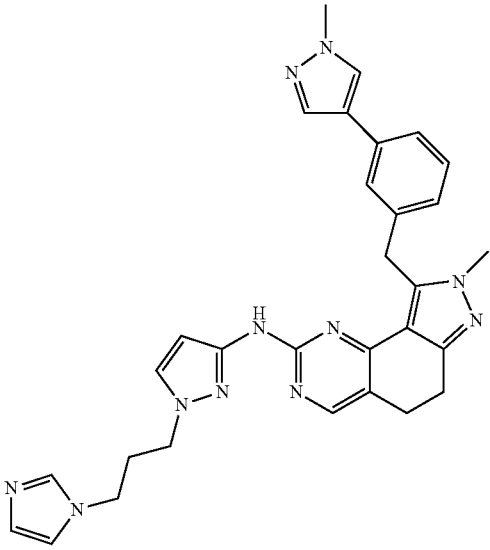 [SMILES: Cn1cc(-c2cccc(Cc3c4c(nn3C)CCc3cnc(Nc5ccn(CCCn6ccnc6)n5)nc3-4)c2)cn1] | 0.98 | 546 | E |
| I-38 | 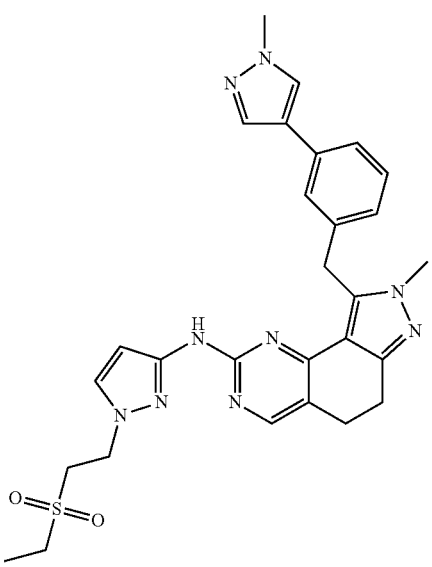 [SMILES: CCS(=O)(=O)CCn1ccc(Nc2ncc3c(n2)-c2c(nn(C)c2Cc2cccc(-c4cnn(C)c4)c2)CC3)n1] | 1.00 | 558 | E |

TABLE 9-continued
| # | Structure | $t_{ret}$ [min] | M + H⁺ | HPLC method |
|---|---|---|---|---|
| I-39 | 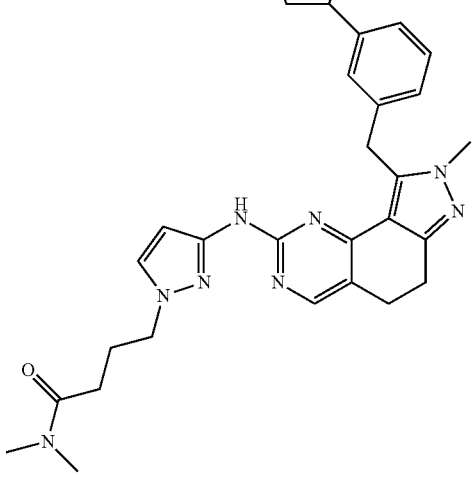 | 0.99 | 551 | E |
| I-40 | 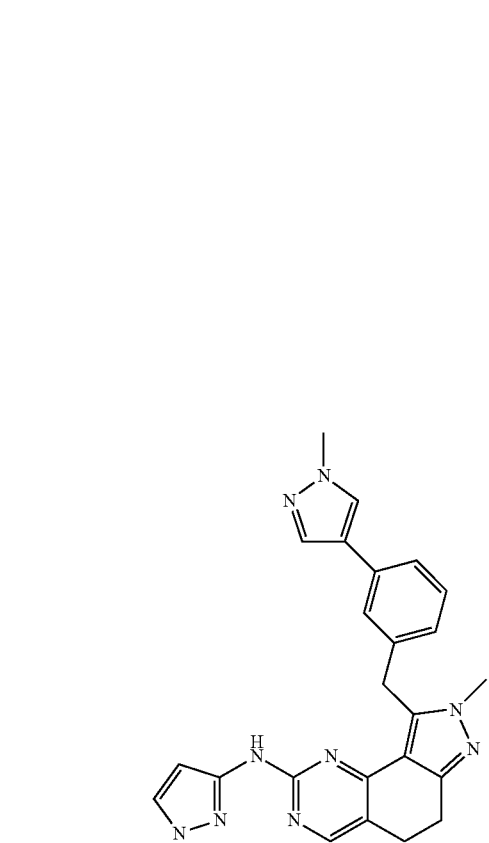 | 0.96 | 566 | E |

TABLE 9-continued

| # | Structure | $t_{ret}$ [min] | M + H⁺ | HPLC method |
|---|---|---|---|---|
| I-41 | 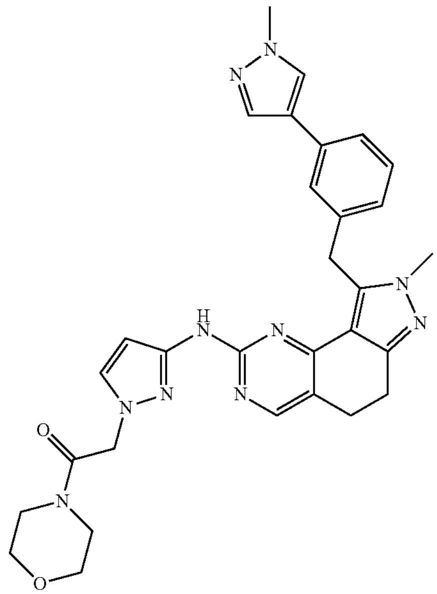 [SMILES: Cn1cc(-c2cccc(Cc3c4c(nn3C)CCc3cnc(Nc5ccn(CC(=O)N6CCOCC6)n5)nc3-4)c2)cn1] | 0.95 | 565 | E |
| I-179 | 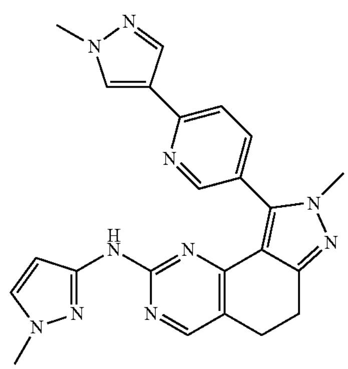 [SMILES: Cn1cc(-c2ccc(-c3c4c(nn3C)CCc3cnc(Nc5ccn(C)n5)nc3-4)cn2)cn1] | 1.02 | 439 | E |
| I-180 | 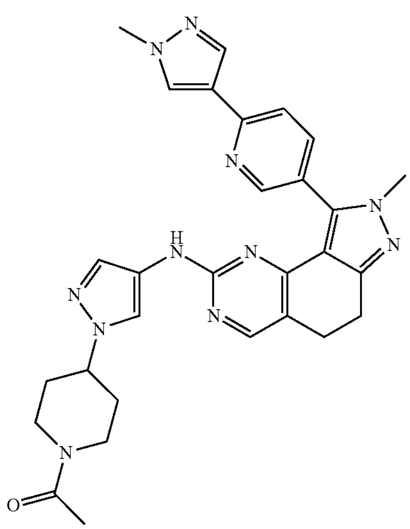 [SMILES: CC(=O)N1CCC(n2cc(Nc3ncc4c(n3)-c3c(nn(C)c3-c3ccc(-c5cnn(C)c5)nc3)CC4)cn2)CC1] | 1.03 | 550 | E |

TABLE 9-continued

| # | Structure | $t_{ret}$ [min] | M + H⁺ | HPLC method |
|---|---|---|---|---|
| I-181 | 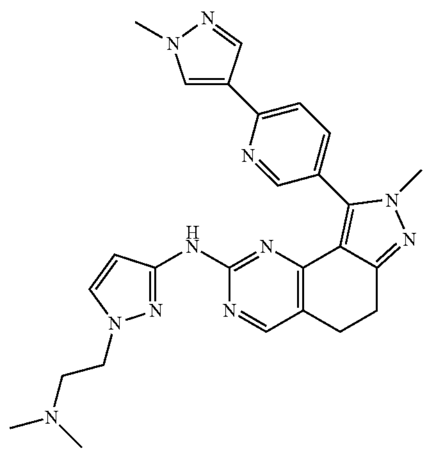 | 1.05 | 496 | E |
| I-182 | 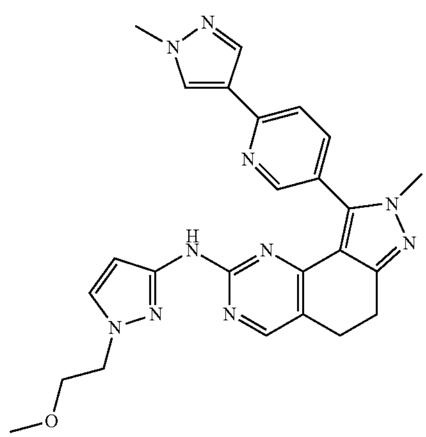 | 1.05 | 483 | E |
| I-183 | 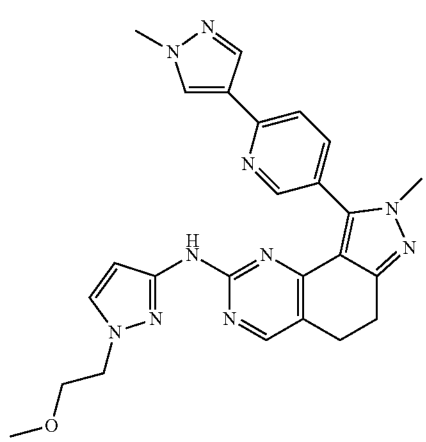 | 0.88 | 483 | E |

TABLE 9-continued

| # | Structure | $t_{ret}$ [min] | M + H⁺ | HPLC method |
|---|---|---|---|---|
| I-184 | 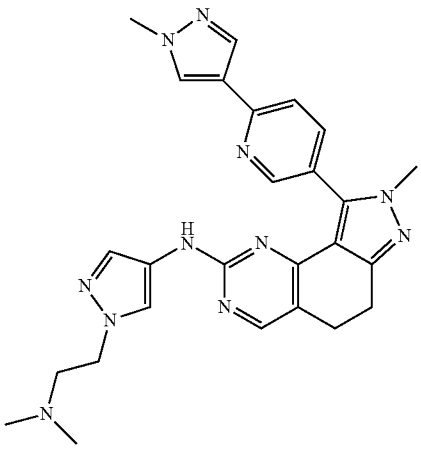 | 1.05 | 496 | E |
| I-185 | 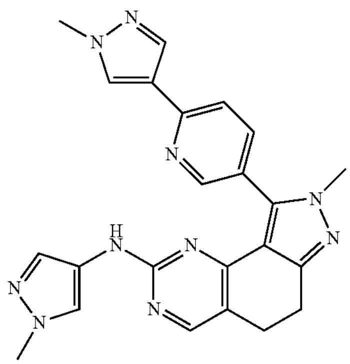 [SMILES: Cn1cc(Nc2ncc3c(n2)-c2c(nn(C)c2-c2ccc(-c4cnn(C)c4)nc2)CC3)cn1] | 1.02 | 439 | E |
| I-186 | 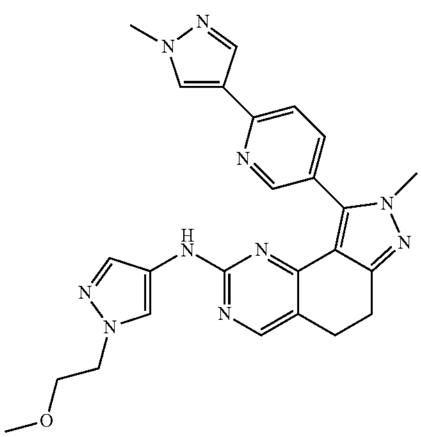 | 0.88 | 483 | E |
| I-187 | 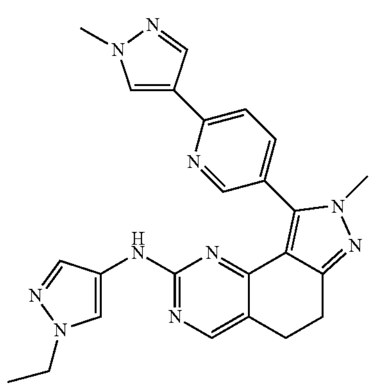 [SMILES: CCn1cc(Nc2ncc3c(n2)-c2c(nn(C)c2-c2ccc(-c4cnn(C)c4)nc2)CC3)cn1] | 0.90 | 453 | E |

TABLE 9-continued
| # | Structure | $t_{ret}$ [min] | M + H⁺ | HPLC method |
|---|---|---|---|---|
| I-188 | 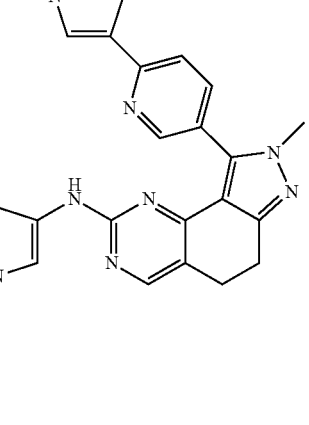 | 0.87 | 538 | E |
| I-189 | 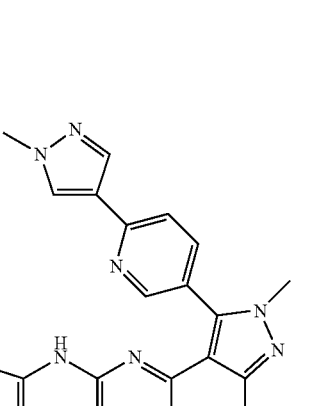 | 0.94 | 467 | E |
C.3.2. "Inverted" Suzuki Coupling (Method I and F)
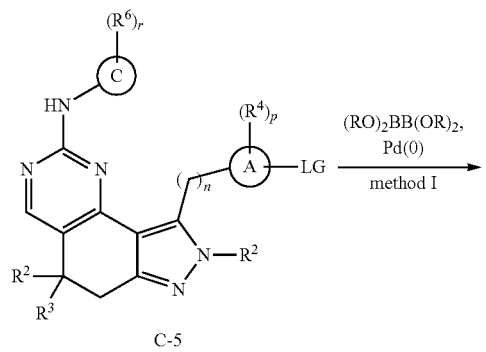
C-5
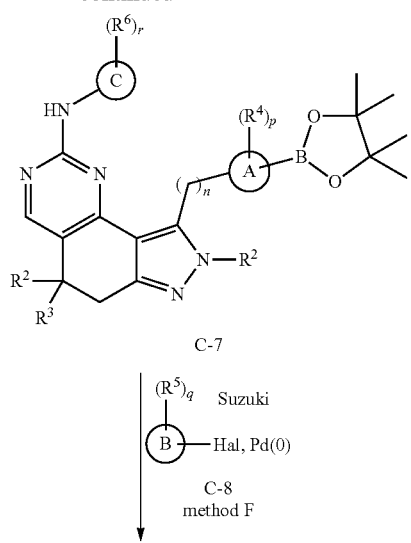
C-7
-continued

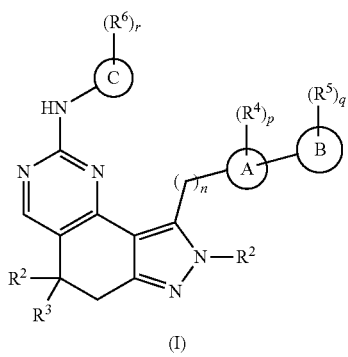

C.3.2.1 Experimental Procedure for the Synthesis of Boronate Ester C-7a (Method I)

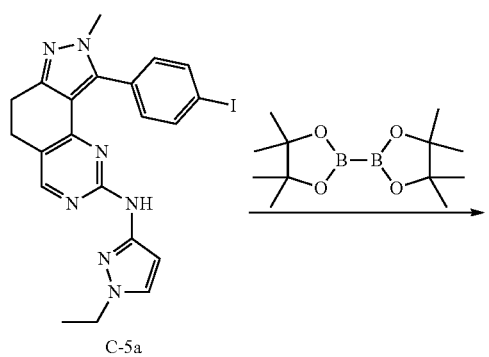

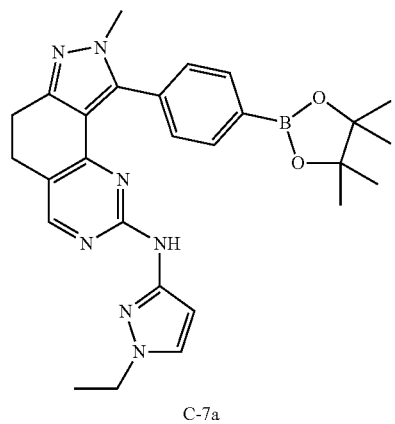

To C-5a (1.75 g, 3.52 mmol) in dry dioxane (5 mL)/dry methanol (5 mL) are added cesium acetate (850 mg, 4.43 mmol), 1,1'-bis(di-t-butylphosphino)ferrocene palladium dichloride (40 mg, 61 μmol) and bis(pinacolato)diboron (1.0 g, 3.94 mmol) and stirred for 20 min at 125° C. in a microwave reactor under an argon atmosphere. The product is isolated either by precipitation or by extraction. The crude product is purified by flash chromatography or crystallization if necessary.

Boronate ester C-7b (table 10) and further boronate esters can be obtained in an analogous manner with different intermediates C-5.

TABLE 10

| # | Structure | $t_{ret}$ [min] | $[M + H]^+$ | HPLC method |
|---|-----------|-----------------|-------------|-------------|
| C-7a | 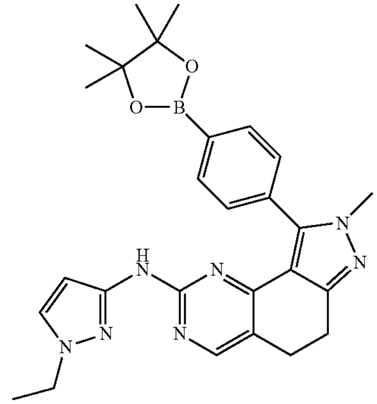 [SMILES: CCn1ccc(Nc2ncc3c(n2)-c2c(nn(C)c2-c2ccc(B4OC(C)(C)C(C)(C)O4)cc2)CC3)n1] | 1.38 | 498 | A |

TABLE 10-continued

| # | Structure | t_ret [min] | [M + H]+ | HPLC method |
|---|-----------|-------------|----------|-------------|
| C-7b | 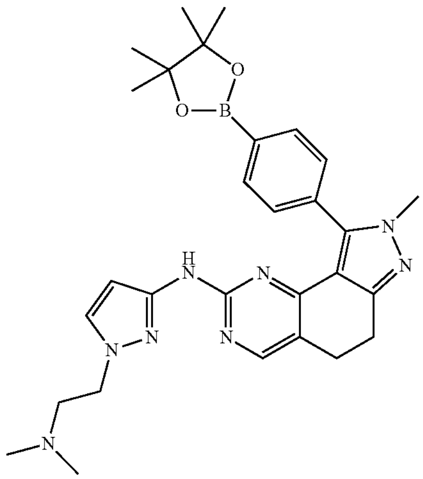 | 0.45 | 541 | B |

C.3.2.2 Synthesis of Example Compounds (I) by "Inverted" Suzuki Coupling (Method F)

Boronate ester C-7a and analogous intermediates C-7 are reacted with appropriate (hetero)aryl halides C-8 under the conditions described in method F (table 11). Compounds for biological testing are purified by prep. HPCL-MS.

TABLE 11

| # | Structure | t_ret [min] | M + H+ | HPLC method |
|---|-----------|-------------|--------|-------------|
| I-42 | 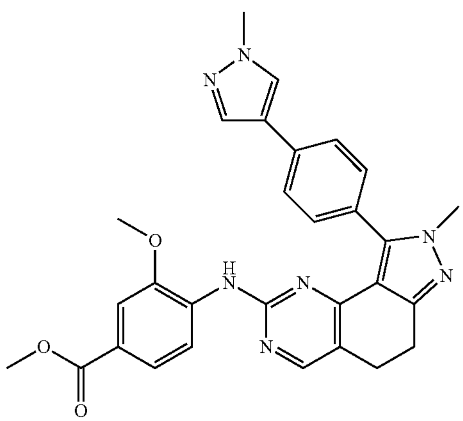 | 1.25 | 522 | A |
| I-43 | 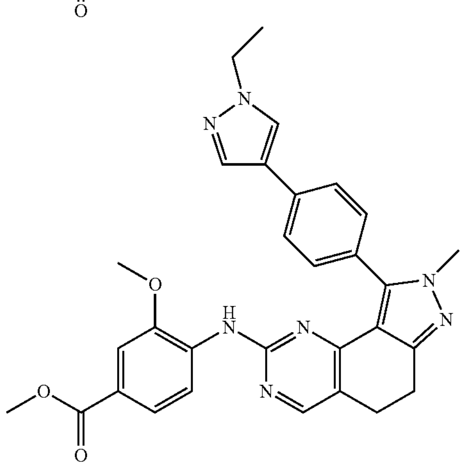 | 0.71 | 536 | B |

TABLE 11-continued

| # | Structure | $t_{ret}$ [min] | M + H⁺ | HPLC method |
|---|---|---|---|---|
| I-44 | 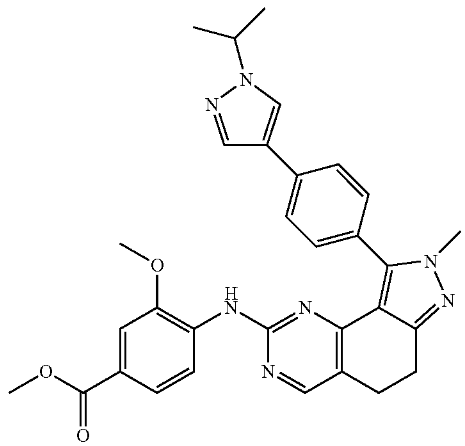 | 0.76 | 550 | B |
| I-45 | 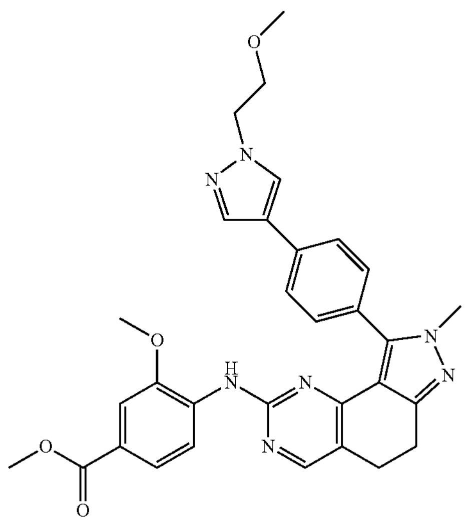 | 0.68 | 566 | B |
| I-46 | 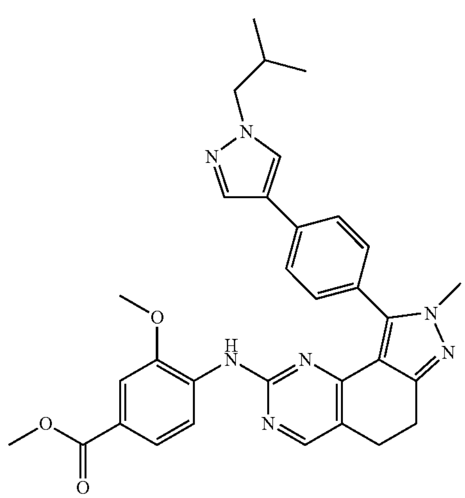 | 0.81 | 564 | B |

TABLE 11-continued

| # | Structure | $t_{ret}$ [min] | M + H⁺ | HPLC method |
|---|---|---|---|---|
| I-47 | 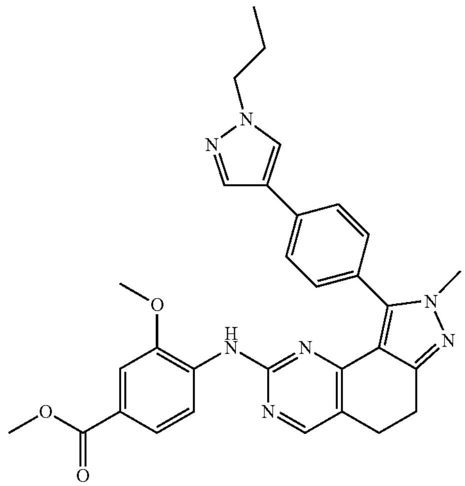 | 0.77 | 550 | B |
| I-48 | 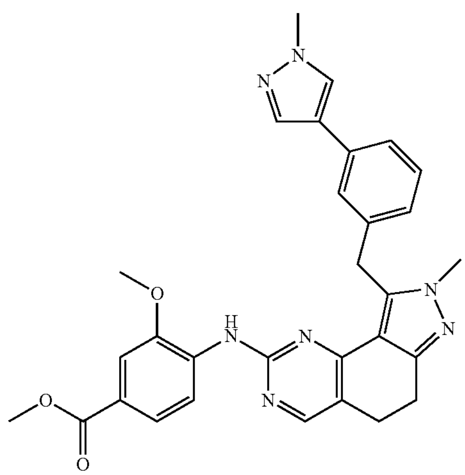 | 0.70 | 536 | B |
| I-49 | 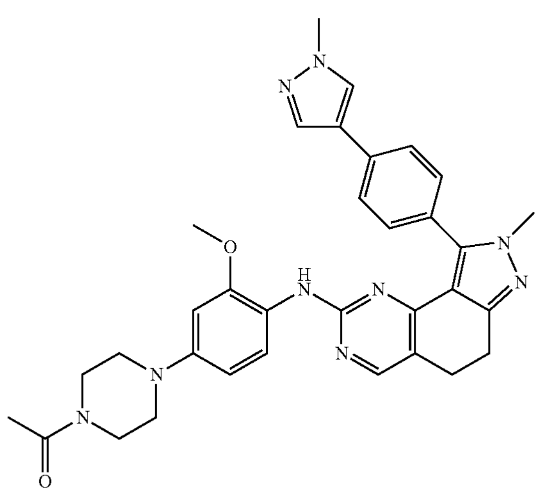 [SMILES: COc1cc(N2CCN(C(C)=O)CC2)ccc1Nc1ncc2c(n1)-c1c(nn(C)c1-c1ccc(-c3cnn(C)c3)cc1)CC2] | 0.45 | 590 | B |

TABLE 11-continued

| # | Structure | t_ret [min] | M + H+ | HPLC method |
|---|---|---|---|---|
| I-50 | 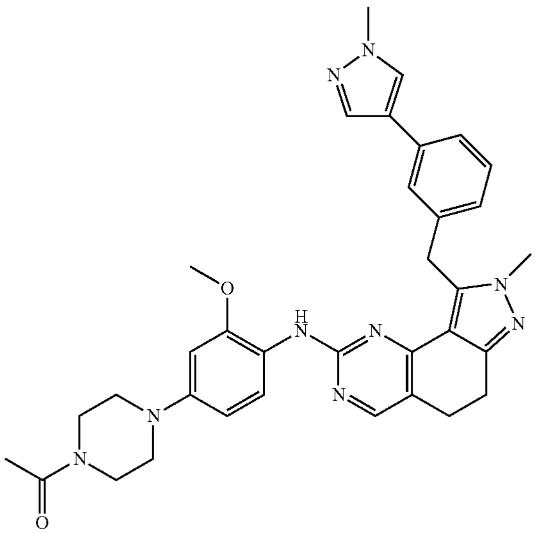 [SMILES: COc1cc(N2CCN(C(C)=O)CC2)ccc1Nc1ncc2c(n1)-c1c(nn(C)c1Cc1cccc(-c3cnn(C)c3)c1)CC2] | 0.48 | 604 | B |
| I-51 | 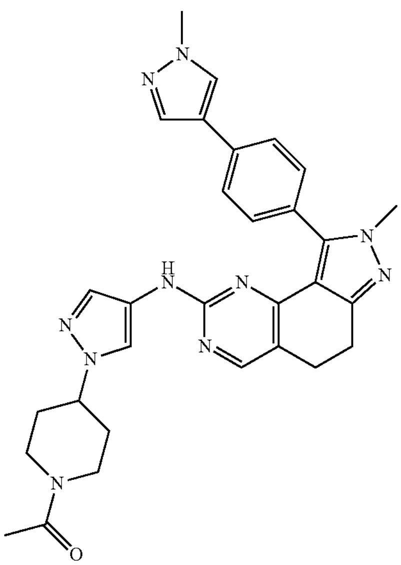 [SMILES: CC(=O)N1CCC(n2cc(Nc3ncc4c(n3)-c3c(nn(C)c3-c3ccc(-c5cnn(C)c5)cc3)CC4)cn2)CC1] | 0.37 | 549 | B |
| I-52[6] | 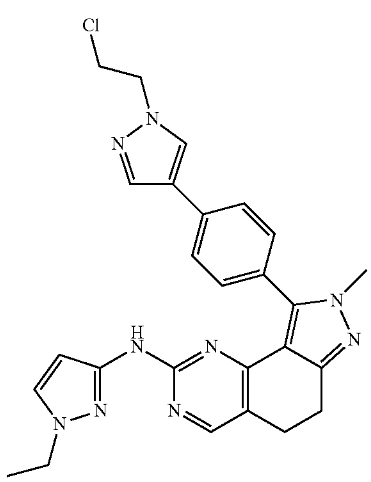 [SMILES: CCn1ccc(Nc2ncc3c(n2)-c2c(nn(C)c2-c2ccc(-c4cnn(CCCl)c4)cc2)CC3)n1] | 1.03 | 500 | A |

TABLE 11-continued

| # | Structure | $t_{ret}$ [min] | M + H⁺ | HPLC method |
|---|---|---|---|---|
| I-53 | 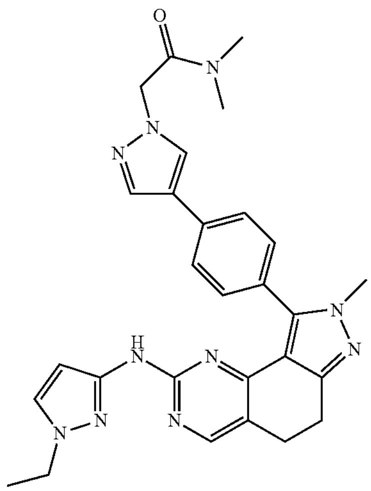 [SMILES: CCn1ccc(Nc2ncc3c(n2)-c2c(nn(C)c2-c2ccc(-c4cnn(CC(=O)N(C)C)c4)cc2)CC3)n1] | 1.15 | 523 | E |
| I-54 | 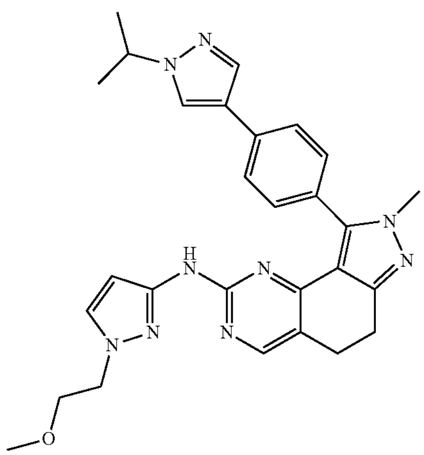 | 1.26 | 510 | E |
| I-55 | 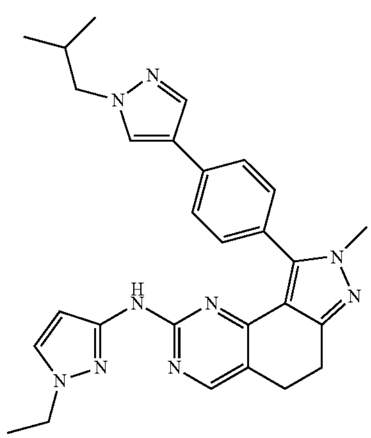 [SMILES: CCn1ccc(Nc2ncc3c(n2)-c2c(nn(C)c2-c2ccc(-c4cnn(CC(C)C)c4)cc2)CC3)n1] | 1.35 | 494 | E |

TABLE 11-continued

| # | Structure | $t_{ret}$ [min] | M + H$^+$ | HPLC method |
|---|---|---|---|---|
| I-56 | 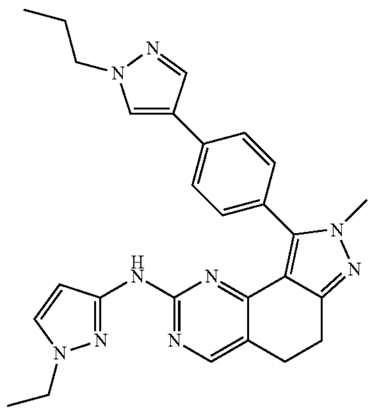 [SMILES: CCCn1cc(-c2ccc(-c3c4c(nn3C)CCc3cnc(Nc5ccn(CC)n5)nc3-4)cc2)cn1] | 1.30 | 480 | E |
| I-57 | 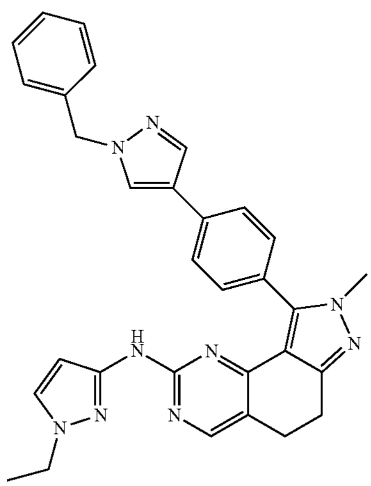 [SMILES: CCn1ccc(Nc2ncc3c(n2)-c2c(nn(C)c2-c2ccc(-c4cnn(Cc5ccccc5)c4)cc2)CC3)n1] | 1.36 | 528 | E |
| I-58 | 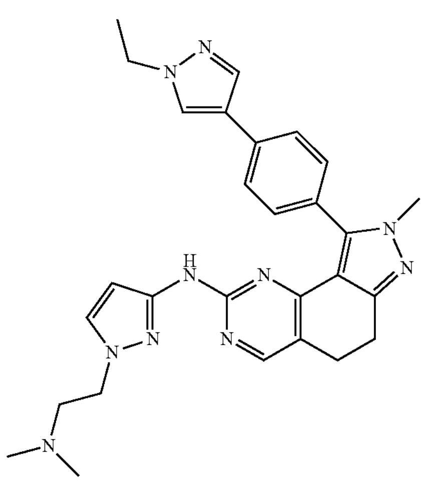 | 1.21 | 509 | E |

TABLE 11-continued

| # | Structure | $t_{ret}$ [min] | M + H⁺ | HPLC method |
|---|---|---|---|---|
| I-59 | 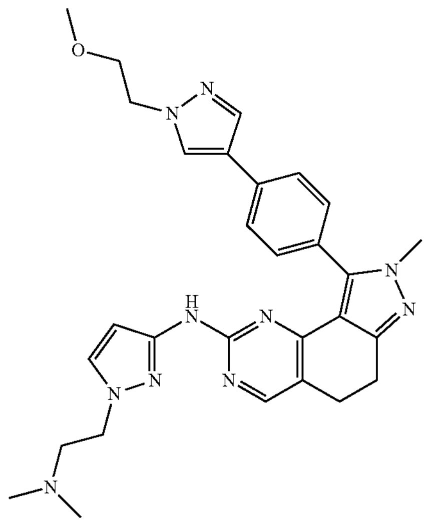 | 1.18 | 539 | E |
| I-60 | 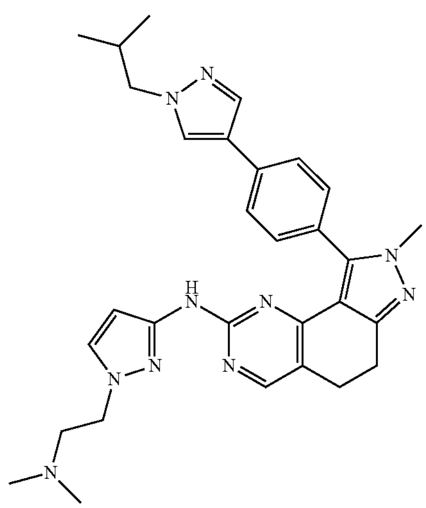 | 1.33 | 537 | E |
| I-61 | 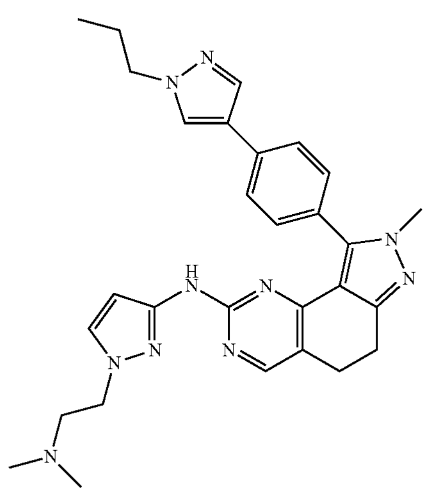 | 1.26 | 523 | E |

TABLE 11-continued
| # | Structure | $t_{ret}$ [min] | M + H⁺ | HPLC method |
|---|---|---|---|---|
| I-62 | 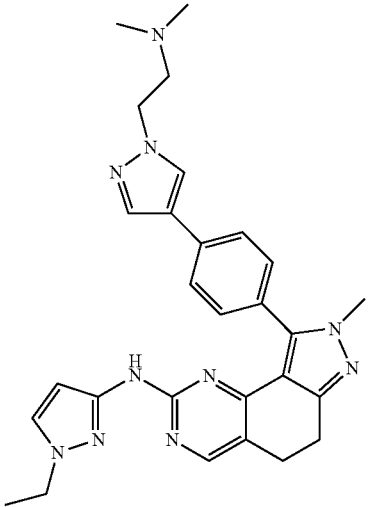 [SMILES: CCn1ccc(Nc2ncc3c(n2)-c2c(nn(C)c2-c2ccc(-c4cnn(CCN(C)C)c4)cc2)CC3)n1] | 1.20 | 509 | E |
| I-63 | 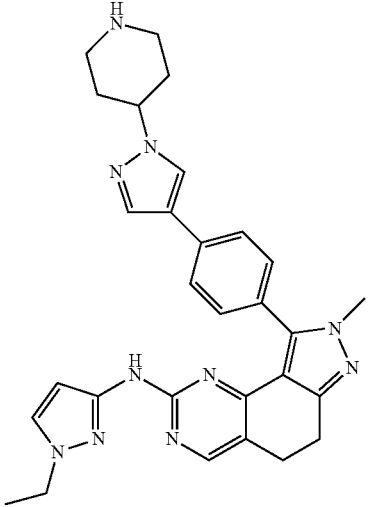 [SMILES: CCn1ccc(Nc2ncc3c(n2)-c2c(nn(C)c2-c2ccc(-c4cnn(C5CCNCC5)c4)cc2)CC3)n1] | 1.17 | 521 | E |
| I-64 | 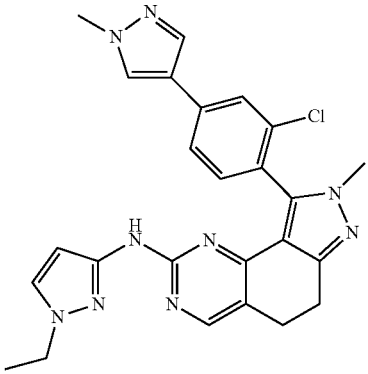 [SMILES: CCn1ccc(Nc2ncc3c(n2)-c2c(nn(C)c2-c2ccc(-c4cnn(C)c4)cc2Cl)CC3)n1] | 1.19 | 486/488 | E |

TABLE 11-continued

| # | Structure | $t_{ret}$ [min] | M + H⁺ | HPLC method |
|---|---|---|---|---|
| I-65 | 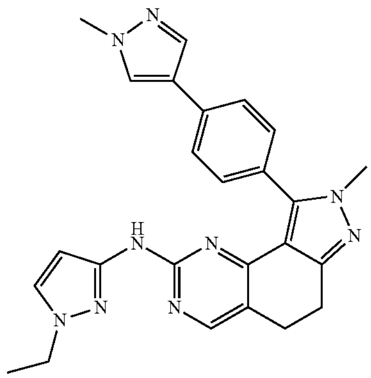 [SMILES: CCn1ccc(Nc2ncc3c(n2)-c2c(nn(C)c2-c2ccc(-c4cnn(C)c4)cc2)CC3)n1] | 1.16 | 452 | E |
| I-66 | 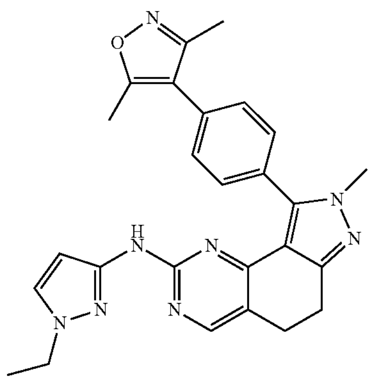 [SMILES: CCn1ccc(Nc2ncc3c(n2)-c2c(nn(C)c2-c2ccc(-c4c(C)noc4C)cc2)CC3)n1] | 1.27 | 467 | E |
| I-67 | 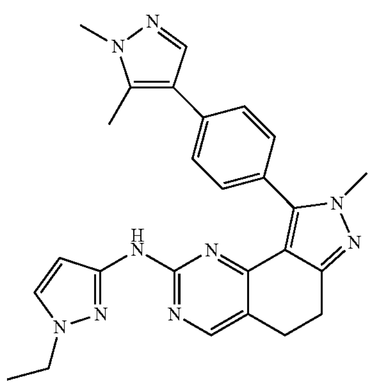 [SMILES: CCn1ccc(Nc2ncc3c(n2)-c2c(nn(C)c2-c2ccc(-c4cnn(C)c4C)cc2)CC3)n1] | 1.19 | 466 | E |
| I-68 | 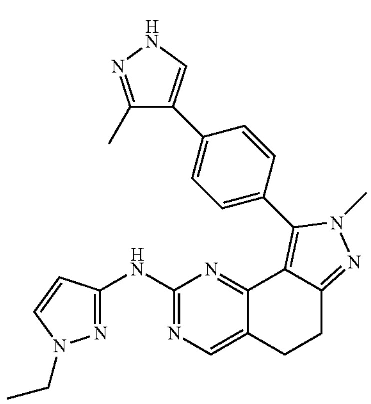 [SMILES: CCn1ccc(Nc2ncc3c(n2)-c2c(nn(C)c2-c2ccc(-c4c[nH]nc4C)cc2)CC3)n1] | 1.17 | 452 | E |

TABLE 11-continued

| # | Structure | $t_{ret}$ [min] | M + H⁺ | HPLC method |
|---|---|---|---|---|
| I-69 | 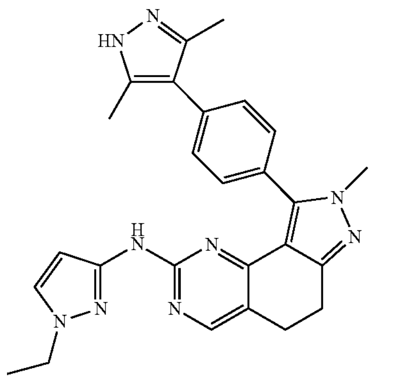 [SMILES: CCn1ccc(Nc2ncc3c(n2)-c2c(nn(C)c2-c2ccc(-c4c(C)n[nH]c4C)cc2)CC3)n1] | 1.14 | 466 | E |
| I-70 | 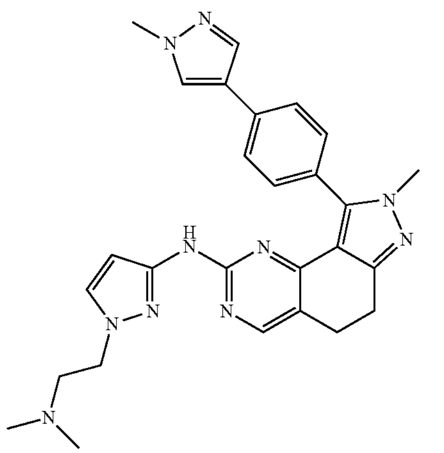 | 1.14 | 495 | E |
| I-71 | 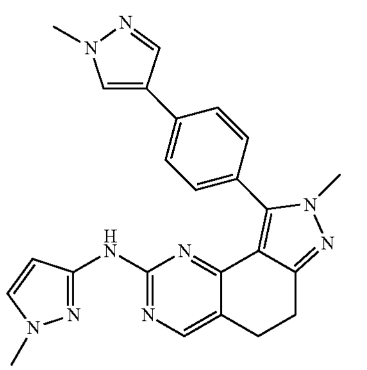 [SMILES: Cn1cc(-c2ccc(-c3c4c(nn3C)CCc3cnc(Nc5ccn(C)n5)nc3-4)cc2)cn1] | 1.12 | 438 | E |
| I-72 | 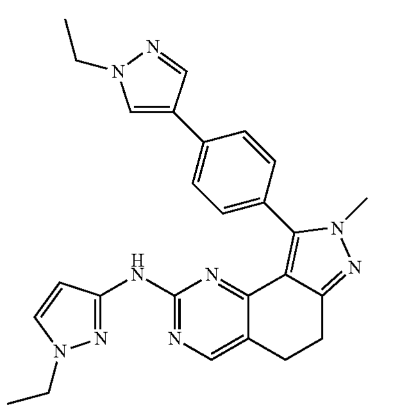 [SMILES: CCn1cc(-c2ccc(-c3c4c(nn3C)CCc3cnc(Nc5ccn(CC)n5)nc3-4)cc2)cn1] | 1.23 | 466 | E |

TABLE 11-continued

| # | Structure | $t_{ret}$ [min] | M + H⁺ | HPLC method |
|---|---|---|---|---|
| I-73 | 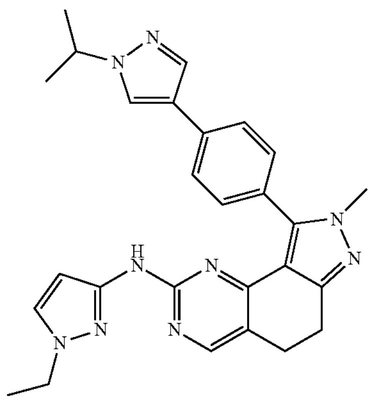 [SMILES: CCn1ccc(Nc2ncc3c(n2)-c2c(nn(C)c2-c2ccc(-c4cnn(C(C)C)c4)cc2)CC3)n1] | 1.29 | 480 | E |
| I-74 | 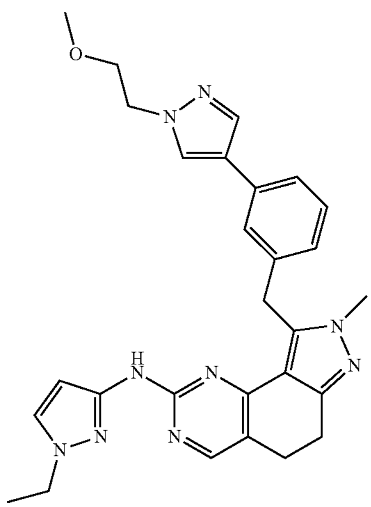 [SMILES: CCn1ccc(Nc2ncc3c(n2)-c2c(nn(C)c2Cc2cccc(-c4cnn(CCOC)c4)c2)CC3)n1] | 1.70 | 510 | E |
| I-75 | 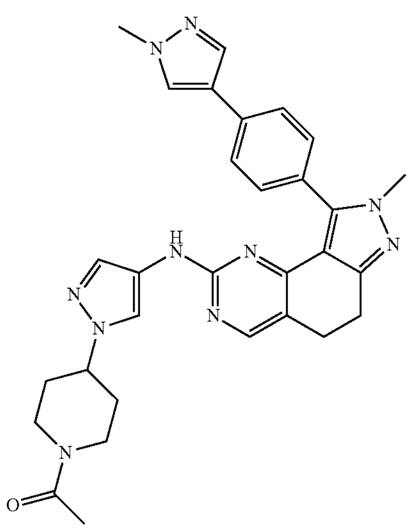 [SMILES: CC(=O)N1CCC(n2cc(Nc3ncc4c(n3)-c3c(nn(C)c3-c3ccc(-c5cnn(C)c5)cc3)CC4)cn2)CC1] | 1.12 | 549 | E |

TABLE 11-continued

| # | Structure | t_ret [min] | M + H+ | HPLC method |
|---|---|---|---|---|
| I-76 | 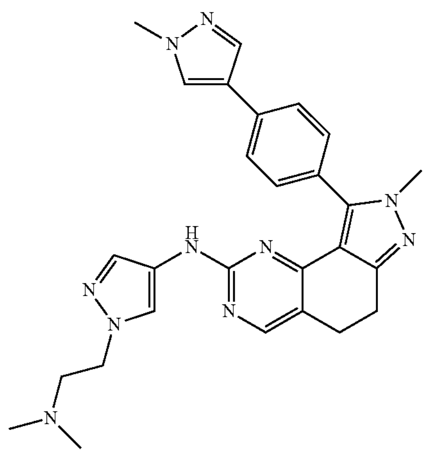 | 1.15 | 495 | E |
| I-77 | 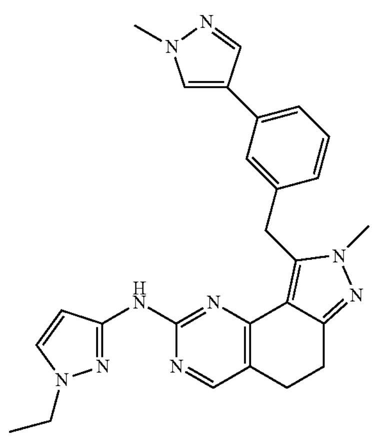 [SMILES: CCn1ccc(Nc2ncc3c(n2)-c2c(nn(C)c2Cc2cccc(-c4cnn(C)c4)c2)CC3)n1] | 1.21 | 466 | E |
| I-78 | 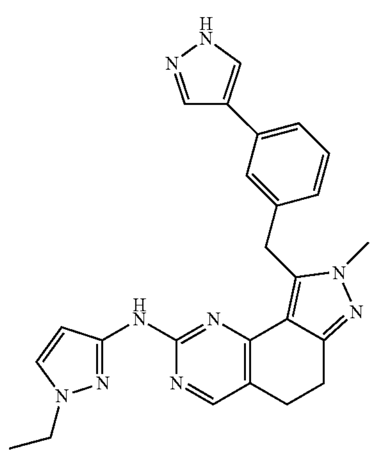 [SMILES: CCn1ccc(Nc2ncc3c(n2)-c2c(nn(C)c2Cc2cccc(-c4cn[nH]c4)c2)CC3)n1] | 1.19 | 452 | E |

TABLE 11-continued

| # | Structure | $t_{ret}$ [min] | M + H⁺ | HPLC method |
|---|---|---|---|---|
| I-79 | 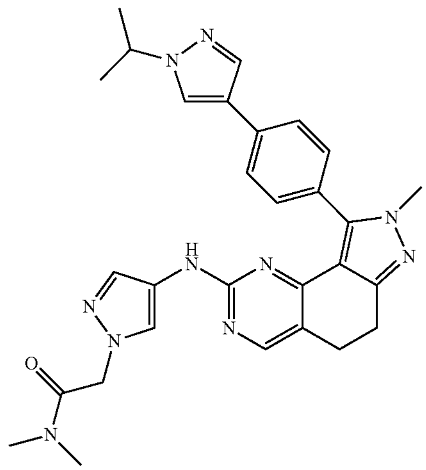 | 1.40 | 537 | E |
| I-80 | 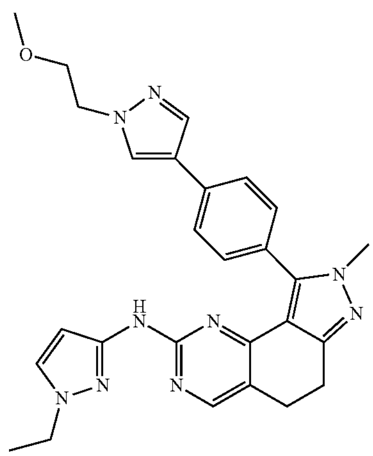 [SMILES: CCn1ccc(Nc2ncc3c(n2)-c2c(nn(C)c2-c2ccc(-c4cnn(CCOC)c4)cc2)CC3)n1] | 1.20 | 496 | E |
| I-81[7] | 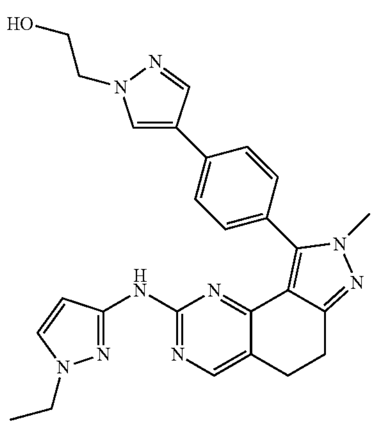 [SMILES: CCn1ccc(Nc2ncc3c(n2)-c2c(nn(C)c2-c2ccc(-c4cnn(CCO)c4)cc2)CC3)n1] | 1.14 | 482 | E |

TABLE 11-continued
| # | Structure | $t_{ret}$ [min] | M + H⁺ | HPLC method |
|---|---|---|---|---|
| I-82 | 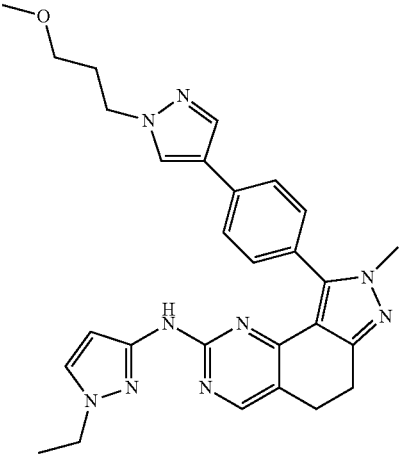 | 1.23 | 510 | E |
| I-83 | 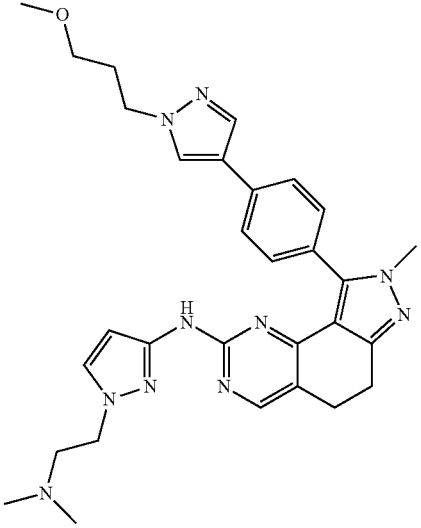 | 1.23 | 553 | E |
| I-84 | 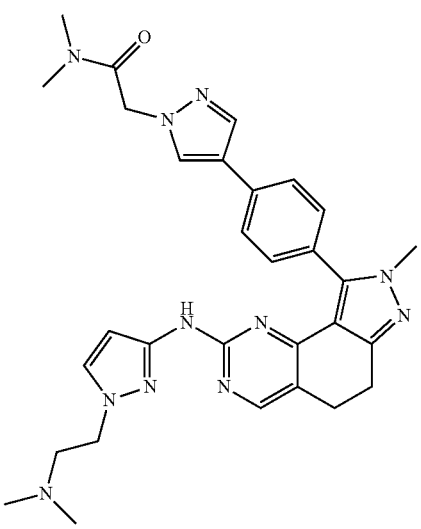 | 0.96 | 566 | E |

TABLE 11-continued

| # | Structure | $t_{ret}$ [min] | M + H$^+$ | HPLC method |
|---|-----------|-----------------|-----------|-------------|
| I-85 | 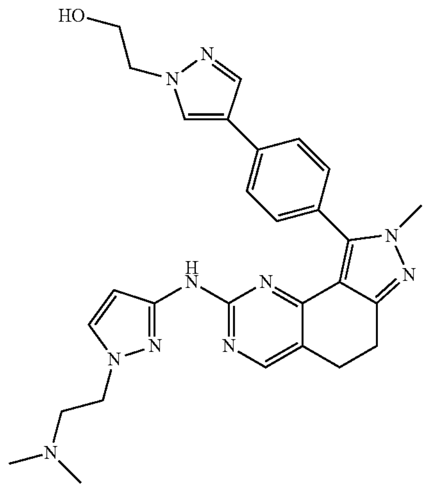 | 0.95 | 525 | E |
| I-86 | 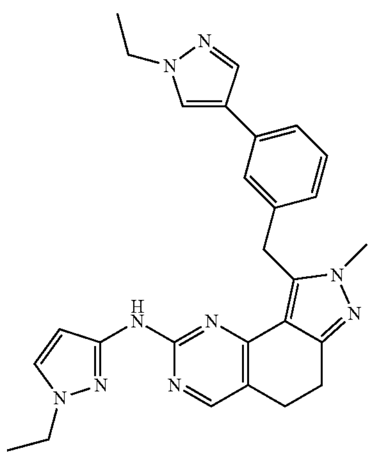 [SMILES: CCn1cc(-c2cccc(Cc3c4c(nn3C)CCc3cnc(Nc5ccn(CC)n5)nc3-4)c2)cn1] | 1.27 | 480 | E |
| I-87 | 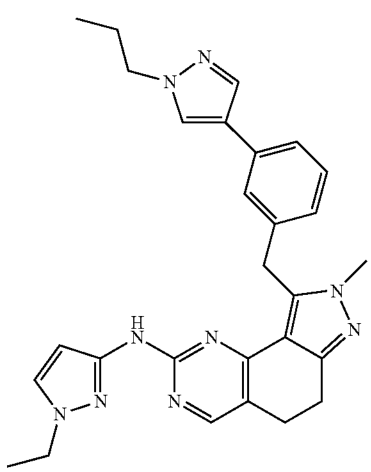 [SMILES: CCCn1cc(-c2cccc(Cc3c4c(nn3C)CCc3cnc(Nc5ccn(CC)n5)nc3-4)c2)cn1] | 1.33 | 494 | E |

TABLE 11-continued

| # | Structure | $t_{ret}$ [min] | M + H⁺ | HPLC method |
|---|---|---|---|---|
| I-88 | 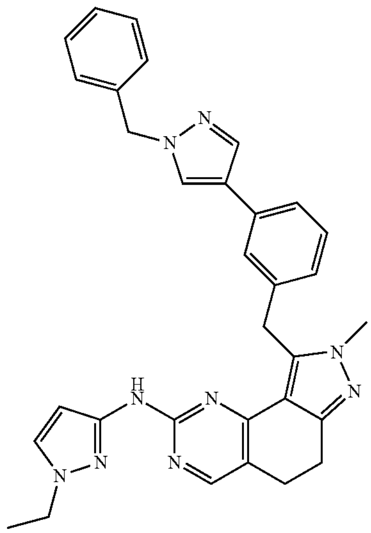 [SMILES: CCn1ccc(Nc2ncc3c(n2)-c2c(nn(C)c2Cc2cccc(-c4cnn(Cc5ccccc5)c4)c2)CC3)n1] | 1.40 | 542 | E |
| I-89 | 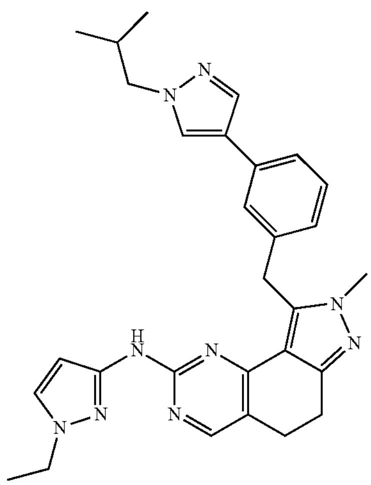 [SMILES: CCn1ccc(Nc2ncc3c(n2)-c2c(nn(C)c2Cc2cccc(-c4cnn(CC(C)C)c4)c2)CC3)n1] | 1.39 | 508 | E |
| I-90 | 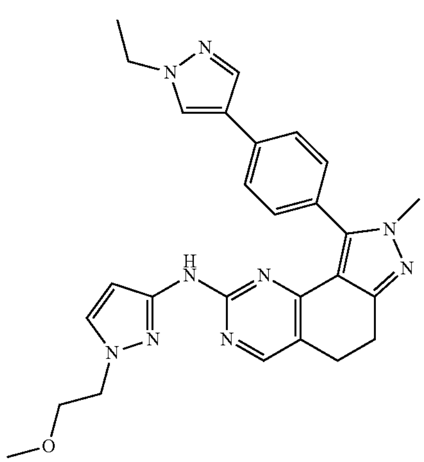 | 1.05 | 496 | E |

TABLE 11-continued
| # | Structure | $t_{ret}$ [min] | M + H⁺ | HPLC method |
|---|---|---|---|---|
| I-91 | 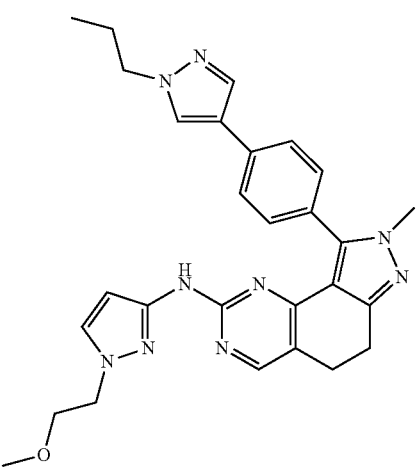 | 1.11 | 510 | E |
| I-92 | 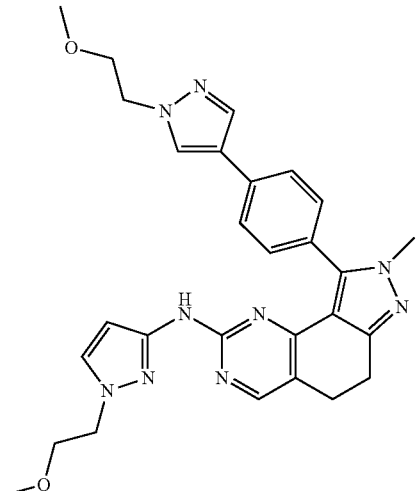 | 1.02 | 526 | E |
| I-93[8] | 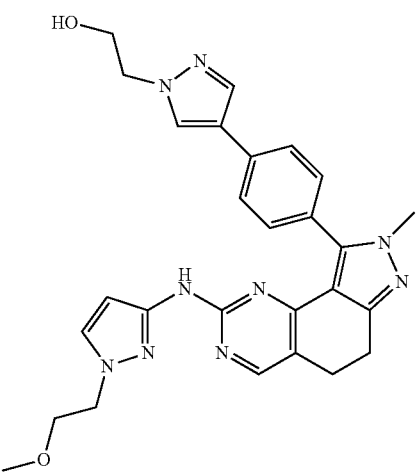 | 0.92 | 512 | E |

TABLE 11-continued

| # | Structure | t_ret [min] | M + H+ | HPLC method |
|---|---|---|---|---|
| I-94 | 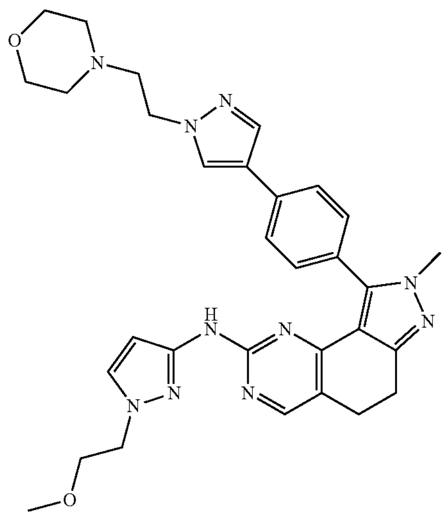 [SMILES: COCCn1ccc(Nc2ncc3c(n2)-c2c(nn(C)c2-c2ccc(-c4cnn(CCN5CCOCC5)c4)cc2)CC3)n1] | 1.00 | 581 | E |
| I-95 | 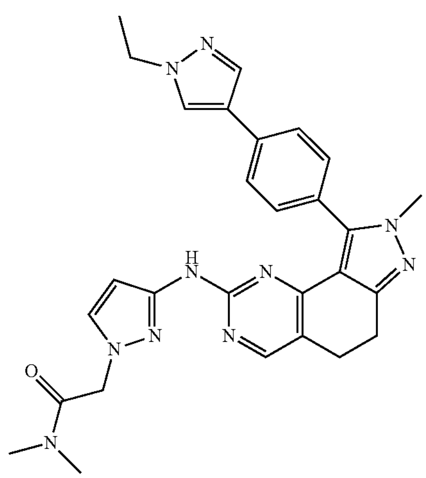 | 0.98 | 523 | E |
| I-96 | 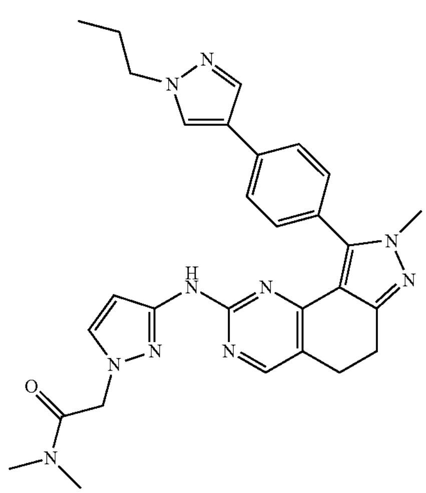 | 1.04 | 537 | E |

TABLE 11-continued
| # | Structure | $t_{ret}$ [min] | M + H⁺ | HPLC method |
|---|---|---|---|---|
| I-97 | 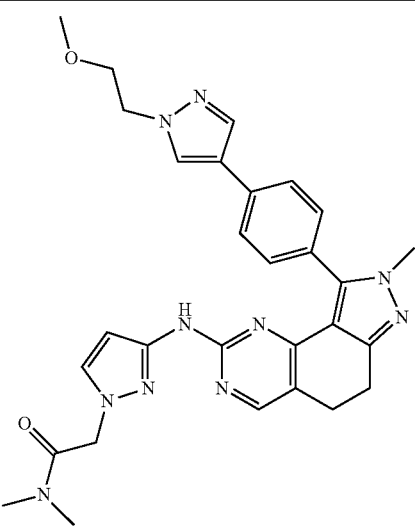 | 0.95 | 553 | E |
| I-98 | 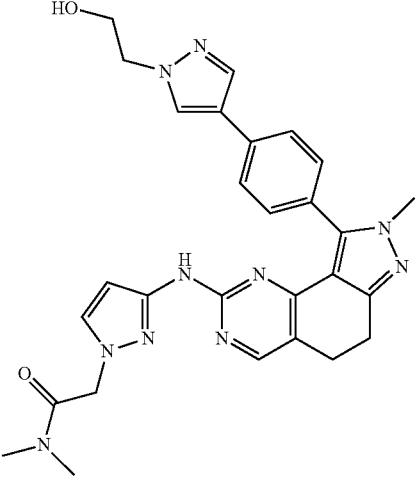 | 0.87 | 539 | E |
| I-99 | 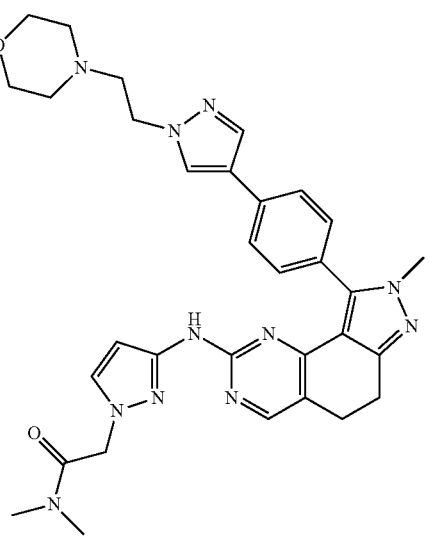 | 0.94 | 608 | E |

TABLE 11-continued
| # | Structure | $t_{ret}$ [min] | M + H⁺ | HPLC method |
|---|---|---|---|---|
| I-100* | 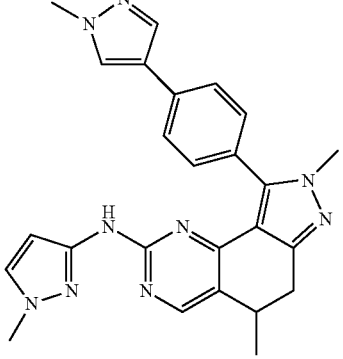 | 1.02 | 452 | E |
| I-101* | 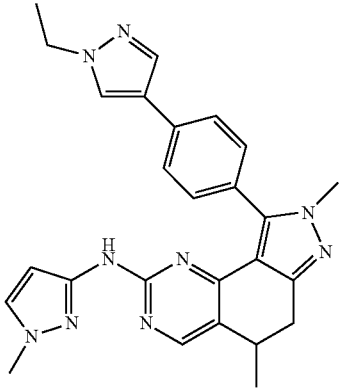 [SMILES: CCn1cc(-c2ccc(-c3c4c(nn3C)CC(C)c3cnc(Nc5ccn(C)n5)nc3-4)cc2)cn1] | 1.09 | 466 | E |
| I-102* | 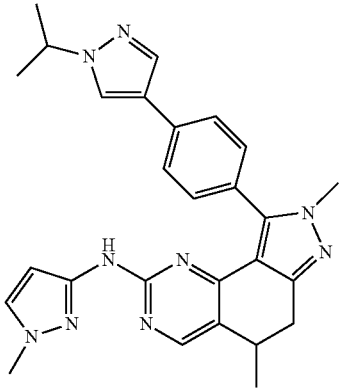 [SMILES: CC1Cc2nn(C)c(-c3ccc(-c4cnn(C(C)C)c4)cc3)c2-c2nc(Nc3ccn(C)n3)ncc21] | 1.14 | 480 | E |
| I-103* | 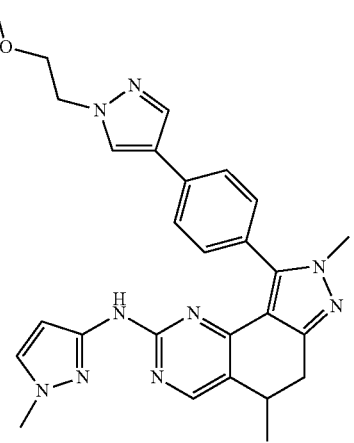 | 1.05 | 496 | E |

TABLE 11-continued

| # | Structure | $t_{ret}$ [min] | M + H⁺ | HPLC method |
|---|---|---|---|---|
| I-104 | 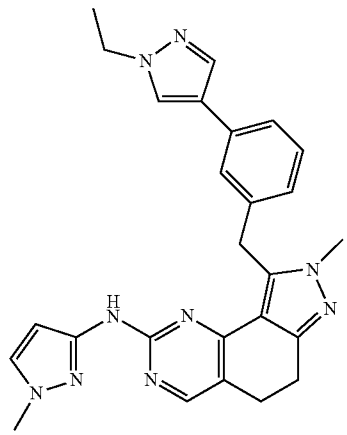 [SMILES: CCn1cc(-c2cccc(Cc3c4c(nn3C)CCc3cnc(Nc5ccn(C)n5)nc3-4)c2)cn1] | 1.06 | 466 | E |
| I-105 | 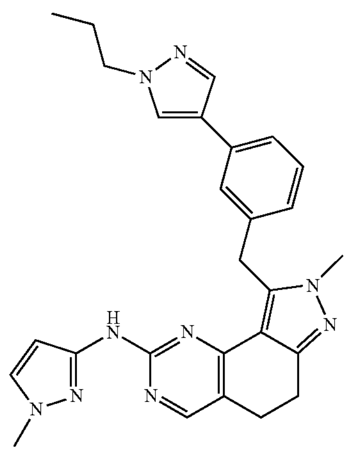 [SMILES: CCCn1cc(-c2cccc(Cc3c4c(nn3C)CCc3cnc(Nc5ccn(C)n5)nc3-4)c2)cn1] | 1.12 | 480 | E |
| I-106 | 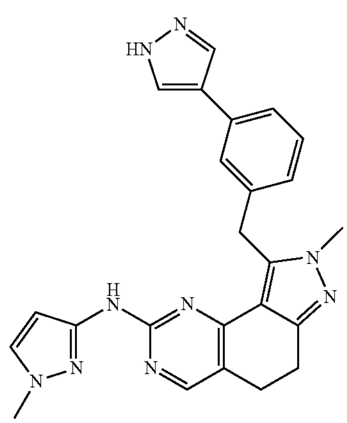 [SMILES: Cn1ccc(Nc2ncc3c(n2)-c2c(nn(C)c2Cc2cccc(-c4cn[nH]c4)c2)CC3)n1] | 0.95 | 438 | E |

TABLE 11-continued

| # | Structure | $t_{ret}$ [min] | M + H⁺ | HPLC method |
|---|---|---|---|---|
| I-107 | 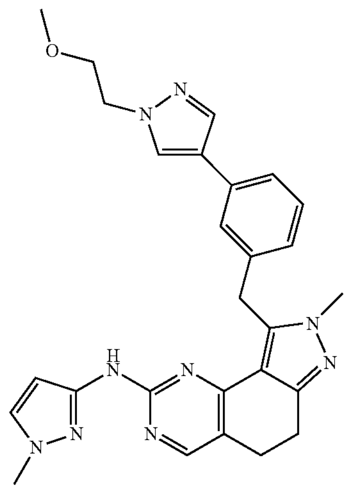 [SMILES: COCCn1cc(-c2cccc(Cc3c4c(nn3C)CCc3cnc(Nc5ccn(C)n5)nc3-4)c2)cn1] | 1.03 | 496 | E |
| I-108 | 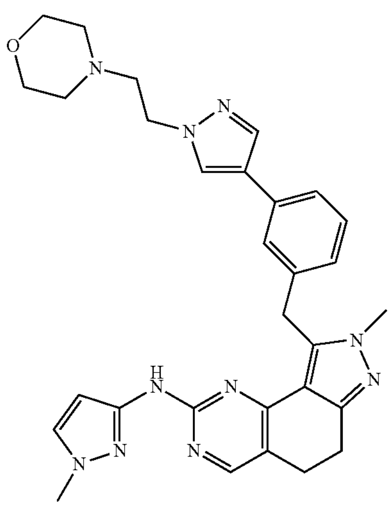 [SMILES: Cn1ccc(Nc2ncc3c(n2)-c2c(nn(C)c2Cc2cccc(-c4cnn(CCN5CCOCC5)c4)c2)CC3)n1] | 1.02 | 551 | E |
| I-109 | 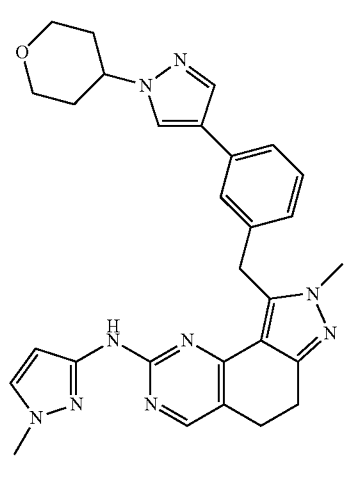 [SMILES: Cn1ccc(Nc2ncc3c(n2)-c2c(nn(C)c2Cc2cccc(-c4cnn(C5CCOCC5)c4)c2)CC3)n1] | 1.05 | 552 | E |

TABLE 11-continued

| # | Structure | $t_{ret}$ [min] | M + H⁺ | HPLC method |
|---|---|---|---|---|
| I-110[9] | 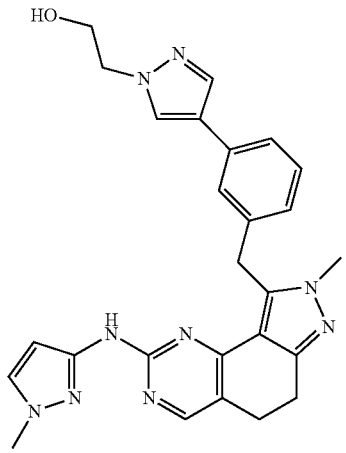 [SMILES: Cn1ccc(Nc2ncc3c(n2)-c2c(nn(C)c2Cc2cccc(-c4cnn(CCO)c4)c2)CC3)n1] | 0.94 | 482 | E |
| I-111 | 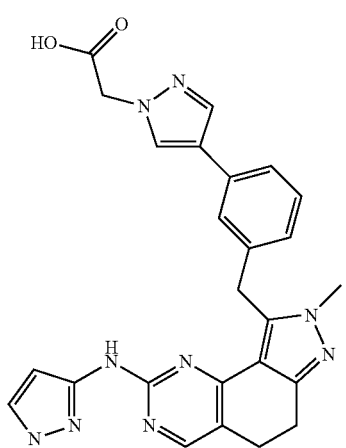 | 0.79 | 496 | E |

[6]also obtainable from I-81 via chlorination

[7]also obtainable via SUZUKI coupling of 2-[4-(4,4,5,5-tetramethyl-1,3,2-dioxaborolan-2-yl]pyrazol-1-yl]ethyl acetate and C-5a (acetyl is cleaved off under coupling conditions of method F)

[8]also obtainable via SUZUKI coupling of 2-[4-(4,4,5,5-tetramethyl-1,3,2-dioxaborolan-2-yl)pyrazol-1-yl]ethyl acetate and C-5e (acetyl is cleaved off under coupling conditions of method F)

*racemic formula encompasses both enantiomers

[9]also obtainable via SUZUKI coupling of 2-[4-(4,4,5,5-tetramethyl-1,3,2-dioxaborolan-2-yl)pyrazol-1-yl]ethyl acetate and C-5c (acetyl is cleaved off under coupling conditions of method F)

145

D. Synthesis of Further Example Compounds (I) by Derivatization of Example Compounds (I)

D.1. Amination by Nucleophilic Substitution (Method J)

D.1.1. Experimental Procedure for the Synthesis of I-112

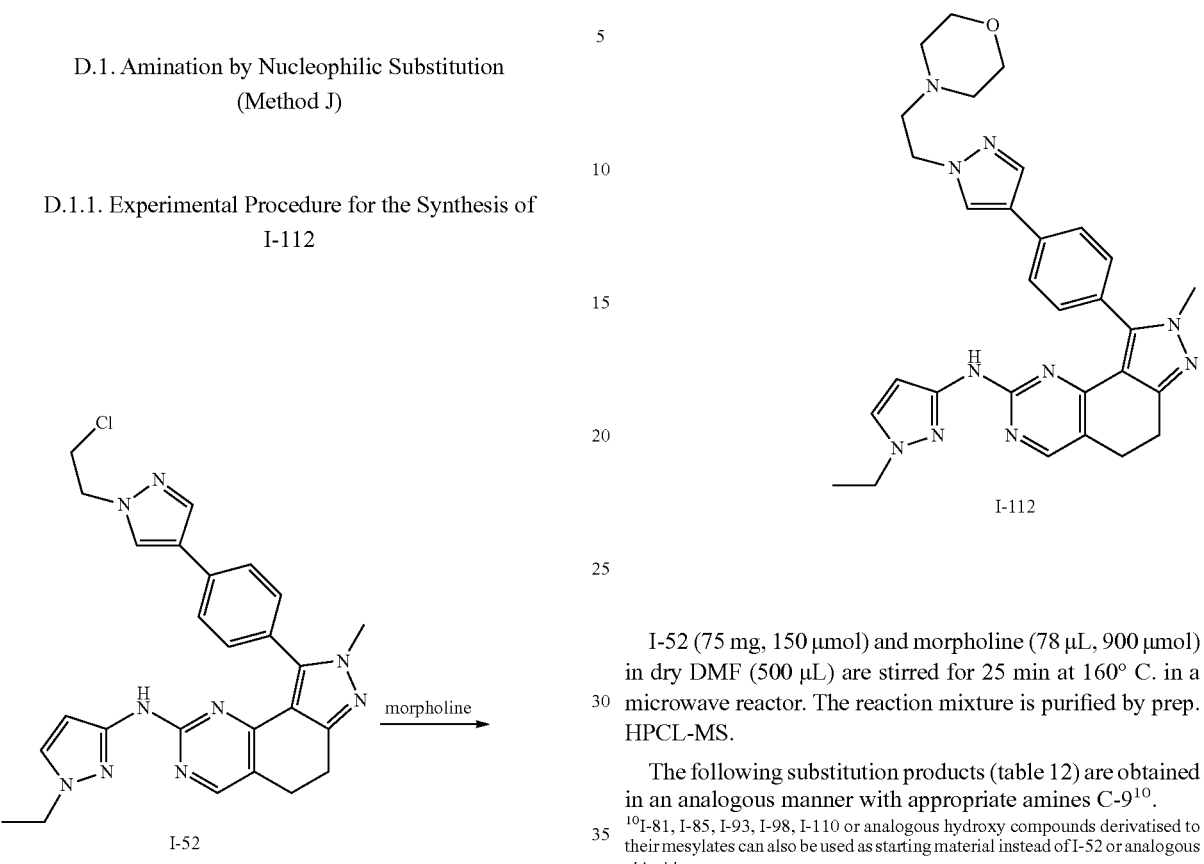

I-52 (75 mg, 150 μmol) and morpholine (78 μL, 900 μmol) in dry DMF (500 μL) are stirred for 25 min at 160° C. in a microwave reactor. The reaction mixture is purified by prep. HPCL-MS.

The following substitution products (table 12) are obtained in an analogous manner with appropriate amines C-9[10].

[10] I-81, I-85, I-93, I-98, I-110 or analogous hydroxy compounds derivatised to their mesylates can also be used as starting material instead of I-52 or analogous chlorides

TABLE 12

| # | Structure | $t_{ret}$ [min] | M + H⁺ | HPLC method |
|---|---|---|---|---|
| I-112 | 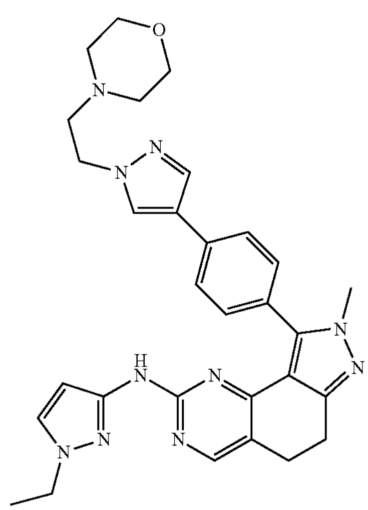 [SMILES: CCn1ccc(Nc2ncc3c(n2)-c2c(nn(C)c2-c2ccc(-c4cnn(CCN5CCOCC5)c4)cc2)CC3)n1] | 1.18 | 551 | E |

TABLE 12-continued
| # | Structure | t_ret [min] | M + H⁺ | HPLC method |
|---|---|---|---|---|
| I-113 | 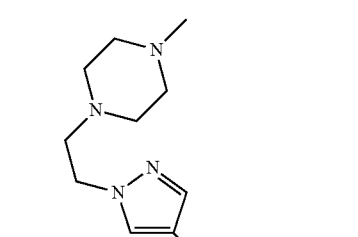 | 1.17 | 564 | E |
| I-114 | 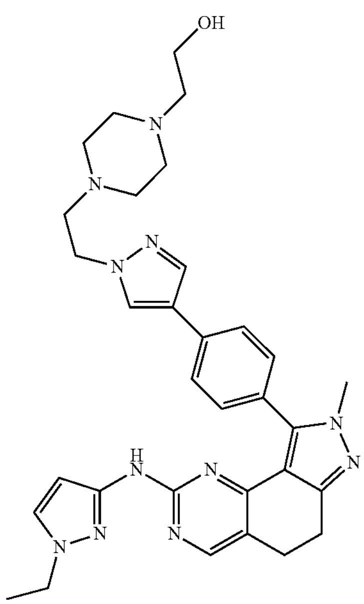 [SMILES: CCn1ccc(Nc2ncc3c(n2)-c2c(nn(C)c2-c2ccc(-c4cnn(CCN5CCN(CCO)CC5)c4)cc2)CC3)n1] | 1.11 | 594 | E |

TABLE 12-continued
| # | Structure | t_ret [min] | M + H+ | HPLC method |
|---|---|---|---|---|
| I-115 | 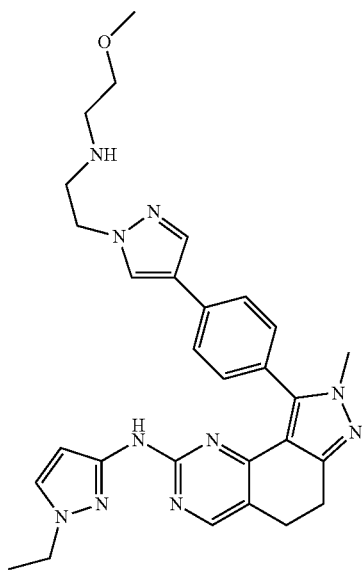 [SMILES: CCn1ccc(Nc2ncc3c(n2)-c2c(nn(C)c2-c2ccc(-c4cnn(CCNCCOC)c4)cc2)CC3)n1] | 1.16 | 539 | E |
| I-116 | 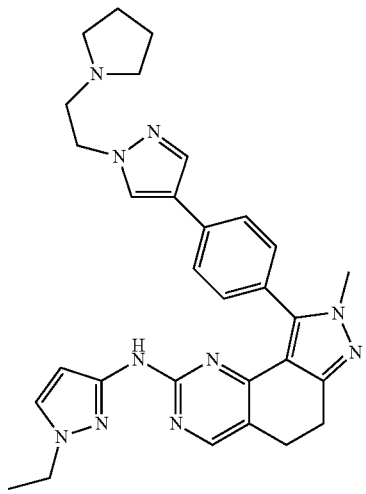 [SMILES: CCn1ccc(Nc2ncc3c(n2)-c2c(nn(C)c2-c2ccc(-c4cnn(CCN5CCCC5)c4)cc2)CC3)n1] | 1.27 | 535 | E |

TABLE 12-continued
| # | Structure | t_ret [min] | M + H⁺ | HPLC method |
|---|---|---|---|---|
| I-117 | 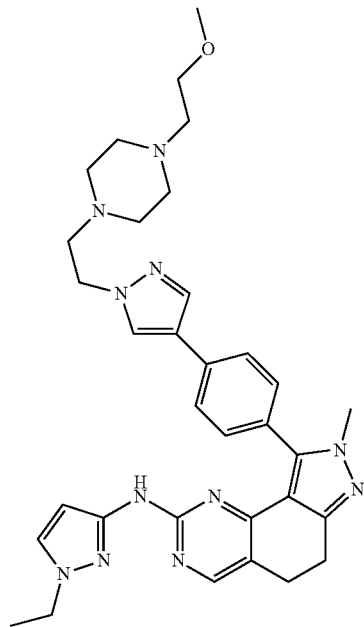 [SMILES: CCn1ccc(Nc2ncc3c(n2)-c2c(nn(C)c2-c2ccc(-c4cnn(CCN5CCN(CCOC)CC5)c4)cc2)CC3)n1] | 1.19 | 608 | E |
| I-118 | 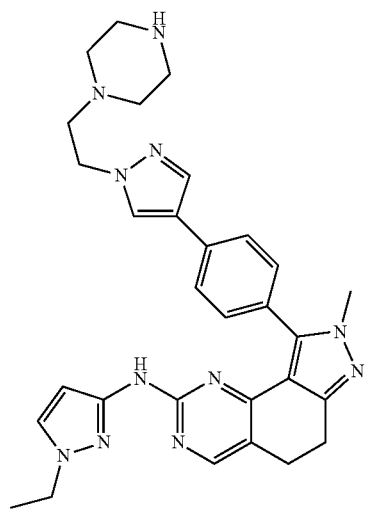 [SMILES: CCn1ccc(Nc2ncc3c(n2)-c2c(nn(C)c2-c2ccc(-c4cnn(CCN5CCNCC5)c4)cc2)CC3)n1] | 1.12 | 550 | E |

TABLE 12-continued
| # | Structure | t_ret [min] | M + H+ | HPLC method |
|---|---|---|---|---|
| I-119 | 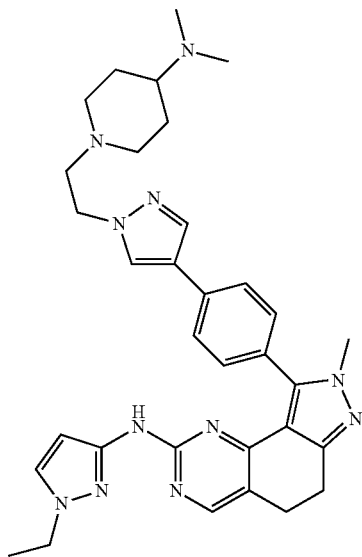 [SMILES: CCn1ccc(Nc2ncc3c(n2)-c2c(nn(C)c2-c2ccc(-c4cnn(CCN5CCC(N(C)C)CC5)c4)cc2)CC3)n1] | 1.25 | 592 | E |
| I-120 | 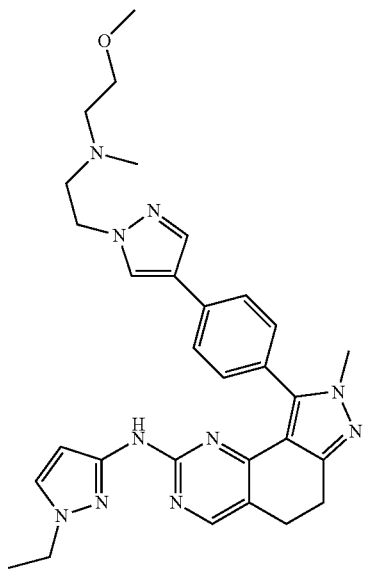 [SMILES: CCn1ccc(Nc2ncc3c(n2)-c2c(nn(C)c2-c2ccc(-c4cnn(CCN(C)CCOC)c4)cc2)CC3)n1] | 1.24 | 553 | E |

TABLE 12-continued
| # | Structure | t_ret [min] | M + H+ | HPLC method |
|---|---|---|---|---|
| I-190 | 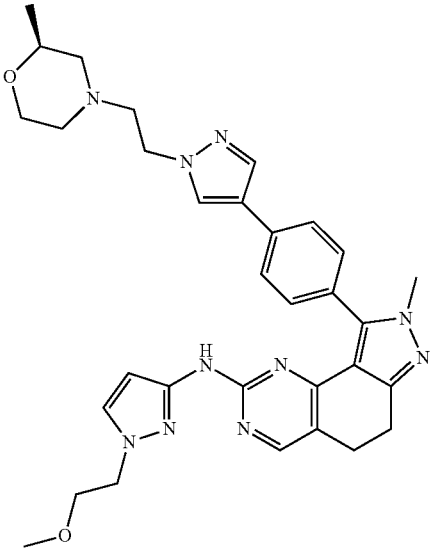 [SMILES: COCCn1ccc(Nc2ncc3c(n2)-c2c(nn(C)c2-c2ccc(-c4cnn(CCN5CCO[C@@H](C)C5)c4)cc2)CC3)n1] | 1.06 | 595 | E |
| I-191 | 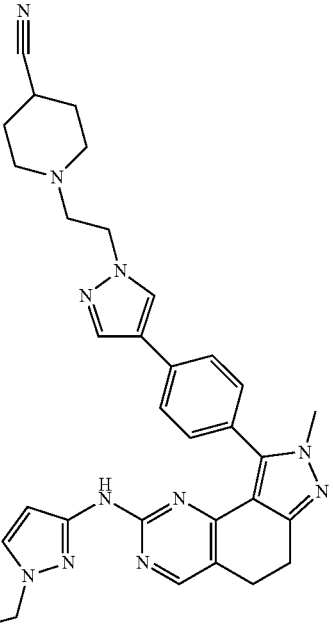 | 1.09 | 618 | E |

D.2. Ester Cleavage (Method K)

D.2.1. Experimental Procedure for the Synthesis of I-121

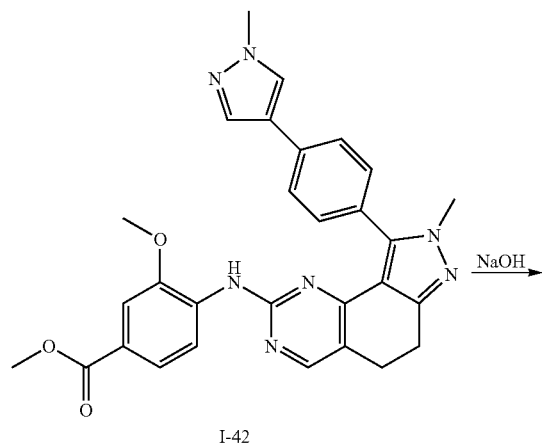

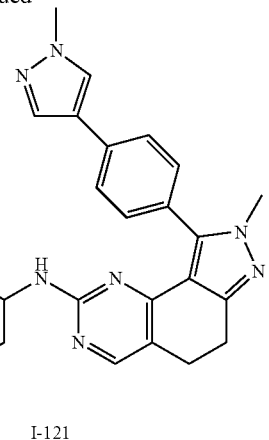

I-42 (2.08 g, 3.99 mmol) in MeOH (20 mL)/10 N NaOH (5 mL) is stirred for 4 d at 45° C. The pH of the reaction mixture is adjusted to 3 using 2 N HCl. The precipitate is collected by filtration, triturated with water and aq. EtOH repeatedly and dried in vacuo.

The following cleavage products (table 13) are obtained in an analogous manner.

TABLE 13

| # | Structure | $t_{ret}$ [min] | M + H⁺ | HPLC method |
|---|---|---|---|---|
| I-121 | 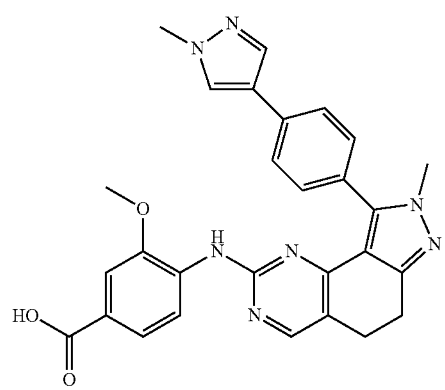 [SMILES: COc1cc(C(=O)O)ccc1Nc1ncc2c(n1)-c1c(nn(C)c1-c1ccc(-c3cnn(C)c3)cc1)CC2] | 1.15 | 508 | E |
| I-122 | 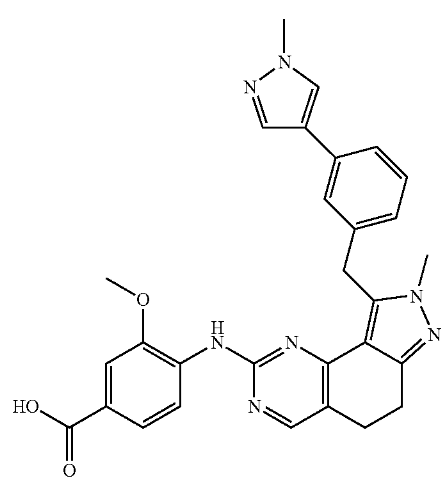 [SMILES: COc1cc(C(=O)O)ccc1Nc1ncc2c(n1)-c1c(nn(C)c1Cc1cccc(-c3cnn(C)c3)c1)CC2] | 0.56 | 522 | B |

TABLE 13-continued

| # | Structure | t_ret [min] | M + H+ | HPLC method |
|---|---|---|---|---|
| I-123 | 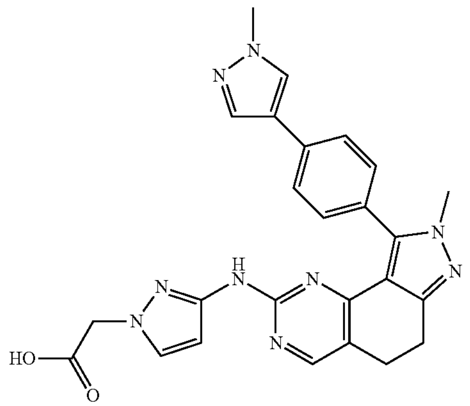 [SMILES: Cn1cc(-c2ccc(-c3c4c(nn3C)CCc3cnc(Nc5ccn(CC(=O)O)n5)nc3-4)cc2)cn1] | 0.38 | 482 | B |
| I-124 | 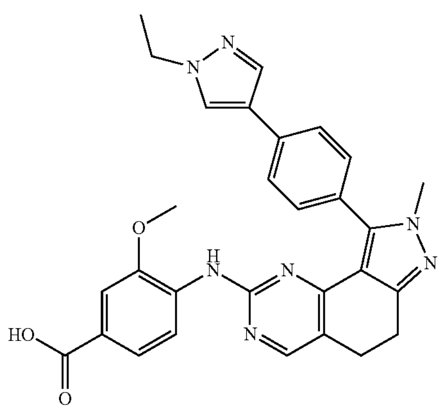 [SMILES: CCn1cc(-c2ccc(-c3c4c(nn3C)CCc3cnc(Nc5ccc(C(=O)O)cc5OC)nc3-4)cc2)cn1] | 1.20 | 522 | E |
| I-125 | 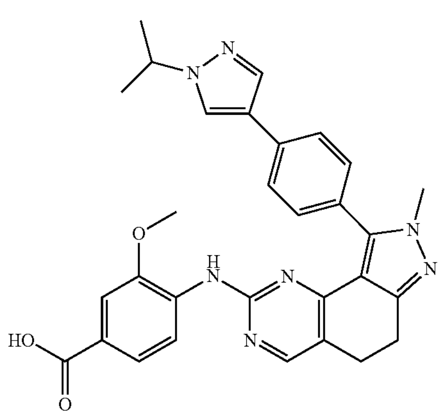 [SMILES: COc1cc(C(=O)O)ccc1Nc1ncc2c(n1)-c1c(nn(C)c1-c1ccc(-c3cnn(C(C)C)c3)cc1)CC2] | 1.23 | 536 | E |

TABLE 13-continued
| # | Structure | $t_{ret}$ [min] | M + H⁺ | HPLC method |
|---|---|---|---|---|
| I-126 | 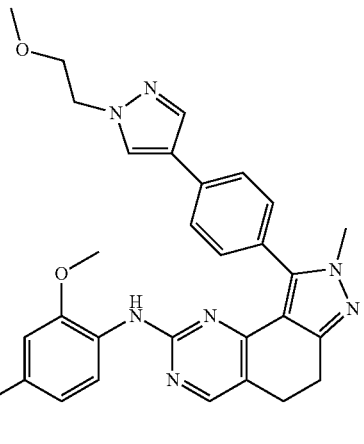 | 1.18 | 552 | E |
| I-127 | 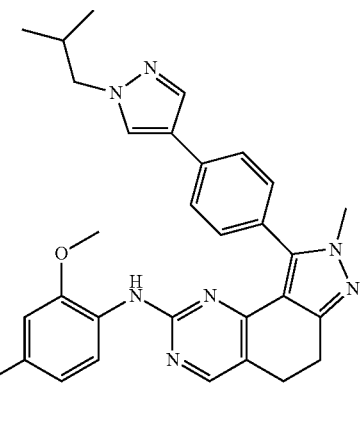 | | 550 | E |
| I-128 | 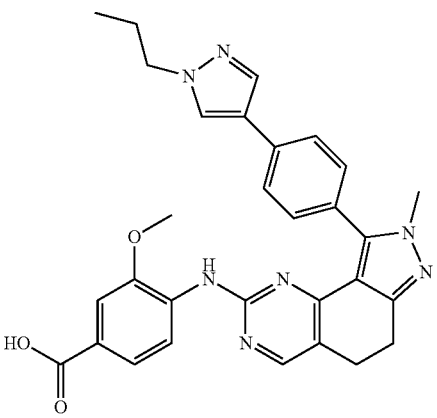 [SMILES: CCCn1cc(-c2ccc(-c3c4c(nn3C)CCc3cnc(Nc5ccc(C(=O)O)cc5OC)nc3-4)cc2)cn1] | 1.25 | 536 | E |

D.3. Amide Coupling (Method L)

D.3.1. Experimental Procedure for the Synthesis of I-129

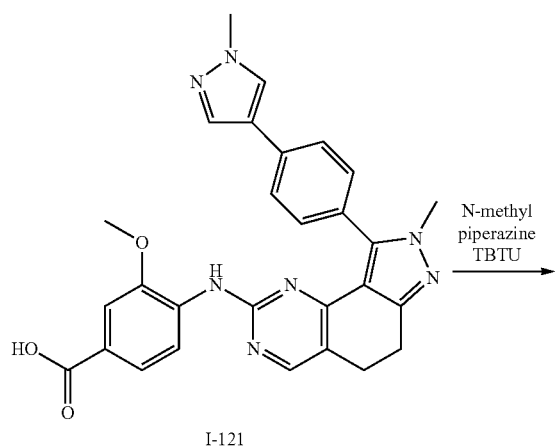

I-121

N-methyl piperazine
TBTU
→

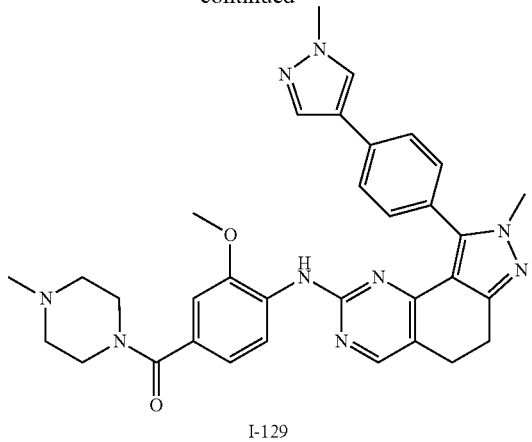

I-129

I-121 (75 mg, 150 μmol), TBTU (72 mg, 225 μmol) and triethylamine (104 μL, 720 μmol) in DMSO (500 μL) are stirred for 5 min at rt. N-Methylpiperazine (19 mg, 188 μmol) is added and the mixture is stirred for 30 min at rt. The reaction mixture is purified by prep. HPCL-MS.

As an alternative, conversion of the acid into the acid chloride and subsequent treatment with a suitable amine is applicable as well.

The following coupling products (table 14) are obtained in an analogous manner.

TABLE 14

| # | Structure | $t_{ret}$ [min] | M + H$^+$ | HPLC method |
|---|---|---|---|---|
| I-129 | 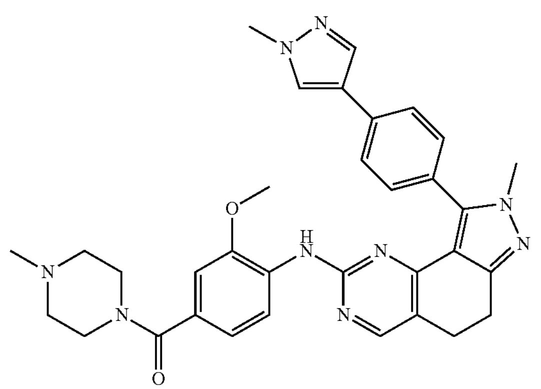 [SMILES: COc1cc(C(=O)N2CCN(C)CC2)ccc1Nc1ncc2c(n1)-c1c(nn(C)c1-c1ccc(-c3cnn(C)c3)cc1)CC2] | 1.04 | 590 | E |
| I-130 | 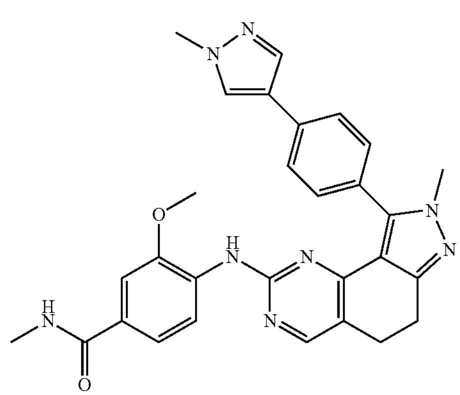 [SMILES: CNC(=O)c1ccc(Nc2ncc3c(n2)-c2c(nn(C)c2-c2ccc(-c4cnn(C)c4)cc2)CC3)c(OC)c1] | 1.22 | 521 | E |

TABLE 14-continued

| # | Structure | t_ret [min] | M + H+ | HPLC method |
|---|---|---|---|---|
| I-131 | 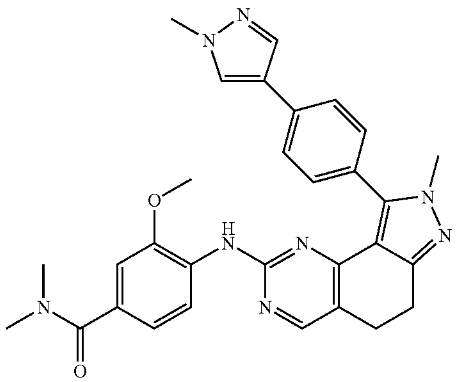 [SMILES: COc1cc(C(=O)N(C)C)ccc1Nc1ncc2c(n1)-c1c(nn(C)c1-c1ccc(-c3cnn(C)c3)cc1)CC2] | 1.25 | 535 | E |
| I-132 | 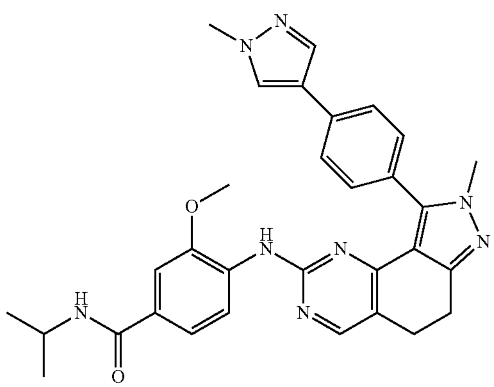 [SMILES: COc1cc(C(=O)NC(C)C)ccc1Nc1ncc2c(n1)-c1c(nn(C)c1-c1ccc(-c3cnn(C)c3)cc1)CC2] | 1.31 | 549 | E |
| I-133 | 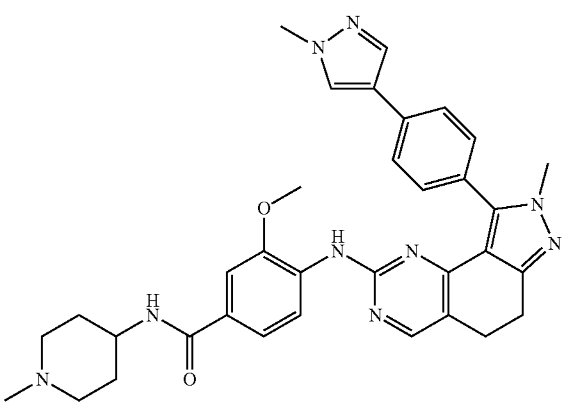 [SMILES: COc1cc(C(=O)NC2CCN(C)CC2)ccc1Nc1ncc2c(n1)-c1c(nn(C)c1-c1ccc(-c3cnn(C)c3)cc1)CC2] | 1.28 | 604 | E |

TABLE 14-continued
| # | Structure | t_ret [min] | M + H+ | HPLC method |
|---|---|---|---|---|
| I-134 | 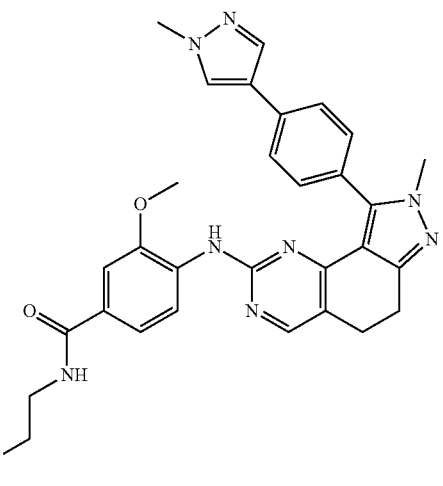 | 1.26 | 578 | E |
| I-135 | 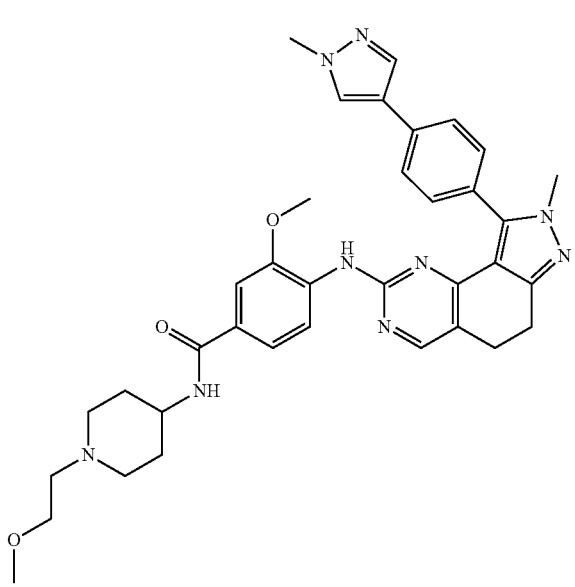 [SMILES: COCCN1CCC(NC(=O)c2ccc(Nc3ncc4c(n3)-c3c(nn(C)c3-c3ccc(-c5cnn(C)c5)cc3)CC4)c(OC)c2)CC1] | 1.32 | 648 | E |
| I-136 | 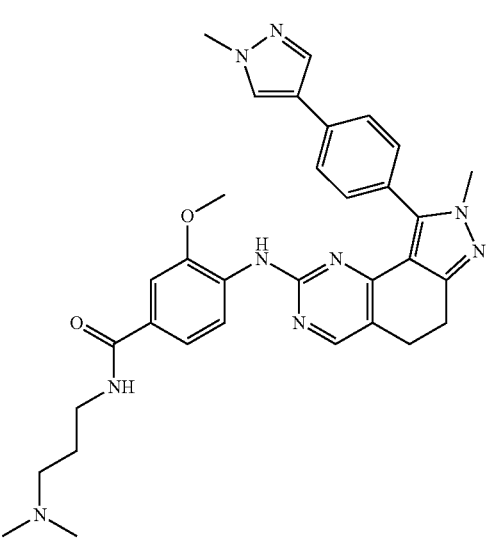 [SMILES: COc1cc(C(=O)NCCCN(C)C)ccc1Nc1ncc2c(n1)-c1c(nn(C)c1-c1ccc(-c3cnn(C)c3)cc1)CC2] | 1.32 | 592 | E |

TABLE 14-continued

| # | Structure | $t_{ret}$ [min] | M + H⁺ | HPLC method |
|---|---|---|---|---|
| I-137 | 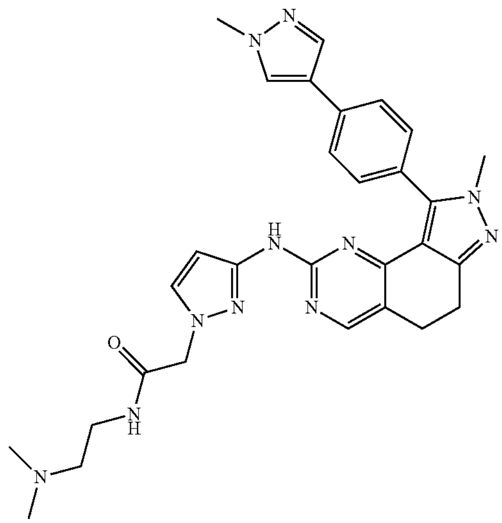 [SMILES: CN(C)CCNC(=O)Cn1ccc(Nc2ncc3c(n2)-c2c(nn(C)c2-c2ccc(-c4cnn(C)c4)cc2)CC3)n1] | 0.93 | 552 | E |
| I-138 | 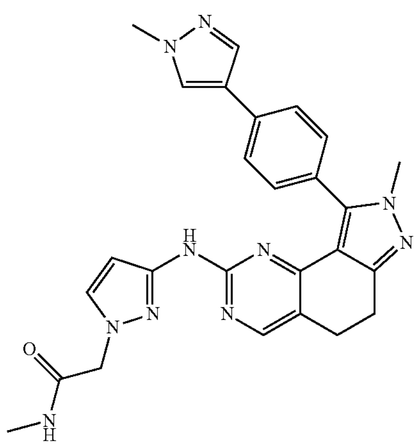 [SMILES: CNC(=O)Cn1ccc(Nc2ncc3c(n2)-c2c(nn(C)c2-c2ccc(-c4cnn(C)c4)cc2)CC3)n1] | 0.89 | 495 | E |
| I-139 | 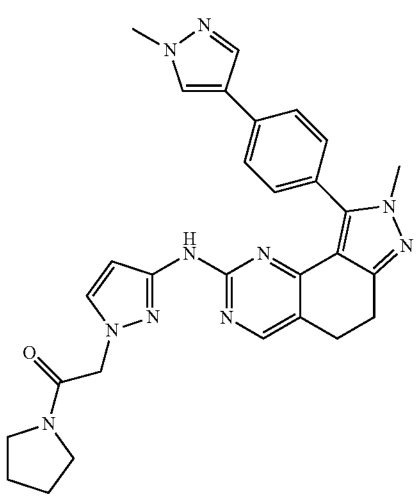 [SMILES: Cn1cc(-c2ccc(-c3c4c(nn3C)CCc3cnc(Nc5ccn(CC(=O)N6CCCC6)n5)nc3-4)cc2)cn1] | 0.94 | 535 | E |

TABLE 14-continued
| # | Structure | t_ret [min] | M + H⁺ | HPLC method |
|---|---|---|---|---|
| I-140 | 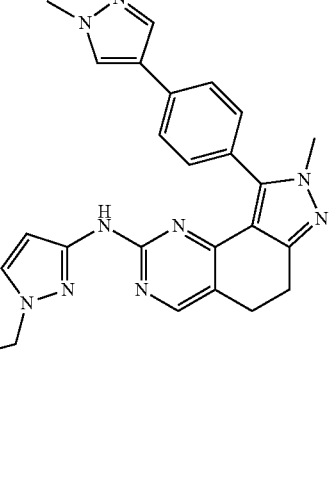 | 0.92 | 539 | E |
| I-141 | 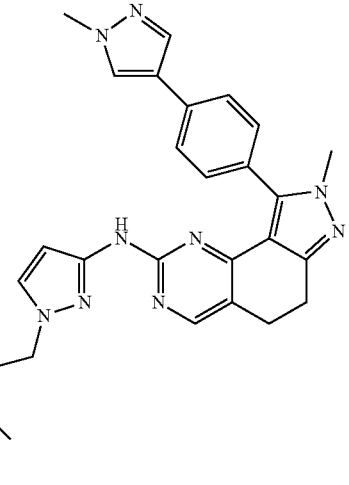 | 0.93 | 553 | E |
| I-142 | 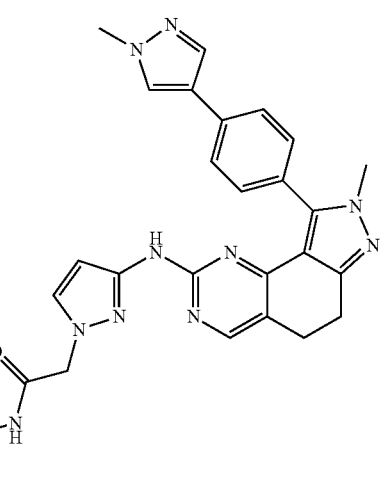 | 0.96 | 566 | E |

TABLE14-continued
| # | Structure | $t_{ret}$ [min] | M + H⁺ | HPLC method |
|---|---|---|---|---|
| I-143 | 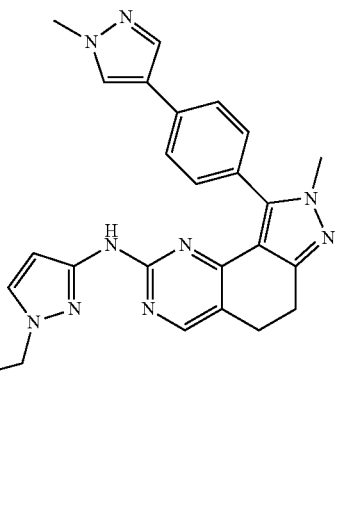 | 0.92 | 578 | E |
| I-144 | 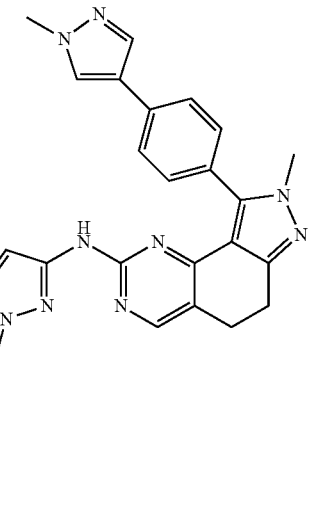 | 0.91 | 551 | E |
| I-145 | 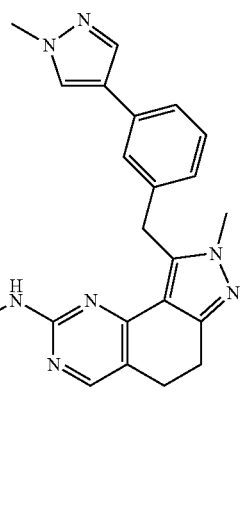 | 1.08 | 618 | E |

TABLE 14-continued
| # | Structure | $t_{ret}$ [min] | M + H⁺ | HPLC method |
|---|---|---|---|---|
| I-146 | 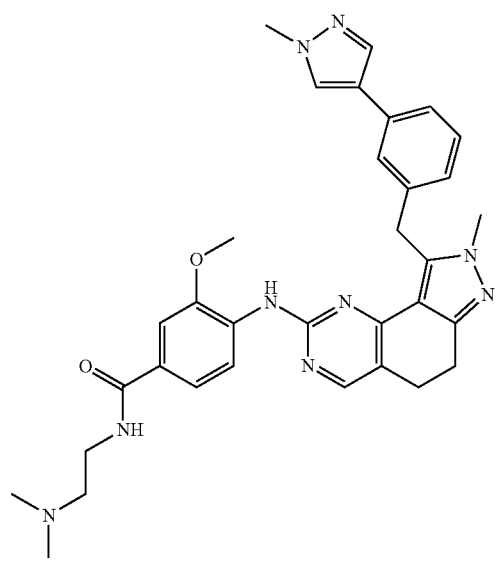 [SMILES: COc1cc(C(=O)NCCN(C)C)ccc1Nc1ncc2c(n1)-c1c(nn(C)c1Cc1cccc(-c3cnn(C)c3)c1)CC2] | 1.08 | 592 | E |
| I-147 | 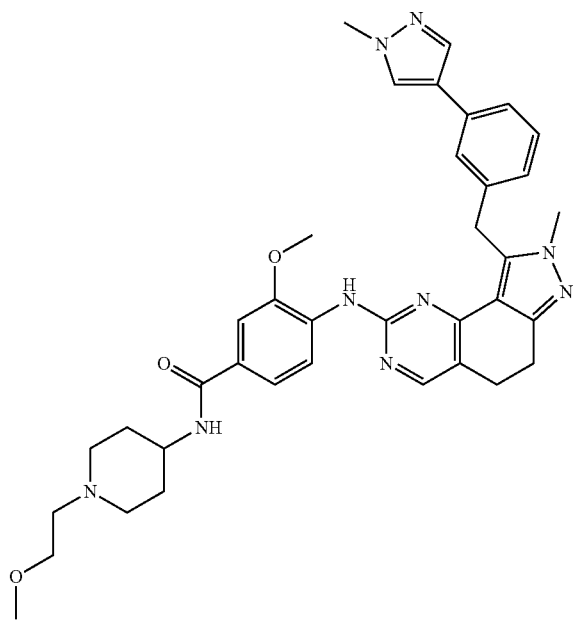 [SMILES: COCCN1CCC(NC(=O)c2ccc(Nc3ncc4c(n3)-c3c(nn(C)c3Cc3cccc(-c5cnn(C)c5)c3)CC4)c(OC)c2)CC1] | 1.09 | 662 | E |

TABLE 14-continued

| # | Structure | t_ret [min] | M + H⁺ | HPLC method |
|---|---|---|---|---|
| I-148 | 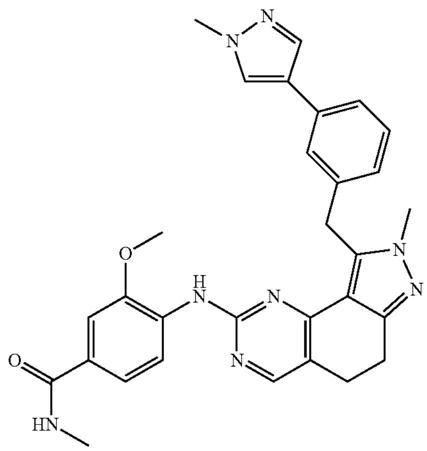 [SMILES: CNC(=O)c1ccc(Nc2ncc3c(n2)-c2c(nn(C)c2Cc2cccc(-c4cnn(C)c4)c2)CC3)c(OC)c1] | 1.03 | 535 | E |
| I-149 | 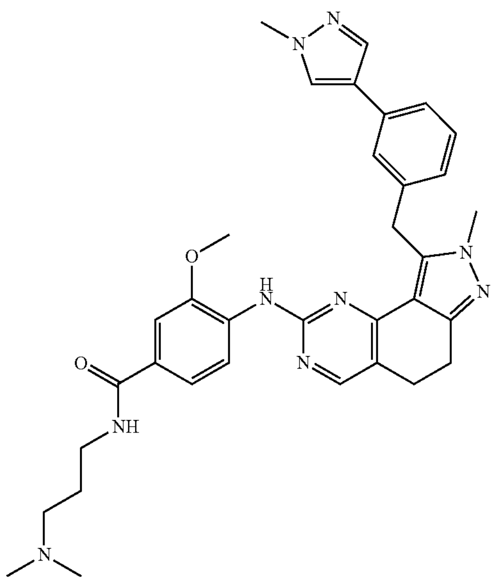 [SMILES: COc1cc(C(=O)NCCCN(C)C)ccc1Nc1ncc2c(n1)-c1c(nn(C)c1Cc1cccc(-c3cnn(C)c3)c1)CC2] | 1.11 | 606 | E |
| I-150 | 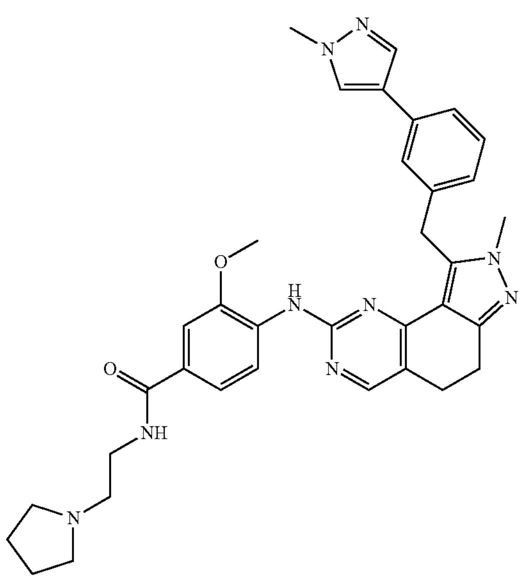 [SMILES: COc1cc(C(=O)NCCN2CCCC2)ccc1Nc1ncc2c(n1)-c1c(nn(C)c1Cc1cccc(-c3cnn(C)c3)c1)CC2] | 1.11 | 604 | E |

TABLE 14-continued
| # | Structure | $t_{ret}$ [min] | M + H⁺ | HPLC method |
|---|---|---|---|---|
| I-151 | 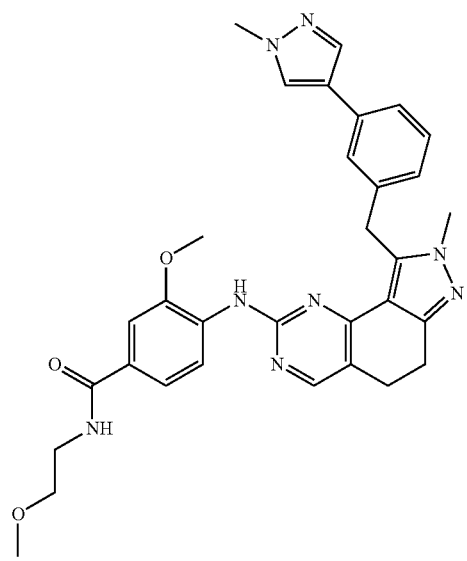 [SMILES: COCCNC(=O)c1ccc(Nc2ncc3c(n2)-c2c(nn(C)c2Cc2cccc(-c4cnn(C)c4)c2)CC3)c(OC)c1] | 1.07 | 565 | E |
| I-152 | 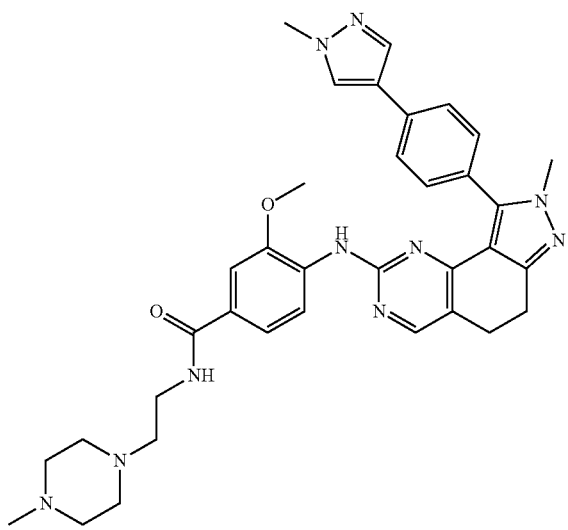 [SMILES: COc1cc(C(=O)NCCN2CCN(C)CC2)ccc1Nc1ncc2c(n1)-c1c(nn(C)c1-c1ccc(-c3cnn(C)c3)cc1)CC2] | 1.03 | 633 | E |

TABLE 14-continued

| # | Structure | $t_{ret}$ [min] | M + H⁺ | HPLC method |
|---|---|---|---|---|
| I-153 | 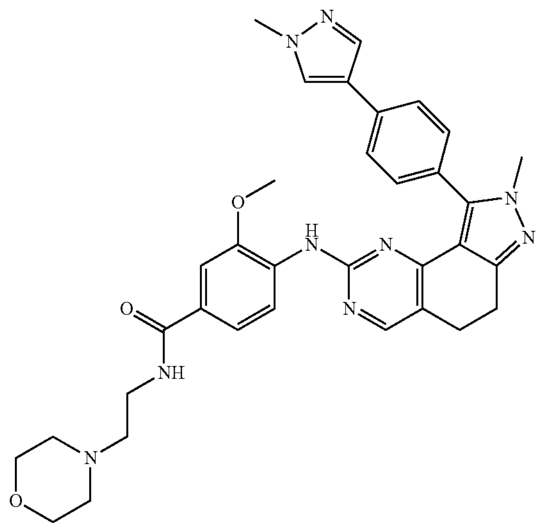 [SMILES: COc1cc(C(=O)NCCN2CCOCC2)ccc1Nc1ncc2c(n1)-c1c(nn(C)c1-c1ccc(-c3cnn(C)c3)cc1)CC2] | 1.04 | 620 | E |
| I-154 | 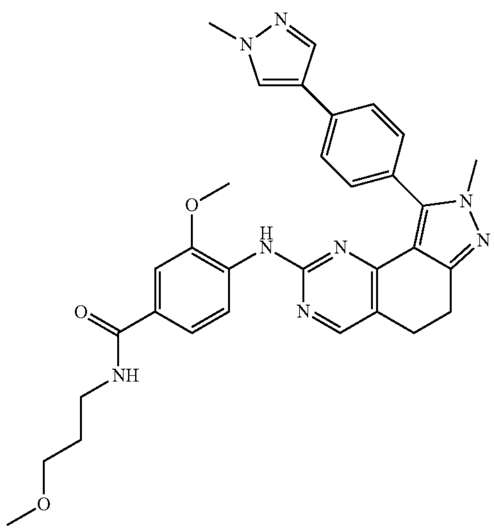 [SMILES: COCCCNC(=O)c1ccc(Nc2ncc3c(n2)-c2c(nn(C)c2-c2ccc(-c4cnn(C)c4)cc2)CC3)c(OC)c1] | 1.09 | 579 | E |
| I-155 | 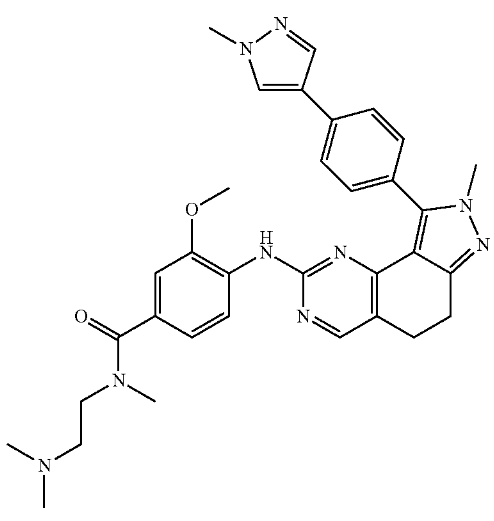 [SMILES: COc1cc(C(=O)N(C)CCN(C)C)ccc1Nc1ncc2c(n1)-c1c(nn(C)c1-c1ccc(-c3cnn(C)c3)cc1)CC2] | 1.06 | 592 | E |

TABLE 14-continued
| # | Structure | $t_{ret}$ [min] | M + H⁺ | HPLC method |
|---|---|---|---|---|
| I-156 | 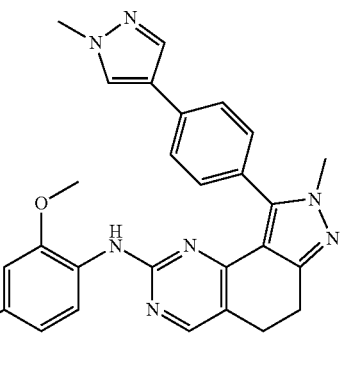 | 1.05 | 577 | E |
| I-157 | 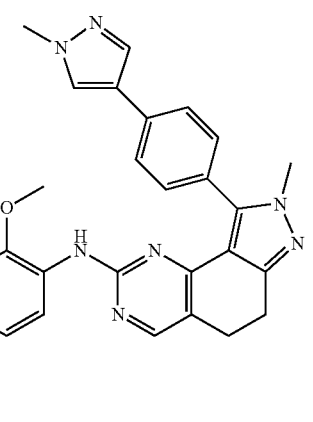 | 1.08 | 535 | E |
| I-158 | 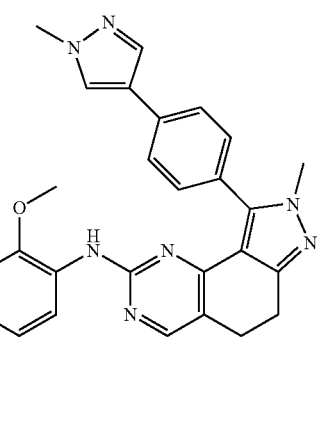 | 1.13 | 549 | E |

TABLE 14-continued

| # | Structure | t_ret [min] | M + H⁺ | HPLC method |
|---|---|---|---|---|
| I-159 | 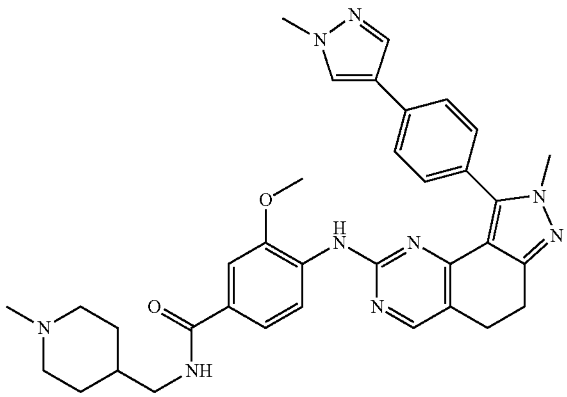 [SMILES: COc1cc(C(=O)NCC2CCN(C)CC2)ccc1Nc1ncc2c(n1)-c1c(nn(C)c1-c1ccc(-c3cnn(C)c3)cc1)CC2] | 1.08 | 618 | E |
| I-160 | 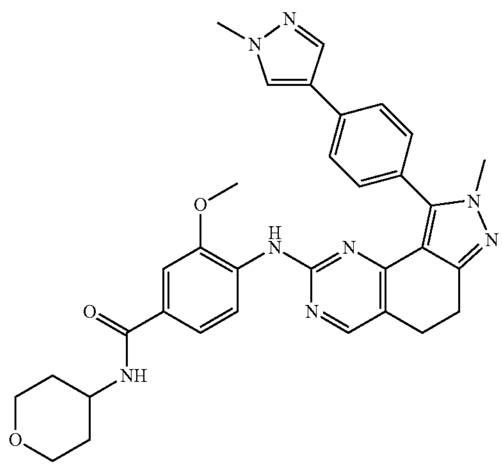 [SMILES: COc1cc(C(=O)NC2CCOCC2)ccc1Nc1ncc2c(n1)-c1c(nn(C)c1-c1ccc(-c3cnn(C)c3)cc1)CC2] | 1.07 | 591 | E |
| I-161 | 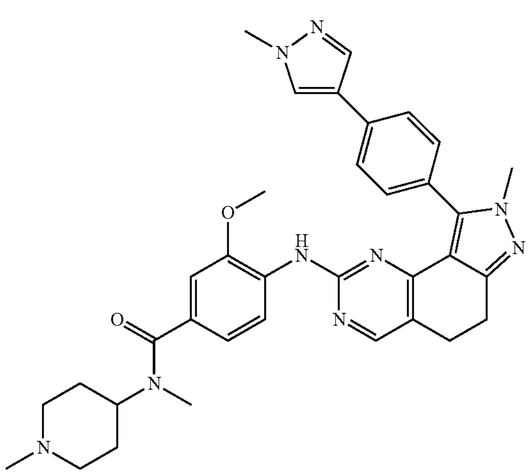 [SMILES: COc1cc(C(=O)N(C)C2CCN(C)CC2)ccc1Nc1ncc2c(n1)-c1c(nn(C)c1-c1ccc(-c3cnn(C)c3)cc1)CC2] | 1.06 | 618 | E |

TABLE 14-continued
| # | Structure | $t_{ret}$ [min] | M + H⁺ | HPLC method |
|---|---|---|---|---|
| I-162 | 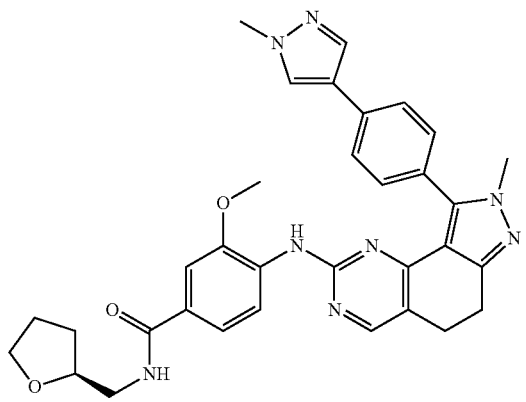 [SMILES: COc1cc(C(=O)NC[C@@H]2CCCO2)ccc1Nc1ncc2c(n1)-c1c(nn(C)c1-c1ccc(-c3cnn(C)c3)cc1)CC2] | 1.10 | 591 | E |
| I-163 | 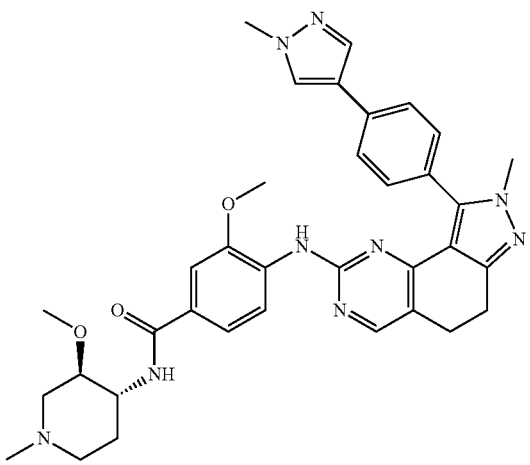 [SMILES: COc1cc(C(=O)N[C@@H]2CCN(C)C[C@H]2OC)ccc1Nc1ncc2c(n1)-c1c(nn(C)c1-c1ccc(-c3cnn(C)c3)cc1)CC2] | 1.06 | 634 | E |

TABLE 14-continued

| # | Structure | $t_{ret}$ [min] | M + H⁺ | HPLC method |
|---|---|---|---|---|
| I-164 | 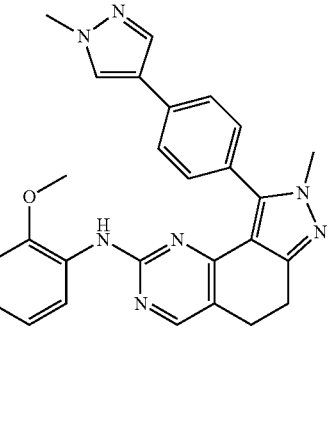 | 1.04 | 576 | E |
| I-165 | 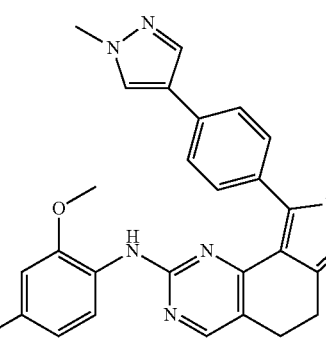 | 1.08 | 579 | E |

D.4. Amide Cleavage (Method M)

D.4.1. Experimental Procedure for the Synthesis of I-166

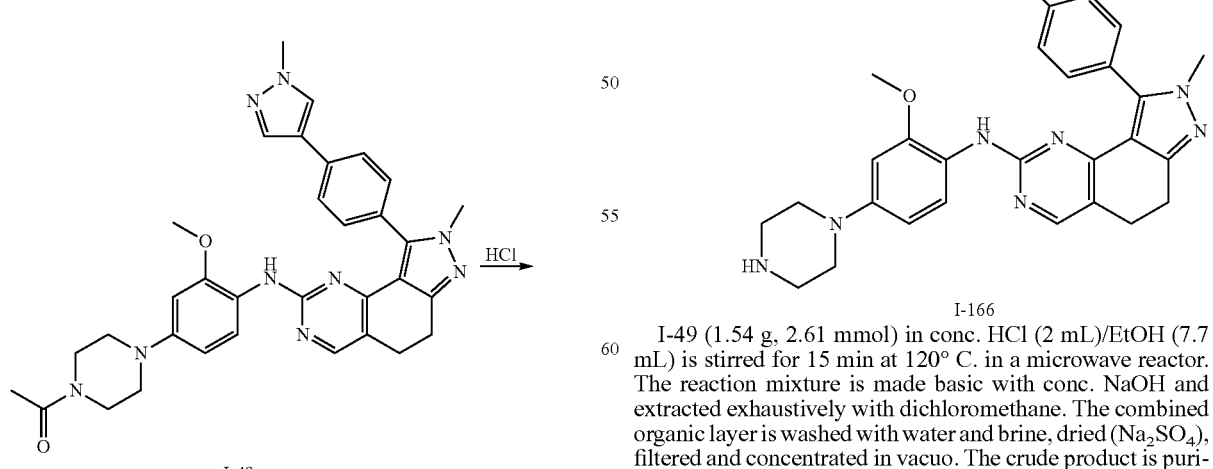

I-49 (1.54 g, 2.61 mmol) in conc. HCl (2 mL)/EtOH (7.7 mL) is stirred for 15 min at 120° C. in a microwave reactor. The reaction mixture is made basic with conc. NaOH and extracted exhaustively with dichloromethane. The combined organic layer is washed with water and brine, dried ($Na_2SO_4$), filtered and concentrated in vacuo. The crude product is purified by flash chromatography if necessary.

The following cleavage products (table 15) are obtained in an analogous manner.

TABLE 15
| # | Structure | $t_{ret}$ [min] | $[M + H]^+$ | HPLC method |
|---|---|---|---|---|
| I-166 | 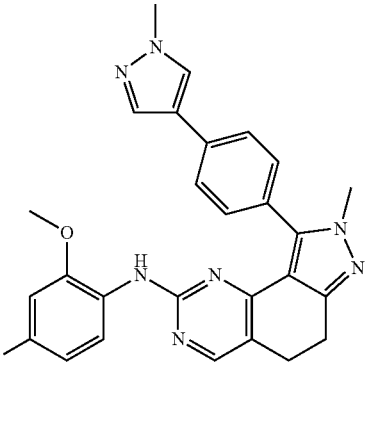 | 0.38 | 548 | B |
| I-167 | 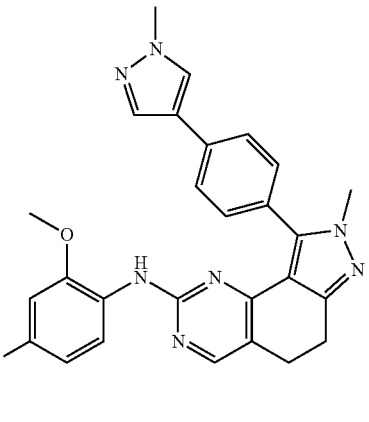 | 0.40 | 526 | B |
| I-168 | 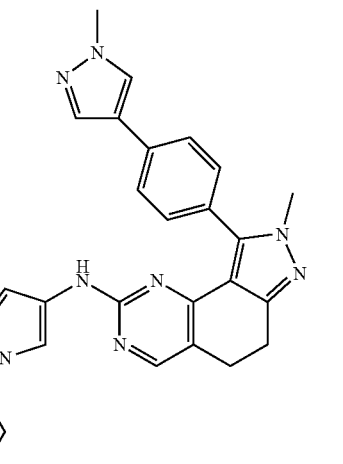 | 0.29 | 509 | B |

193
D.5. Reductive Amination (Method N)

D.5.1. Experimental Procedure for the Synthesis of I-169

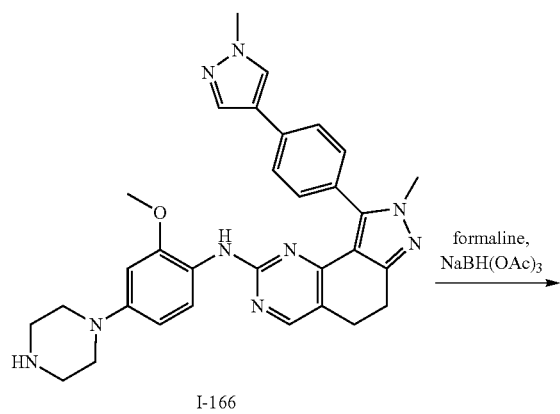

formaline, NaBH(OAc)₃ →

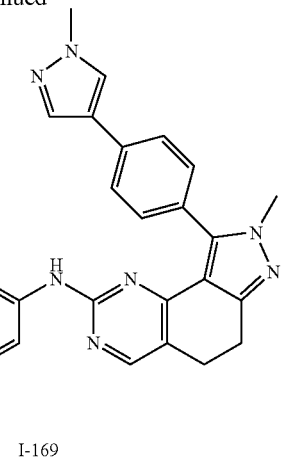

I-169

I-166 (100 mg, 180 µmol) and 37% aq. formaldehyde (40 µL, 540 µmol) are stirred in NMP (500 µL) for 10 min at rt. Sodium triacetoxy borohydride (114 mL, 540 µmol) is added and the mixture is stirred for 1 h at rt. The reaction mixture is purified by prep. HPCL-MS.

The following alkylation products (table 16) are obtained in an analogous manner.

TABLE 16

| # | Structure | $t_{ret}$ [min] | M + H⁺ | HPLC method |
|---|-----------|-----------------|--------|-------------|
| I-169 | 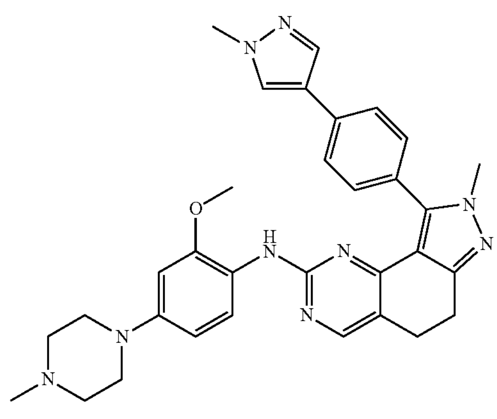 [SMILES: COc1cc(N2CCN(C)CC2)ccc1Nc1ncc2c(n1)-c1c(nn(C)c1-c1ccc(-c3cnn(C)c3)cc1)CC2] | 1.26 | 562 | E |
| I-170 | 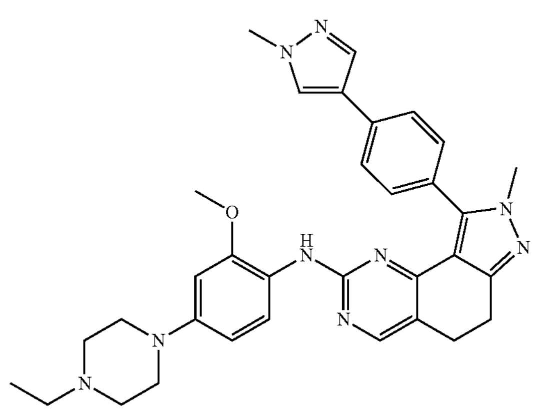 [SMILES: CCN1CCN(c2ccc(Nc3ncc4c(n3)-c3c(nn(C)c3-c3ccc(-c5cnn(C)c5)cc3)CC4)c(OC)c2)CC1] | 1.32 | 576 | E |

TABLE 16-continued
| # | Structure | t_ret [min] | M + H+ | HPLC method |
|---|---|---|---|---|
| I-171 | 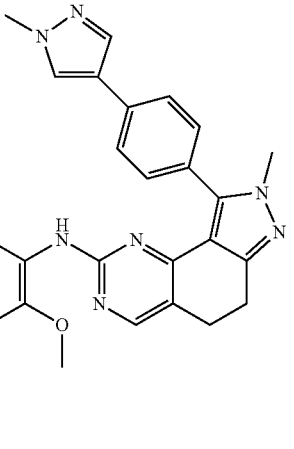 | 1.29 | 632 | E |
| I-172 | 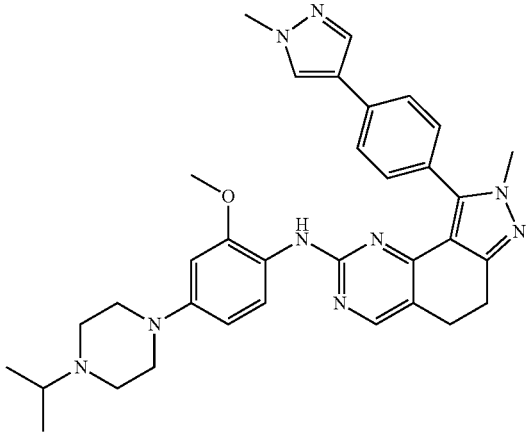 [SMILES: COc1cc(N2CCN(C(C)C)CC2)ccc1Nc1ncc2c(n1)-c1c(nn(C)c1-c1ccc(-c3cnn(C)c3)cc1)CC2] | 1.38 | 590 | E |
| I-173 | 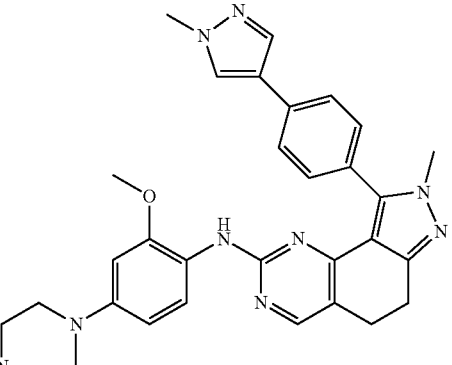 | 1.11 | 576 | E |

197

D.6. Alkylation by Nucleophilic Substitution (Method O)

D.6.1. Experimental Procedure for the Synthesis of I-174

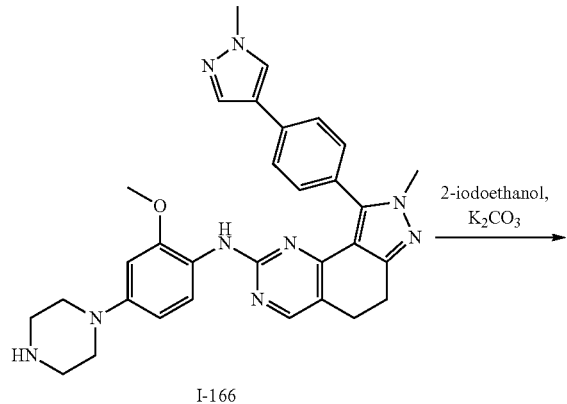

I-166

198

-continued

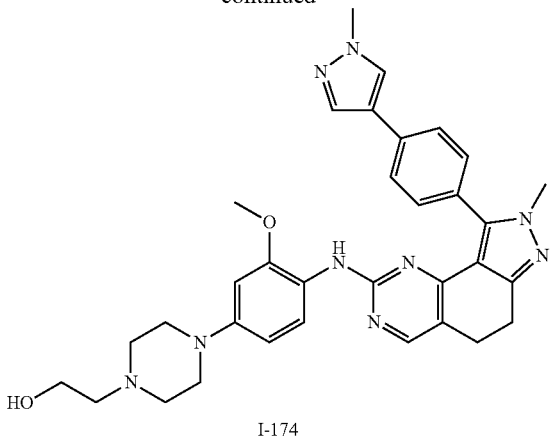

I-174

I-166 (100 mg, 180 μmol), 2-iodoethanol (56 mg, 324 μmol) and K$_2$CO$_3$ (75 mg, 540 μmol) are stirred in NMP (500 μL) for 48 h at rt. The reaction mixture is purified by prep. HPCL-MS.

The following alkylation products (table 17) are obtained in an analogous manner.

TABLE 17

| # | Struktur | t$_{ret}$ [min] | M + H$^+$ | HPLC method |
|---|---|---|---|---|
| I-174 | | 1.20 | 592 | E |
| I-175 | | 1.01 | 565 | E |

199

D.7. Sulfonamide Formation (Method P)

D.7.1. Experimental Procedure for the Synthesis of I-176

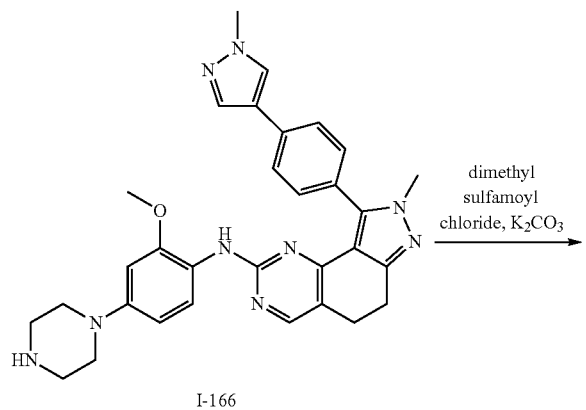

I-166

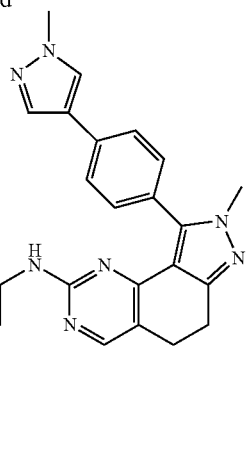

I-176

I-166 (100 mg, 180 µmol), dimethylsulfamoyl chloride (30 µL, 270 µmol) and triethylamine (104 µL, 720 µmol) in NMP (500 µL) are stirred for 18 h at rt. The reaction mixture is purified by prep. HPCL-MS.

The following amidation products (table 18) are obtained in an analogous manner.

TABLE 18

| # | Structure | $t_{ret}$ [min] | M + H⁺ | HPLC method |
|---|---|---|---|---|
| I-176 | 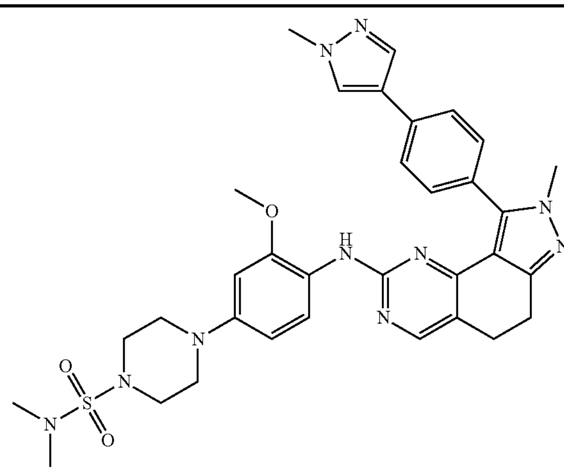 | 1.40 | 655 | E |
| I-177 | 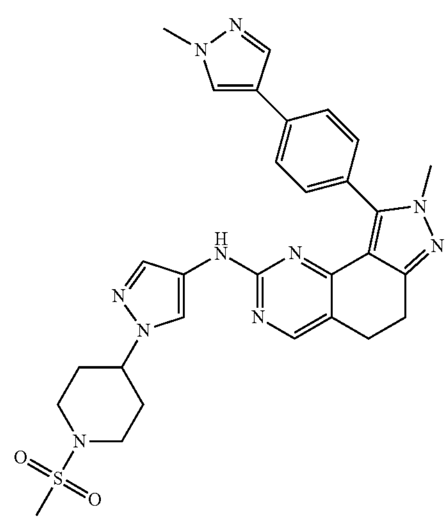 [SMILES: Cn1cc(-c2ccc(-c3c4c(nn3C)CCc3cnc(Nc5cnn(C6CCN(S(C)(=O)=O)CC6)c5)nc3-4)cc2)cn1] | 0.99 | 585 | E |

TABLE 18-continued

| # | Structure | $t_{ret}$ [min] | M + H$^+$ | HPLC method |
|---|---|---|---|---|
| I-178 | 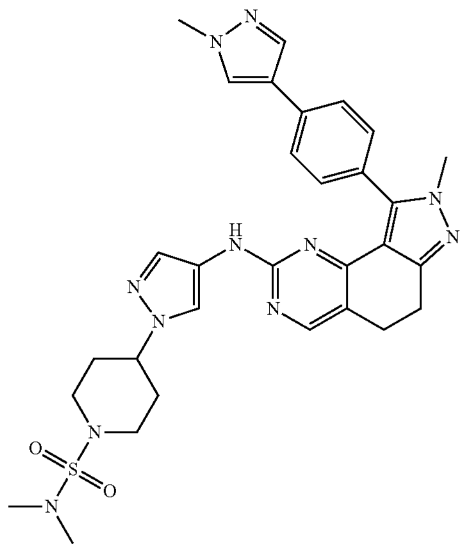 [SMILES: CN(C)S(=O)(=O)N1CCC(n2cc(Nc3ncc4c(n3)-c3c(nn(C)c3-c3ccc(-c5cnn(C)c5)cc3)CC4)cn2)CC1] | 1.06 | 614 | E |

The following Examples describe the biological activity of the compounds according to the invention, without restricting the invention to these Examples.

Compounds of general formula (I) are characterised by their many possible applications in the therapeutic field. Particular mention should be made of those applications in which the inhibiting effect on the proliferation of cultivated human tumour cells but also on the proliferation of other cells such as endothelial cells, for example, are involved.

Insulin-Like Growth Factor-1 Receptor (IGF-1R)-Kinase Assay

The kinase activity is measured by DELFIA® assay (dissociation-enhanced lanthanide fluorescence immunoassay, Perkin Elmer). The cytoplasmic kinase domain of human IGF-1R (amino acids 964-1370) is expressed as a fusion protein with a glutathione-S-transferase tag (IGF-1R-GST) in High Five™ Cells (Invitrogen). Enzyme activity is measured in the presence of substances and a control substance. Polyglutamate-tyrosine peptide (pEY, Sigma Aldrich) and biotinylated pEY (bio-pEY) are used as reaction substrates.

10 µL of substance in 25% DMSO are mixed with 30 µL of IGF-1R-GST solution (67 mM HEPES pH 7.4, 15 µg/mL pEY, 1.7 µg/mL bio-pEY, 13.3 mM MgCl$_2$, 3.3 mM dithiothreitol, 0.0033% Brij 35, 2 ng IGF-1R-GST) in 96-well plates. The reactions are started with 10 µL of a 750 µM ATP solution. After 40 min at RT the reactions are stopped with 50 µL of stop solution (250 mM EDTA, 20 mM HEPES pH 7.4). 90 µL from each reaction are transferred onto streptavidin-coated 96-well plates. After 120 min incubation at RT the plates are washed three times with 200 µL phosphate-buffered saline (PBS) per well. The plates are incubated for 60 min with 100 µL of europium-coupled antibody against phospho-tyrosine (diluted 1/2000 in Perkin Elmer DELFIA assay buffer) per well. The plates are washed three times with 200 µL per well of DELFIA washing buffer. 100 µL DELFIA Enhancement Solution (Perkin Elmer) is added to each well, and the plates are incubated for 10 min. The fluorescence signal is measured with a Wallac Victor TRF Reader. IC$_{50}$ values for the inhibition of the IGF-1R-kinase activity are calculated using the programmes Fifty (Version 2) and GraphPad (Version 3.0).

Table 19 shows the IC$_{50}$ values of example compounds determined using the above assay.

TABLE 19

| # | IGF1R [nM] |
|---|---|
| I-003 | 0.23 |
| I-004 | 0.16 |
| I-005 | 0.1 |
| I-006 | 0.88 |
| I-007 | 3 |
| I-008 | 0.76 |
| I-009 | 0.51 |
| I-010 | 0.26 |
| I-011 | 0.27 |
| I-012 | 0.36 |
| I-013 | 0.39 |
| I-014 | 1 |
| I-015 | 0.16 |
| I-016 | 0.36 |
| I-017 | 0.46 |
| I-018 | 0.23 |
| I-019 | 0.87 |
| I-020 | 0.21 |
| I-021 | 0.12 |
| I-022 | 0.17 |
| I-023 | 0.42 |
| I-024 | 0.16 |
| I-025 | 0.38 |
| I-026 | 0.28 |
| I-027 | 0.28 |
| I-028 | 0.91 |
| I-029 | 0.17 |
| I-030 | 0.1 |
| I-031 | 0.05 |
| I-032 | 0.21 |
| I-033 | 0.24 |
| I-034 | 0.17 |
| I-035 | 0.08 |
| I-036 | 0.37 |
| I-037 | 0.23 |

TABLE 19-continued

| # | IGF1R [nM] |
|---|---|
| I-038 | 0.22 |
| I-039 | 0.8 |
| I-040 | 0.57 |
| I-041 | 1 |
| I-051 | 0.21 |
| I-053 | 0.21 |
| I-054 | 0.19 |
| I-055 | 2 |
| I-056 | 1 |
| I-057 | 0.55 |
| I-058 | 0.18 |
| I-059 | 0.13 |
| I-060 | 0.31 |
| I-061 | 0.15 |
| I-062 | 0.13 |
| I-063 | 0.16 |
| I-064 | 0.31 |
| I-065 | 0.38 |
| I-066 | 15 |
| I-067 | 2 |
| I-068 | 3 |
| I-069 | 5 |
| I-070 | 0.26 |
| I-071 | 0.79 |
| I-072 | 0.78 |
| I-073 | 0.35 |
| I-074 | 0.1 |
| I-075 | 0.21 |
| I-076 | 0.35 |
| I-077 | 0.24 |
| I-078 | 0.37 |
| I-079 | 0.68 |
| I-080 | 0.22 |
| I-081 | 0.16 |
| I-082 | 0.28 |
| I-083 | 0.25 |
| I-084 | 0.27 |
| I-085 | 0.2 |
| I-086 | 0.49 |
| I-087 | 0.31 |
| I-088 | 0.79 |
| I-089 | 0.35 |
| I-090 | 1 |
| I-091 | 0.82 |
| I-092 | 0.25 |
| I-093 | 0.38 |
| I-094 | 0.48 |
| I-095 | 0.61 |
| I-096 | 0.39 |
| I-097 | 1 |
| I-098 | 0.91 |
| I-099 | 0.74 |
| I-100 | 0.46 |
| I-101 | 0.41 |
| I-102 | 0.75 |
| I-103 | 0.44 |
| I-104 | 0.59 |
| I-105 | 0.57 |
| I-106 | 2 |
| I-107 | 0.31 |
| I-108 | 0.48 |
| I-109 | 0.32 |
| I-110 | 0.9 |
| I-111 | 2 |
| I-112 | 0.31 |
| I-113 | 0.09 |
| I-114 | 0.13 |
| I-115 | 0.11 |
| I-116 | 0.11 |
| I-117 | 0.13 |
| I-118 | 0.1 |
| I-119 | 0.09 |
| I-120 | 0.25 |
| I-121 | 1 |
| I-124 | 1 |
| I-125 | 2 |
| I-126 | 1 |
| I-127 | 7 |
| I-128 | 3 |
| I-129 | 0.16 |
| I-130 | 0.18 |
| I-131 | 0.17 |
| I-132 | 0.26 |
| I-133 | 0.14 |
| I-134 | 0.13 |
| I-135 | 0.14 |
| I-136 | 0.13 |
| I-137 | 0.38 |
| I-138 | 0.39 |
| I-139 | 0.33 |
| I-140 | 0.56 |
| I-141 | 0.51 |
| I-142 | 0.3 |
| I-143 | 0.24 |
| I-144 | 0.39 |
| I-145 | 0.2 |
| I-146 | 0.17 |
| I-147 | 0.16 |
| I-148 | 0.15 |
| I-149 | 0.08 |
| I-150 | 0.14 |
| I-151 | 0.37 |
| I-152 | 0.21 |
| I-153 | 0.38 |
| I-154 | 0.38 |
| I-155 | 0.15 |
| I-156 | 0.22 |
| I-157 | 0.37 |
| I-158 | 0.66 |
| I-159 | 0.16 |
| I-160 | 0.61 |
| I-161 | 0.14 |
| I-162 | 0.39 |
| I-163 | 0.23 |
| I-164 | 0.19 |
| I-165 | 0.22 |
| I-169 | 0.2 |
| I-170 | 0.09 |
| I-171 | 0.08 |
| I-172 | 0.05 |
| I-173 | 0.1 |
| I-174 | 0.08 |
| I-175 | 0.16 |
| I-176 | 2 |
| I-177 | 0.23 |
| I-178 | 0.34 |
| I-179 | 4 |
| I-180 | 2 |
| I-181 | 2 |
| I-182 | 2 |
| I-183 | 2 |
| I-184 | 5 |
| I-185 | 2 |
| I-186 | 2 |
| I-187 | 3 |
| I-188 | 2 |
| I-189 | 0.31 |
| I-190 | 0.35 |
| I-191 | 0.26 |

Cellular IGF-1R-Phosphorylation Assay

The activity of substances against the phosphorylation of IGF-1R in activated cells is measured as follows: mouse fibroblast cells (transfected with human IGF-1R, Fibro-hIGF-1R) are cultivated in standard medium (DMEM, 10% foetal calf serum (FCS, Gibco), 1×MEM Non-Essential Amino Acids (NEAA, Gibco), 7.5% sodium hydrogen carbonate (Gibco) and 0.3 mg/mL Puromycin (Sigma)) in a humid incubator at 37° C. with 5 $CO_2$/95% air.

10000 Fibro-hIGF-1R cells per well in 200 µL of standard medium are seeded into 96-well plates and cultivated overnight. The next day, the medium is suction filtered and the cells are cultivated in 90 μL serum-reduced medium (DMEM, 0.5% FCS, 1×MEM NEAA, 7.5% sodium hydrogen carbonate) for a further 24 h. 10 μL of substance solution (diluted in serum-reduced medium) is added thereto, and the cells are incubated for a further 120 min in the incubator. The phosphorylation of IGF-1R is activated for 30 min by the addition of IGF-1 (20 ng/mL in serum-reduced medium). All further incubations are carried out at RT. The supernatant is suction filtered from the wells, and the cells are fixed in 100 μL per well of 4% paraformaldehyde (diluted in PBS). The supernatant in the well is suction filtered and the cells are permeabilised for 5 min in 300 μL per well of 0.1% TritonX-100 (diluted in PBS). The supernatants are suction filtered once again and the cells are incubated for 20 min in quenching buffer (PBS with 0.1% TritonX-100 and 1.2% hydrogen peroxide), to inhibit the endogenous peroxidase of the cells. The cells are washed for 5 min with 300 μL per well of PBS with 0.1% TritonX-100 and then incubated for 60 min with 100 μL per well of blocking buffer (PBS with 0.1% TritonX-100 and 5 Bovine Serum Albumin (BSA)). The blocking buffer is exchanged for 50 μL of the first antibody buffer (1/1000 dilute anti-phospho-IGF-1 receptor β (Tyr1135/1136)/insulin receptor β (Tyr1150/1151) (19H7) rabbit monoclonal antibody from Cell Signaling Technology in blocking buffer) and the plates are incubated overnight at 4° C. The next day the plates are washed for 5 min with 300 μL PBS/0.1% TritonX-100 at RT and then incubated for 60 min with 50 μL per well of the second antibody buffer (1/500 diluted Goat Anti-Rabbit Immunoglobulin-Horseradish Peroxidase (HRP) (Dako) in blocking buffer) at RT. The plates are washed first for 5 min with 300 μL PBS/0.1% TritonX-100 and then for a further 5 min with 300 μL PBS at RT. The plates are developed for 10 min with 100 μL per well of a peroxidase solution (1:1 mixture of TMB Peroxidase Substrate and Peroxidase Solution B from Kirkegaard & Perry Laboratories, Inc.). The reactions are stopped with 100 μL per well of stop solution (1 M phosphoric acid). The absorbance in each well is measured at 450 nm with a SpectraMax Absorbance Reader. $EC_{50}$ values for inhibiting the phosphorylation of the IGF-1R in activated cells are calculated using the programmes Fifty (Version 2) and GraphPad (Version 3.0).

The $EC_{50}$ ranges of the following compounds were determined in this assay ("A"<10 nM; 10 nM<"B"<100 nM; 100 nM<"C"<600 nM):

TABLE 20

| # | pIGF-1R [nM] |
|---|---|
| I-003 | A |
| I-004 | A |
| I-005 | B |
| I-006 | A |
| I-007 | A |
| I-008 | A |
| I-009 | B |
| I-010 | A |
| I-011 | A |
| I-012 | A |
| I-013 | B |
| I-014 | B |
| I-015 | A |
| I-016 | A |
| I-017 | B |
| I-018 | A |
| I-019 | B |
| I-020 | A |
| I-021 | A |
| I-022 | B |
| I-023 | A |

TABLE 20-continued

| # | pIGF-1R [nM] |
|---|---|
| I-025 | A |
| I-026 | A |
| I-027 | A |
| I-051 | B |
| I-053 | A |
| I-055 | B |
| I-056 | B |
| I-057 | A |
| I-058 | A |
| I-059 | A |
| I-060 | B |
| I-061 | A |
| I-062 | A |
| I-063 | B |
| I-064 | A |
| I-065 | B |
| I-066 | C |
| I-067 | B |
| I-068 | C |
| I-069 | C |
| I-070 | A |
| I-071 | B |
| I-072 | A |
| I-073 | B |
| I-074 | A |
| I-051 | B |
| I-076 | B |
| I-077 | A |
| I-078 | A |
| I-079 | B |
| I-080 | A |
| I-081 | A |
| I-082 | A |
| I-083 | A |
| I-084 | B |
| I-085 | B |
| I-086 | A |
| I-087 | A |
| I-088 | A |
| I-089 | A |
| I-112 | A |
| I-113 | A |
| I-114 | B |
| I-115 | A |
| I-116 | A |
| I-117 | A |
| I-118 | B |
| I-119 | A |
| I-120 | A |
| I-121 | B |
| I-124 | B |
| I-125 | A |
| I-126 | A |
| I-127 | B |
| I-128 | B |
| I-129 | A |
| I-130 | A |
| I-131 | A |
| I-132 | A |
| I-133 | B |
| I-134 | A |
| I-135 | A |
| I-136 | A |
| I-137 | B |
| I-138 | B |
| I-139 | A |
| I-140 | B |
| I-141 | B |
| I-142 | B |
| I-143 | B |
| I-144 | B |
| I-145 | A |
| I-146 | B |
| I-147 | A |
| I-148 | A |
| I-149 | B |
| I-150 | A |

TABLE 20-continued

| # | pIGF-1R [nM] |
|---|---|
| I-151 | A |
| I-152 | B |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | A |
| I-164 | B |
| I-165 | A |
| I-169 | B |
| I-170 | A |
| I-171 | A |
| I-172 | A |
| I-173 | A |
| I-174 | B |
| I-176 | A |
| I-179 | C |
| I-180 | C |
| I-181 | C |
| I-182 | B |
| I-183 | B |
| I-184 | C |
| I-185 | B |

Cell Proliferation Assays

Compounds were tested for their anti-proliferative effects in the TC-71 (Ewing's sarcoma) and HCT 116 (colorectal carcinoma) cancer cell lines in vitro. Published scientific data has described that interference with the Insulin-like Growth Factor-1 Receptor (IGF-1R) signaling pathway reduces the proliferation of TC-71 cells [1]. Therefore TC-71 cells served as a positive control cell line for monitoring the activity of compounds against IGF-1R-mediated cell proliferation. In contrast, published data has demonstrated that the proliferation of HCT 116 cells is independent of IGF-1R signaling [2]. Therefore the HCT 116 cell line served as a negative control.

2000 TC-71 cells or 1000 HCT 116 cells were seeded per well in 180 μL IMDM+10% foetal calf serum (FCS)+penicillin/streptomycin into 96-well microtitre plates. The plates were placed in a cell culture incubator (37° C. in a humidified atmosphere of 95% $O_2$/5 $CO_2$) overnight. The following day, serial dilutions of compounds, prepared in duplicates, were transferred onto the cell layers (controls without compound). The cells were cultivated for a further 72 h in the cell culture incubator. 20 μL of Alamar Blue™ (Serotec Ltd, Düsseldorf, Germany) was added to each well and the plates incubated for 7 h in the cell culture incubator. Fluorescence (extinction wavelength of 544 nm and emission at 590 nm) was then measured and the normalized data fitted by iterative calculation with a sigmoidal curve analysis program (Graph Pad Prism) with a variable Hill slope to determine the $EC_{50}$ values.

The $EC_{50}$ ranges of the following compounds were determined on TC-71 cells according to this assay ("A"<10 nM; 10 nM<"B"<100 nM; 100 nM<"C"<200 nM):

TABLE 21

| # | TC71 [nM] |
|---|---|
| I-003 | A |
| I-004 | A |
| I-005 | A |
| I-006 | A |
| I-007 | A |
| I-008 | A |
| I-009 | A |
| I-010 | A |
| I-011 | A |
| I-012 | A |
| I-013 | A |
| I-014 | B |
| I-015 | A |
| I-016 | A |
| I-017 | A |
| I-018 | B |
| I-019 | A |
| I-020 | A |
| I-021 | A |
| I-022 | A |
| I-023 | A |
| I-024 | A |
| I-025 | A |
| I-026 | A |
| I-027 | A |
| I-028 | A |
| I-029 | A |
| I-030 | A |
| I-031 | A |
| I-032 | A |
| I-033 | A |
| I-034 | A |
| I-035 | A |
| I-036 | A |
| I-037 | A |
| I-038 | A |
| I-039 | A |
| I-040 | B |
| I-041 | B |
| I-051 | A |
| I-053 | A |
| I-054 | A |
| I-055 | A |
| I-056 | A |
| I-057 | A |
| I-058 | A |
| I-059 | A |
| I-060 | A |
| I-061 | A |
| I-062 | A |
| I-063 | A |
| I-064 | A |
| I-065 | A |
| I-066 | C |
| I-067 | B |
| I-068 | B |
| I-069 | B |
| I-070 | A |
| I-071 | A |
| I-072 | A |
| I-073 | A |
| I-074 | A |
| I-075 | A |
| I-076 | A |
| I-077 | A |
| I-078 | A |
| I-079 | A |
| I-080 | A |
| I-081 | A |
| I-082 | A |
| I-083 | A |
| I-084 | A |
| I-085 | A |
| I-086 | A |
| I-087 | A |
| I-088 | A |
| I-089 | A |
| I-090 | A |
| I-091 | A |
| I-092 | A |

TABLE 21-continued

| # | TC71 [nM] |
|---|---|
| I-093 | A |
| I-094 | A |
| I-095 | A |
| I-096 | A |
| I-097 | A |
| I-098 | A |
| I-099 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-112 | A |
| I-113 | A |
| I-114 | A |
| I-115 | A |
| I-116 | C |
| I-117 | A |
| I-118 | A |
| I-119 | A |
| I-120 | A |
| I-121 | A |
| I-124 | A |
| I-125 | A |
| I-126 | A |
| I-127 | B |
| I-128 | A |
| I-129 | A |
| I-130 | A |
| I-131 | A |
| I-133 | A |
| I-134 | A |
| I-135 | A |
| I-136 | A |
| I-137 | B |
| I-138 | A |
| I-139 | A |
| I-140 | B |
| I-141 | A |
| I-142 | B |
| I-143 | A |
| I-144 | A |
| I-145 | A |
| I-146 | A |
| I-147 | A |
| I-148 | A |
| I-149 | A |
| I-150 | A |
| I-151 | A |
| I-152 | A |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | A |
| I-164 | A |
| I-165 | A |
| I-169 | A |
| I-170 | A |
| I-171 | A |
| I-172 | A |
| I-173 | A |
| I-174 | A |
| I-175 | A |
| I-176 | A |
| I-177 | A |
| I-178 | A |
| I-179 | B |
| I-180 | B |
| I-181 | B |
| I-182 | B |
| I-183 | B |
| I-184 | B |
| I-185 | A |
| I-186 | B |
| I-187 | A |
| I-188 | B |
| I-189 | A |
| I-190 | A |
| I-191 | A |

In addition to TC-71, several other cancer cell lines from diverse tissue origins, which have previously been demonstrated to be sensitive to IGF-1R inhibition, were shown to be sensitive to compounds (I). Examples include COLO 205, GEO (colorectal cancer) [3], LP-1 (multiple myeloma) [4] and HL-60 (acute myeloid leukemia) [5].

REFERENCE LIST

1 Manara, M. C., Landuzzi, L., Nanni, P., Nicoletti, G., Zambelli, D., Lollini, P. L., Nanni, C., Hofmann, F., Garcia-Echeverria, C., Picci, P. and Scotlandi, K. (2007) Preclinical in vivo study of new insulin-like growth factor-I receptor—specific inhibitor in Ewing's sarcoma. Clin. Cancer Res., 13, 1322-1330.

2 Pitts, T. M., Tan, A. C., Kulikowski, G. N., Tentler, J. J., Brown, A. M., Flanigan, S. A., Leong, S., Coldren, C. D., Hirsch, F. R., Varella-Garcia, M., Korch, C. and Eckhardt, S. G. (2010) Development of an integrated genomic classifier for a novel agent in colorectal cancer: approach to individualized therapy in early development. Clin Cancer Res., 16, 3193-3204.

3 Haluska, P., carboni, J. M., Loegering, D. A., Lee, F. Y., Wittman, M., Saulnier, M. G., Frennesson, D. B., Kalli, K. R., Conover, C. A., Attar, R. M., Kaufmann, S. H., Gottardis, M. and Erlichman, C. (2006) In vitro and in vivo antitumor effects of the dual insulin-like growth factor-I/insulin receptor inhibitor, BMS-554417. Cancer Res., 66, 362-371.

4 Georgii-Hemming, P., Wiklund, H. J., Ljunggren, O. and Nilsson, K. (1996) Insulin-like growth factor I is a growth and survival factor in human multiple myeloma cell lines. Blood, 88, 2250-2258.

5 Wahner Hendrickson, A. E., Haluska, P., Schneider, P. A., Loegering, D. A., Peterson, K. L., Attar, R., Smith, B. D., Erlichman, C., Gottardis, M., Karp, J. E., carboni, J. M. and Kaufmann, S. H. (2009) Expression of insulin receptor isoform A and insulin-like growth factor-1 receptor in human acute myelogenous leukemia: effect of the dual-receptor inhibitor BMS-536924 in vitro. Cancer Res., 69, 7635-7643.

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto:

brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma, hormone receptor positive breast cancer (estrogen receptor positive breast cancer, progesterone receptor positive breast cancer), Her2 positive breast cancer, triple negative breast cancer; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); tubuline inhibitors; PARP inhibitors, topoisomerase inhibitors (e.g. epipodophyllotoxins such as for example etoposide and etopophos, teniposide, amsacrin, topotecan, irinotecan, mitoxantron), serine/threonine kinase inhibitors (e.g. PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP, Mcl-1, MDM2/MDMX), MEK inhibitors, ERK inhibitors, IGF-1R inhibitors, ErbB receptor inhibitors, rapamycin analogs (e.g. everolimus, temsirolimus, ridaforolimus, sirolimus) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxyadenosine, 2-fluorodesoxy-cytidine, 2-methoxyoestradiol, 2C4, 3-alethine, 131-I-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEX$^{GM-CSF}$, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PDO325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhuMAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat and zosuquidar.

IGF-1R/IR inhibitors potentially influence blood glucose level as a side effect (e.g. hyperglycemia, see WO 2005/034868). Thus, it is one aspect of the invention to use an IGF-1R/IR inhibitor (I) in combination with an anti-diabetic drug, e.g. an insulin-sensitizer such as metformin.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (I) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of the formula (I)

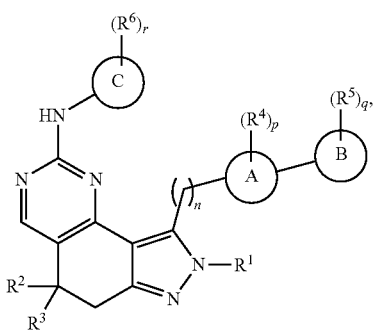

wherein
$R^1$ denotes $C_{1-4}$alkyl;
$R^2$ denotes hydrogen or $C_{1-4}$alkyl;
$R^3$ denotes hydrogen or $C_{1-4}$alkyl;
n denotes 0 or 1;
ring A is phenyl or 5-6 membered heteroaryl;
each $R^4$ is independently of one another selected from among halogen, $C_{1-4}$alkoxy, $C_{1-4}$alkyl and —CN;
p denotes 0, 1 or 2;
ring B is a 5-membered heteroaryl;
each $R^5$ independently is $R^{b1}$ or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, $S(O)_2NR^{c1}R^{c1}$, —$NHC(O)R^{c1}$ and —$N(C_{1-4}alkyl)C(O)R^{c1}$;
each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{d1}$ is independently selected from among —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$ and —$N(C_{1-4}alkyl)C(O)R^{e1}$;
each $R^{e1}$ independently of one another denotes hydrogen or a group, optionally substituted by one or more, identical or different $R^{f1}$ and/or $R^{g1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{f1}$ is independently selected from among —$OR^{g1}$, —$NR^{g1}R^{g1}$, halogen, —CN, —$C(O)R^{g1}$, —$C(O)OR^{g1}$, —$C(O)NR^{g1}R^{g1}$, —$S(O)_2R^{g1}$, —$S(O)_2NR^{g1}R^{g1}$, —$NHC(O)R^{g1}$ and —$N(C_{1-4}alkyl)C(O)R^{g1}$;
each $R^{g1}$ independently of one another denotes hydrogen or $C_{1-6}$alkyl;
q denotes 0, 1 or 2;
ring C is phenyl or 5-6 membered heteroaryl;
each $R^6$ independently is $R^{b2}$ or a group, optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;
each $R^{e2}$ independently of one another denotes hydrogen or a group, optionally substituted by one or more, identical or different $R^{f2}$ and/or $R^{g2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;
each $R^{g2}$ independently of one another denotes hydrogen or $C_{1-6}$alkyl;
r denotes 0, 1 or 2;
or a tautomer or salt thereof.
2. A compound according to claim 1, wherein
ring C is phenyl;
each $R^6$ independently is $R^{b2}$ or a group, optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;
each $R^{e2}$ independently of one another denotes hydrogen or a group, optionally substituted by one or more, identical or different $R^{f2}$ and/or $R^{g2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;
each $R^{g2}$ independently of one another denotes hydrogen or $C_{1-6}$alkyl;
r denotes 0, 1 or 2.

3. A compound according to claim 1, wherein
ring C is phenyl;
each $R^6$ independently is $R^{b2}$ or a group, optionally substituted by one or more, identical or different $R^{b2}$ and/or $R^{c2}$, selected from among $C_{1-6}$alkyl, $C_{3-6}$cycloalkyl, phenyl, 5-6 membered heteroaryl and 3-7 membered heterocyclyl;
  each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
  each $R^{c2}$ independently of one another denotes hydrogen or a group, optionally substituted by one or more, identical or different $R^{d2}$ and/or $R^{e2}$, selected from among $C_{1-6}$alkyl, $C_{3-6}$cycloalkyl, phenyl, 5-6 membered heteroaryl and 3-7 membered heterocyclyl;
  each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;
  each $R^{e2}$ independently of one another denotes hydrogen or a group, optionally substituted by one or more, identical or different $R^{f2}$ and/or $R^{g2}$, selected from among $C_{1-6}$alkyl, $C_{3-6}$cycloalkyl, phenyl, 5-6 membered heteroaryl and 3-7 membered heterocyclyl;
  each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;
  each $R^{g2}$ independently of one another denotes hydrogen or $C_{1-6}$alkyl;
r denotes 0, 1 or 2.

4. A compound according to claim 1, wherein
ring C is phenyl;
each $R^6$ independently is $R^{b2}$ or 3-7 membered heterocyclyl, the heterocyclyl optionally substituted by one or more, identical or different $R^{b2}$ and/or $R^{c2}$;
  each $R^{b2}$ is independently selected from among —$OR^{c2}$, —$C(O)R^{c2}$, —$C(O)OR^{c2}$, —$C(O)NR^{c2}R^{c2}$ and —$S(O)_2NR^{c2}R^{c2}$;
  each $R^{c2}$ independently of one another denotes hydrogen or a group, optionally substituted by one or more, identical or different $R^{d2}$ and/or $R^{e2}$, selected from among $C_{1-6}$alkyl and 3-7 membered heterocyclyl;
  each $R^{d2}$ is independently selected from among —$OR^{e2}$ and —$NR^{e2}R^{e2}$;
  each $R^{e2}$ independently of one another denotes hydrogen or a group, optionally substituted by one or more, identical or different $R^{f2}$ and/or $R^{g2}$, selected from among $C_{1-6}$alkyl and 3-7 membered heterocyclyl;
  each $R^{f2}$ is —$OR^{g2}$;
  each $R^{g2}$ independently of one another denotes hydrogen or $C_{1-6}$alkyl;
r denotes 0, 1 or 2.

5. A compound according to claim 1, wherein
ring C is phenyl;
each $R^6$ independently is —$C(O)NR^{c2}R^{c2}$, —$C(O)R^{c2}$ or —$OR^{c2}$;
  each $R^{c2}$ independently of one another denotes hydrogen or a group, optionally substituted by one or more, identical or different $R^{d2}$ and/or $R^{e2}$, selected from among $C_{1-6}$alkyl and 3-7 membered heterocyclyl;
  each $R^{d2}$ is independently selected from among —$OR^{e2}$ and —$NR^{e2}R^{e2}$;
  each $R^{e2}$ independently of one another denotes hydrogen or a group, optionally substituted by one or more, identical or different $R^{f2}$ and/or $R^{g2}$, selected from among $C_{1-6}$alkyl and 3-7 membered heterocyclyl;
  each $R^{f2}$ is —$OR^{g2}$;
  each $R^{g2}$ independently of one another denotes hydrogen or $C_{1-6}$alkyl;
r denotes 0, 1 or 2.

6. A compound according to claim 1, wherein
r is 2.

7. A compound according to claim 1, wherein
ring C is 5-6 membered heteroaryl;
each $R^6$ independently is $R^{b2}$ or a group, optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
  each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
  each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
  each $R^{d2}$ is independently selected from among —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$ and —$N(C_{1-4}alkyl)C(O)R^{e2}$;
  each $R^{e2}$ independently of one another denotes hydrogen or a group, optionally substituted by one or more, identical or different $R^{f2}$ and/or $R^{g2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
  each $R^{f2}$ is independently selected from among —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$ and —$N(C_{1-4}alkyl)C(O)R^{g2}$;
  each $R^{g2}$ independently of one another denotes hydrogen or $C_{1-6}$alkyl;
r denotes 0, 1 or 2.

8. A compound according to claim 7, wherein
ring C is 5-6 membered heteroaryl;
each $R^6$ independently is $R^{b2}$ or a group, optionally substituted by one or more, identical or different $R^{b2}$ and/or $R^{c2}$, selected from among $C_{1-6}$alkyl, $C_{3-6}$cycloalkyl, phenyl, 5-6 membered heteroaryl and 3-7 membered heterocyclyl;
each $R^{b2}$ is independently selected from among —$OR^{c2}$, —$NR^{c2}R^{c2}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$ and —$N(C_{1-4}alkyl)C(O)R^{c2}$;
  each $R^{c2}$ independently of one another denotes hydrogen or a group, optionally substituted by one or more, identical or different $R^{d2}$ and/or $R^{e2}$, selected from among $C_{1-6}$alkyl, $C_{3-6}$cycloalkyl, phenyl, 5-6 membered heteroaryl and 3-7 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2$N$R^{e2}R^{e2}$, —NHC(O)$R^{e2}$ and —N(C$_{1-4}$alkyl)C(O)$R^{e2}$;

each $R^{e2}$ independently of one another denotes hydrogen or a group, optionally substituted by one or more, identical or different $R^{f2}$ and/or $R^{g2}$, selected from among C$_{1-6}$alkyl, C$_{3-6}$cycloalkyl, phenyl, 5-6 membered heteroaryl and 3-7 membered heterocyclyl;

each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2$N$R^{g2}R^{g2}$, —NHC(O)$R^{g2}$ and —N(C$_{1-4}$alkyl)C(O)$R^{g2}$;

each $R^{g2}$ independently of one another denotes hydrogen or C$_{1-6}$alkyl;

r denotes 0, 1 or 2.

9. A compound according to claim 8, wherein
ring C is pyrazolyl;
each $R^6$ independently is $R^{b2}$ or a group, optionally substituted by one or more, identical or different $R^{b2}$ and/or $R^{c2}$, selected from among C$_{1-6}$alkyl, C$_{3-6}$cycloalkyl, phenyl, 5-6 membered heteroaryl and 3-7 membered heterocyclyl;
each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$ and —N(C$_{1-4}$alkyl)C(O)$R^{c2}$;
each $R^{c2}$ independently of one another denotes hydrogen or a group, optionally substituted by one or more, identical or different $R^{d2}$ and/or $R^{e2}$, selected from among C$_{1-6}$alkyl, C$_{3-6}$cycloalkyl, phenyl, 5-6 membered heteroaryl and 3-7 membered heterocyclyl;
each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2$N$R^{e2}R^{e2}$, —NHC(O)$R^{e2}$ and —N(C$_{1-4}$alkyl)C(O)$R^{e2}$;
each $R^{e2}$ independently of one another denotes hydrogen or a group, optionally substituted by one or more, identical or different $R^{f2}$ and/or $R^{g2}$, selected from among C$_{1-6}$alkyl, C$_{3-6}$cycloalkyl, phenyl, 5-6 membered heteroaryl and 3-7 membered heterocyclyl;
each $R^{f2}$ is independently selected from among —$OR^{g2}$, —$NR^{g2}R^{g2}$, halogen, —CN, —C(O)$R^{g2}$, —C(O)O$R^{g2}$, —C(O)N$R^{g2}R^{g2}$, —S(O)$_2R^{g2}$, —S(O)$_2$N$R^{g2}R^{g2}$, —NHC(O)$R^{g2}$ and —N(C$_{1-4}$alkyl)C(O)$R^{g2}$;
each $R^{g2}$ independently of one another denotes hydrogen or C$_{1-6}$alkyl;

r denotes 0, 1 or 2.

10. A compound according to claim 9, wherein
ring C is pyrazolyl;
each $R^6$ independently is a group, optionally substituted by one or more, identical or different $R^{b2}$ and/or $R^{c2}$, selected from among C$_{1-6}$alkyl and 3-7 membered heterocyclyl;
each $R^{b2}$ is independently selected from among —$OR^{c2}$, —$NR^{c2}R^{c2}$, —C(O)$R^{c2}$, —C(O)O$R^{c2}$, —C(O)N$R^{c2}R^{c2}$, S(O)$_2R^{c2}$ and —S(O)$_2$N$R^{c2}R^{c2}$;
each $R^{c2}$ independently of one another denotes hydrogen or a group, optionally substituted by one or more, identical or different $R^{d2}$ and/or $R^{e2}$, selected from among C$_{1-6}$alkyl, 5-6 membered heteroaryl and 3-7 membered heterocyclyl;
each $R^{d2}$ is independently selected from among —$OR^{e2}$ and —$NR^{e2}R^{e2}$;

each $R^{e2}$ independently of one another denotes hydrogen or C$_{1-6}$alkyl optionally substituted by one or more, identical or different $R^{f2}$ and/or $R^{g2}$;
each $R^{f2}$ is —$OR^{g2}$;
each $R^{g2}$ independently of one another denotes hydrogen or C$_{1-6}$alkyl;

r denotes 0, 1 or 2.

11. A compound according to claim 10, wherein
r is 1.

12. A compound according to claim 10, wherein
r is 1 and ring C and $R^6$ altogether is

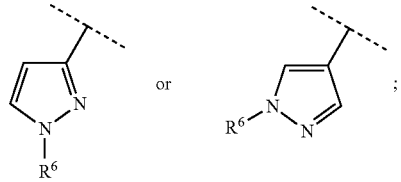

$R^6$ independently is a group, optionally substituted by one or more, identical or different $R^{b2}$ and/or $R^{c2}$, selected from among C$_{1-6}$alkyl and 3-7 membered heterocyclyl;
each $R^{b2}$ is independently selected from among —$OR^{c2}$, —$NR^{c2}R^{c2}$, —C(O)$R^{c2}$, —C(O)O$R^{c2}$, —C(O)N$R^{c2}R^{c2}$, —S(O)$_2R^{c2}$ and —S(O)$_2$N$R^{c2}R^{c2}$;
each $R^{c2}$ independently of one another denotes hydrogen or a group, optionally substituted by one or more, identical or different $R^{d2}$ and/or $R^{e2}$, selected from among C$_{1-6}$alkyl, 5-6 membered heteroaryl and 3-7 membered heterocyclyl;
each $R^{d2}$ is independently selected from among —$OR^{e2}$ and —$NR^{e2}R^{e2}$;
each $R^{e2}$ independently of one another denotes hydrogen or C$_{1-6}$alkyl optionally substituted by one or more, identical or different $R^{f2}$ and/or $R^{g2}$;
each $R^{f2}$ is —$OR^{g2}$;
each $R^{g2}$ independently of one another denotes hydrogen or C$_{1-6}$alkyl.

13. A compound according to claim 12, wherein
r is 1 and ring C and $R^6$ altogether is

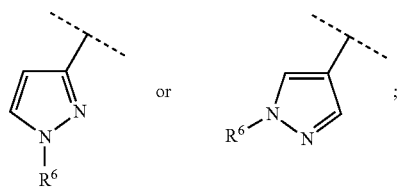

$R^6$ independently is selected from among C$_{1-4}$alkyl, hydroxy-C$_{2-4}$alkyl, C$_{1-4}$alkoxy-C$_{2-4}$alkyl and (C$_{1-4}$alkyl)$_2$N—C$_{2-4}$alkyl.

14. A compound according to claim 12, wherein
r is 1 and ring C and $R^6$ altogether is selected from among

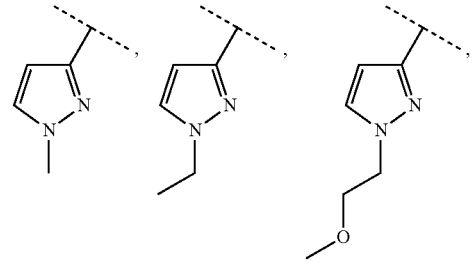

-continued

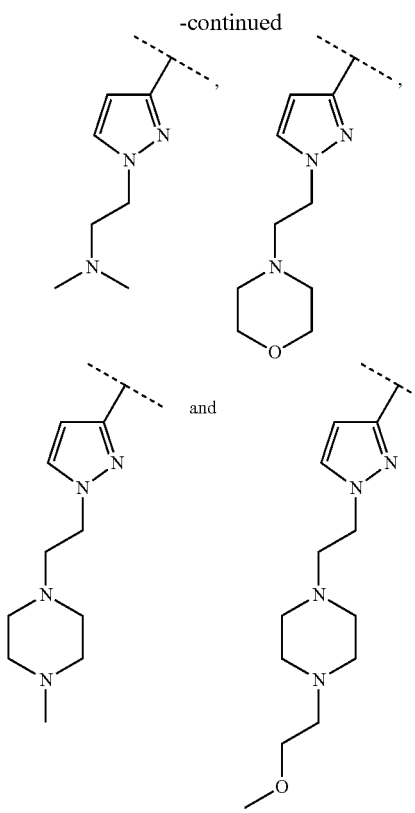

15. A compound according to claim 1, wherein
ring B is a 5-membered heteroaryl;
each $R^5$ independently is $R^{b1}$ or a group, optionally substituted by one or more, identical or different $R^{b1}$ and/or $R^{c1}$, selected from among $C_{1-6}$alkyl, $C_{3-6}$cycloalkyl, phenyl, 5-6 membered heteroaryl and 3-7 membered heterocyclyl;
  each $R^{b1}$ is independently selected from among —$OR^{c1}$, —$NR^{c1}R^{c1}$, halogen, —CN, —C(O)$R^{c1}$, —C(O)OR$^{c1}$, —C(O)NR$^{c1}R^{c1}$, —S(O)$_2R^{c1}$, —S(O)$_2$NR$^{c1}R^{c1}$, —NHC(O)R$^{c1}$ and —N(C$_{1-4}$alkyl)C(O)R$^{c1}$;
  each $R^{c1}$ independently of one another denotes hydrogen or a group, optionally substituted by one or more, identical or different $R^{d1}$ and/or $R^{e1}$, selected from among $C_{1-6}$alkyl, $C_{3-6}$cycloalkyl, phenyl, 5-6 membered heteroaryl and 3-7 membered heterocyclyl;
  each $R^{d1}$ is independently selected from among —$OR^{e1}$, —$NR^{e1}R^{e1}$, halogen, —CN, —C(O)$R^{e1}$, —C(O)OR$^{e1}$, —C(O)NR$^{e1}R^{e1}$, —S(O)$_2R^{e1}$, —S(O)$_2$NR$^{e1}R^{e1}$, —NHC(O)R$^{e1}$ and —N(C$_{1-4}$alkyl)C(O)R$^{e1}$;
  each $R^{e1}$ independently of one another denotes hydrogen or a group, optionally substituted by one or more, identical or different $R^{f1}$ and/or $R^{g1}$, selected from among $C_{1-6}$alkyl, $C_{3-6}$cycloalkyl, phenyl, 5-6 membered heteroaryl and 3-7 membered heterocyclyl;
  each $R^{f1}$ is independently selected from among —$OR^{g1}$, —$NR^{g1}R^{g1}$, halogen, —CN, —C(O)$R^{g1}$, —C(O)OR$^{g1}$, —C(O)NR$^{g1}R^{g1}$, —S(O)$_2R^{g1}$, —S(O)$_2$NR$^{g1}R^{g1}$, —NHC(O)R$^{g1}$ and —N(C$_{1-4}$alkyl)C(O)R$^{g1}$;
  each $R^{g1}$ independently of one another denotes hydrogen or $C_{1-6}$alkyl;
q denotes 0, 1 or 2.

16. A compound according to claim 15, wherein
ring B is pyrazolyl;
each $R^5$ independently is $R^{b1}$ or a group, optionally substituted by one or more, identical or different $R^{b1}$ and/or $R^{c1}$, selected from among $C_{1-6}$alkyl, $C_{3-6}$cycloalkyl, phenyl, 5-6 membered heteroaryl and 3-7 membered heterocyclyl;
  each $R^{b1}$ is independently selected from among —$OR^{c1}$, —$NR^{c1}R^{c1}$, halogen, —CN, —C(O)$R^{c1}$, —C(O)OR$^{c1}$, —C(O)NR$^{c1}R^{c1}$, —S(O)$_2R^{c1}$, —S(O)$_2$NR$^{c1}R^{c1}$, —NHC(O)R$^{c1}$ and —N(C$_{1-4}$alkyl)C(O)R$^{c1}$;
  each $R^{c1}$ independently of one another denotes hydrogen or a group, optionally substituted by one or more, identical or different $R^{d1}$ and/or $R^{e1}$, selected from among $C_{1-6}$alkyl, $C_{3-6}$cycloalkyl, phenyl, 5-6 membered heteroaryl and 3-7 membered heterocyclyl;
  each $R^{d1}$ is independently selected from among —$OR^{e1}$, —$NR^{e1}R^{e1}$, halogen, —CN, —C(O)$R^{e1}$, —C(O)OR$^{e1}$, —C(O)NR$^{e1}R^{e1}$, —S(O)$_2R^{e1}$, —S(O)$_2$NR$^{e1}R^{e1}$, —NHC(O)R$^{e1}$ and —N(C$_{1-4}$alkyl)C(O)R$^{e1}$;
  each $R^{e1}$ independently of one another denotes hydrogen or a group, optionally substituted by one or more, identical or different $R^{f1}$ and/or $R^{g1}$, selected from among $C_{1-6}$alkyl, $C_{3-6}$cycloalkyl, phenyl, 5-6 membered heteroaryl and 3-7 membered heterocyclyl;
  each $R^{f1}$ is independently selected from among —$OR^{g1}$, —$NR^{g1}R^{g1}$, halogen, —CN, —C(O)$R^{g1}$, —C(O)OR$^{g1}$, —C(O)NR$^{g1}R^{g1}$, —S(O)$_2R^{g1}$, —S(O)$_2$NR$^{g1}R^{g1}$, —NHC(O)R$^{g1}$ and —N(C$_{1-4}$alkyl)C(O)R$^{g1}$;
  each $R^{g1}$ independently of one another denotes hydrogen or $C_{1-6}$alkyl;
q denotes 0, 1 or 2.

17. A compound according to claim 16, wherein
ring B is pyrazolyl;
each $R^5$ independently is a group, optionally substituted by one or more, identical or different $R^{b1}$ and/or $R^{c1}$, selected from among $C_{1-6}$alkyl and 3-7 membered heterocyclyl;
  each $R^{b1}$ is independently selected from among —$OR^{c1}$, —$NR^{c1}R^{c1}$, halogen, —C(O)OR$^{c1}$ and —C(O)NR$^{c1}R^{c1}$;
  each $R^{c1}$ independently of one another denotes hydrogen or a group, optionally substituted by one or more, identical or different $R^{d1}$ and/or $R^{e1}$, selected from among $C_{1-6}$alkyl, phenyl and 3-7 membered heterocyclyl;
  each $R^{d1}$ is independently selected from among —$OR^{e1}$ and —$NR^{e1}R^{e1}$;
  each $R^{e1}$ independently of one another denotes hydrogen or $C_{1-6}$alkyl optionally substituted by one or more, identical or different $R^{f1}$ and/or $R^{g1}$;
  each $R^{f1}$ is —$OR^{g1}$;
  each $R^{g1}$ independently of one another denotes hydrogen or $C_{1-6}$alkyl;
q denotes 0, 1 or 2.

18. A compound according to claim 17, wherein
q is 1.

19. A compound according to claim 17, wherein
q is 1 and ring B and $R^5$ altogether is

225

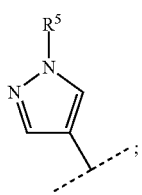

R⁵ is a group, optionally substituted by one or more, identical or different $R^{b1}$ and/or $R^{c1}$, selected from among $C_{1-6}$alkyl and 3-7 membered heterocyclyl;

each $R^{b1}$ is independently selected from among —$OR^{c1}$, —$NR^{c1}R^{c1}$, halogen, —$C(O)OR^{c1}$ and —$C(O)NR^{c1}R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, phenyl and 3-7 membered heterocyclyl;

each $R^{d1}$ is independently selected from among —$OR^{e1}$ and —$NR^{e1}R^{e1}$;

each $R^{e1}$ independently of one another denotes hydrogen or $C_{1-6}$alkyl optionally substituted by one or more, identical or different $R^{f1}$ and/or $R^{g1}$;

each $R^{f1}$ is —$OR^{g1}$;

each $R^{g1}$ independently of one another denotes hydrogen or $C_{1-6}$alkyl.

20. A compound according to claim 19, wherein q is 1 and ring B and R⁵ altogether is

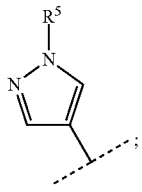

R⁵ independently is selected from among $C_{1-4}$alkyl, hydroxy-$C_{2-4}$alkyl, $C_{1-4}$alkoxy-$C_{2-4}$alkyl and ($C_{1-4}$alkyl)₂N—$C_{2-4}$alkyl.

21. A compound according to claim 19, wherein q is 1 and ring B and R⁵ altogether is selected from among

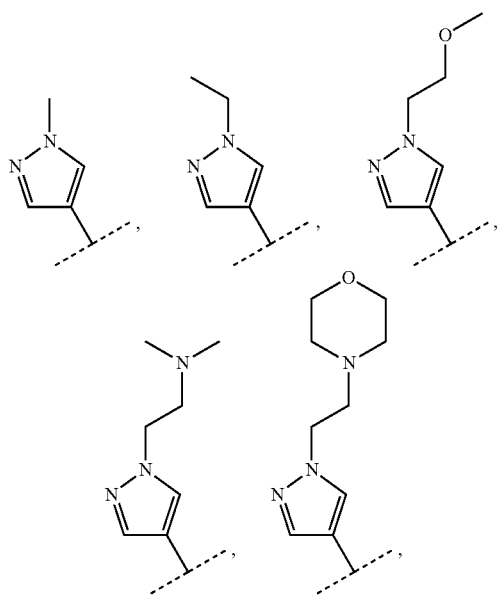

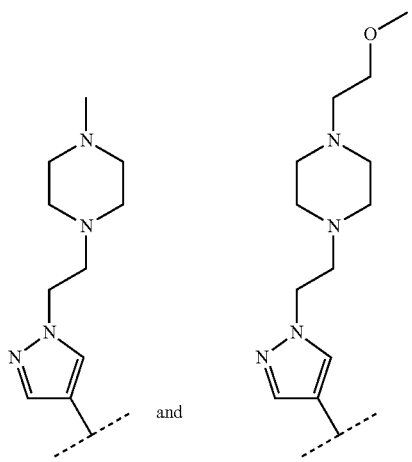
and

22. A compound according to claim 1, wherein R¹ is methyl.

23. A compound according to claim 1, wherein R² and R³ both denote hydrogen.

24. A compound according to claim 1, wherein R² is hydrogen and R³ is $C_{1-4}$alkyl.

25. A compound according to claim 1, wherein R² is hydrogen and R³ is methyl.

26. A compound according to claim 1, wherein ring A is phenyl or pyridyl;
each R⁴ is independently of one another selected from among halogen, $C_{1-4}$alkoxy, $C_{1-4}$alkyl and —CN;
p denotes 0, 1 or 2.

27. A compound according claim 26, wherein ring A is phenyl or pyridyl;
p is 0.

28. A compound according to claim 1 selected from the group consisting of

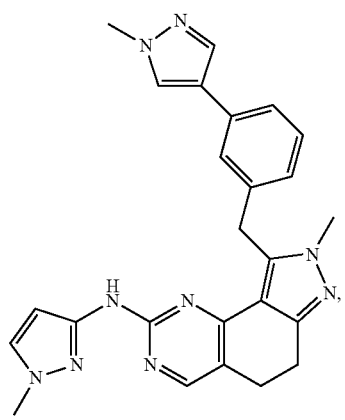

I-12

I-15
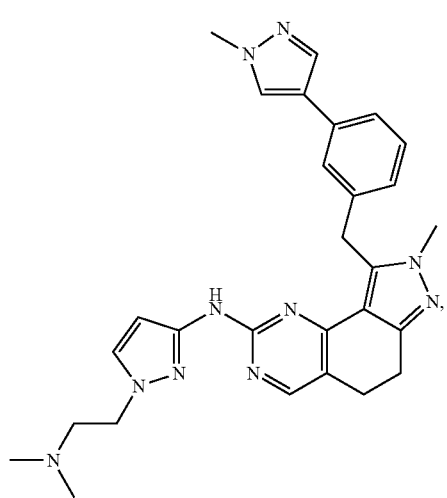
I-16
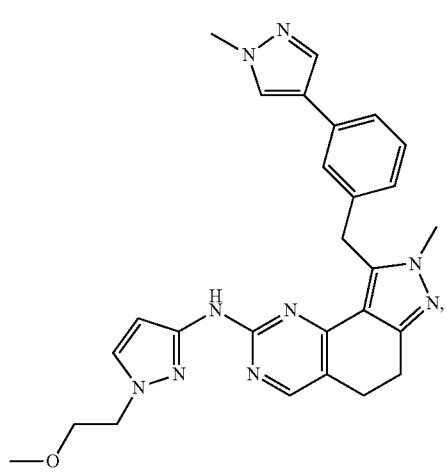
I-23
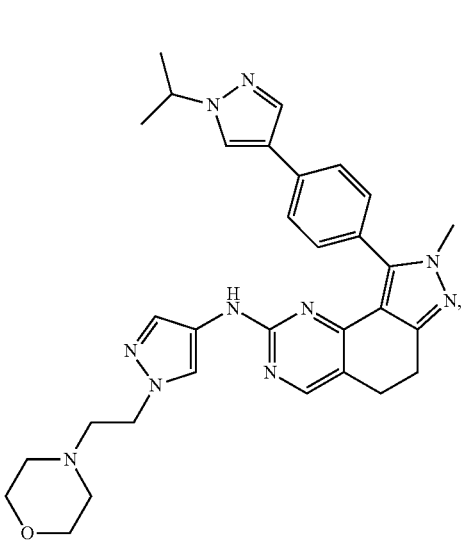
I-25
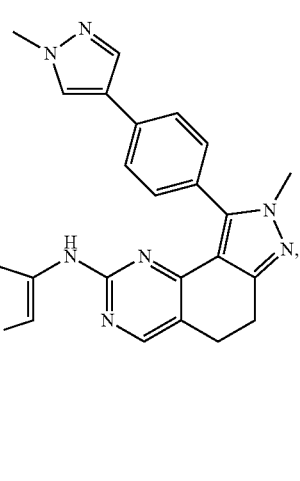
I-28
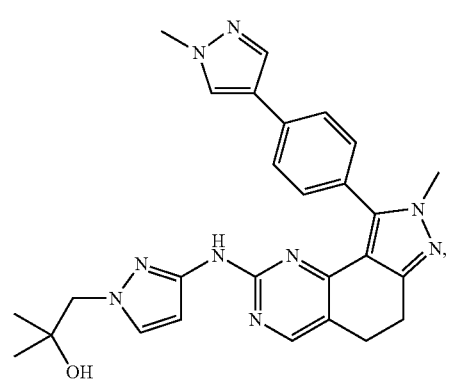
I-29
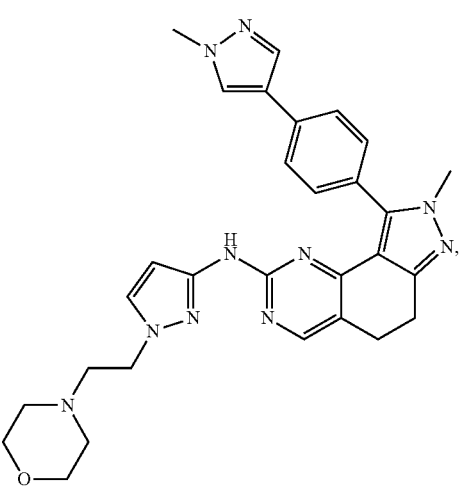

I-30
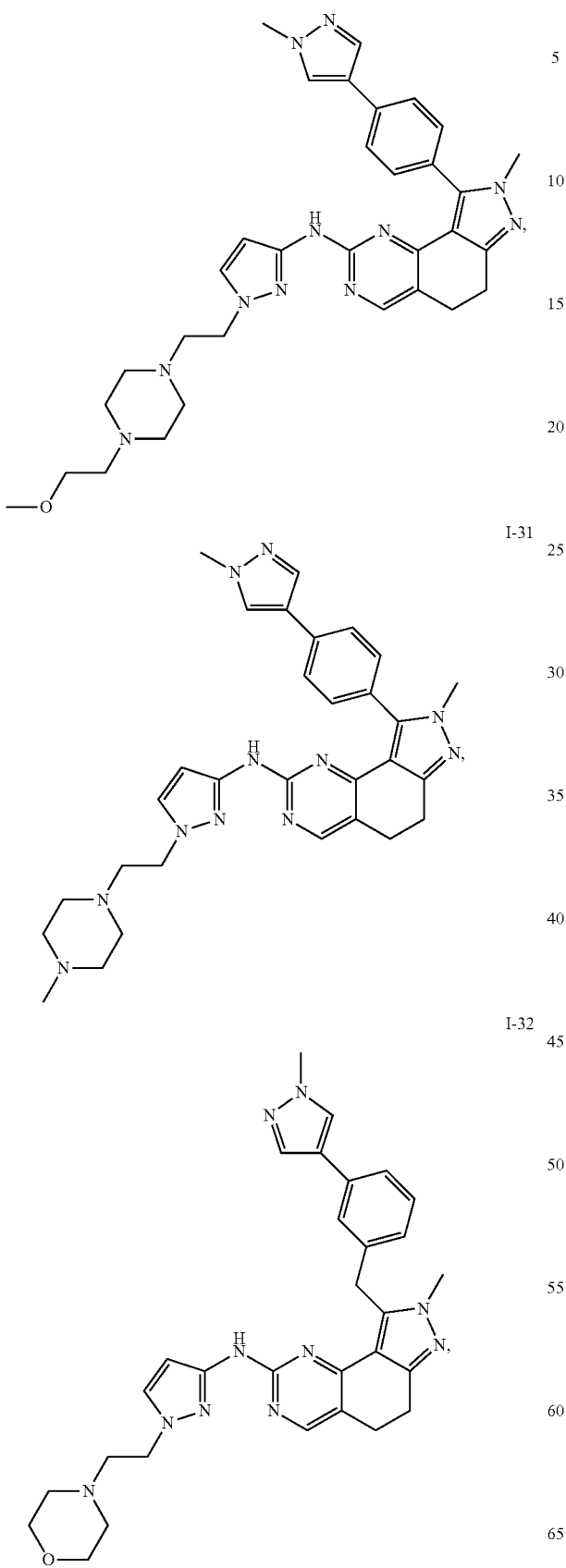
I-31
I-32
I-33
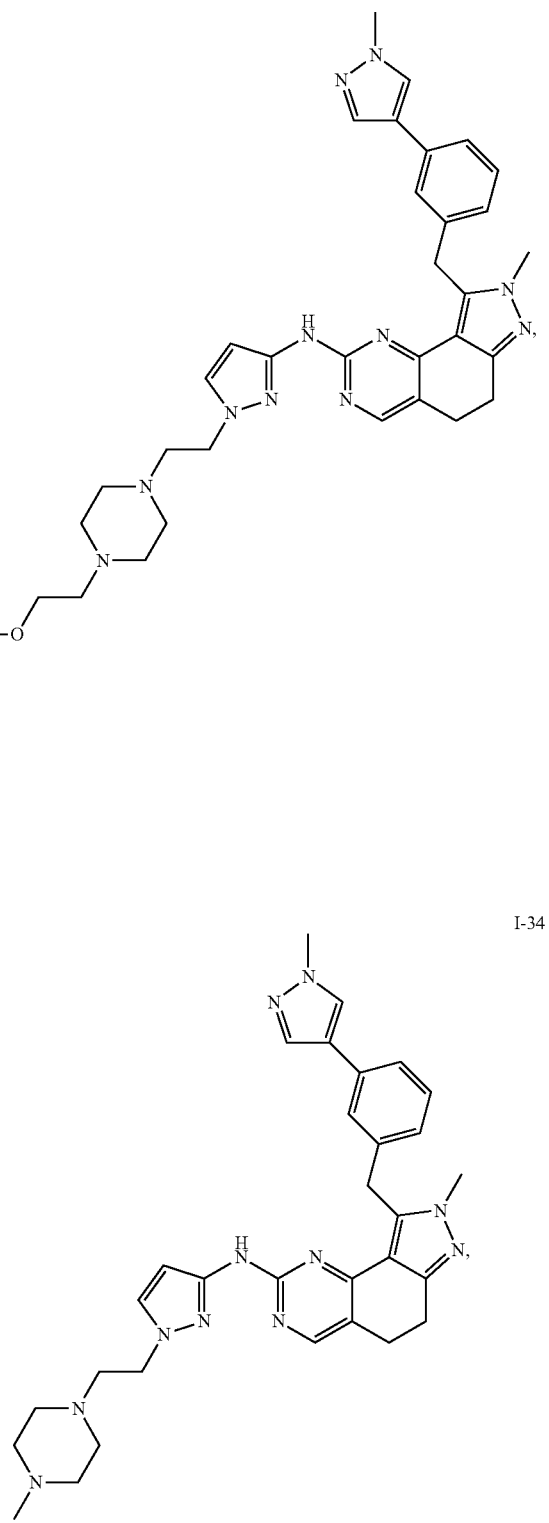
I-34

-continued
I-38
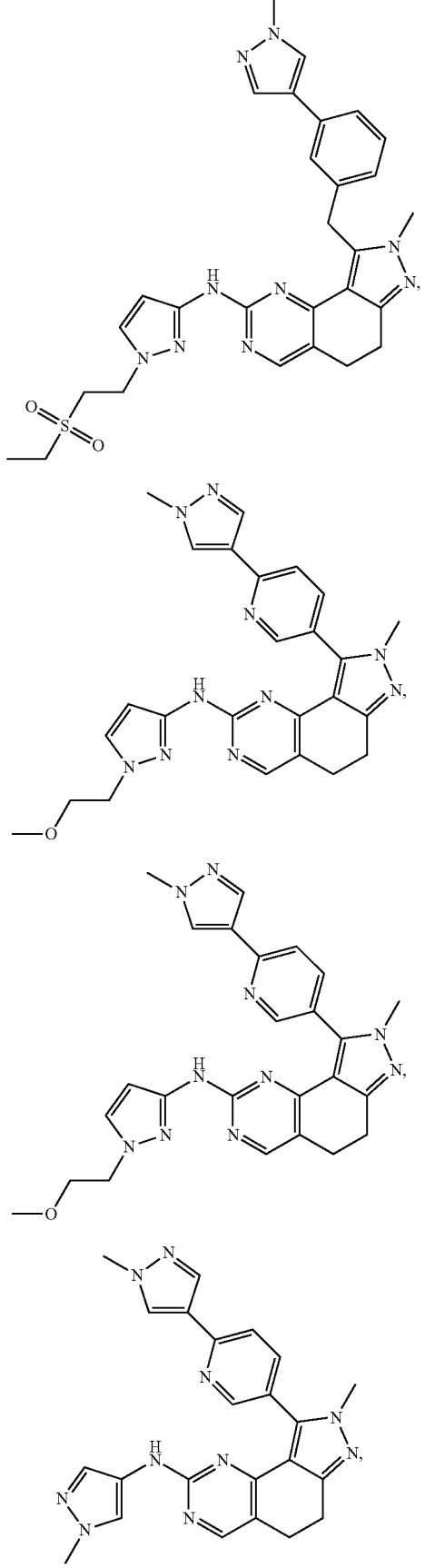
I-182
I-183
I-185
-continued
I-186
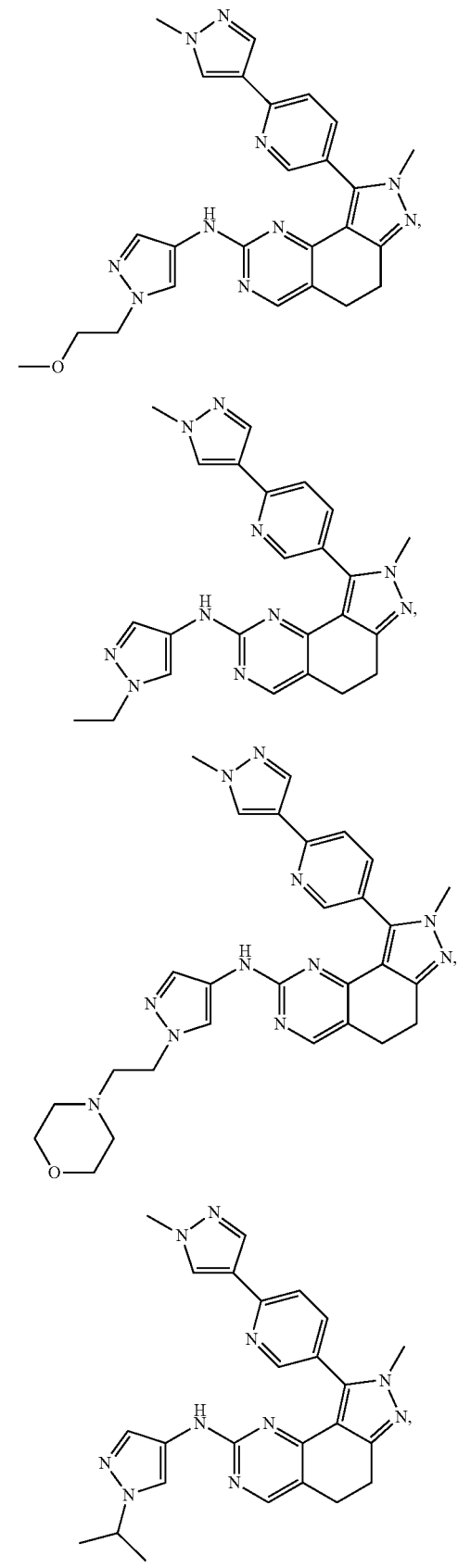
I-187
I-188
I-189

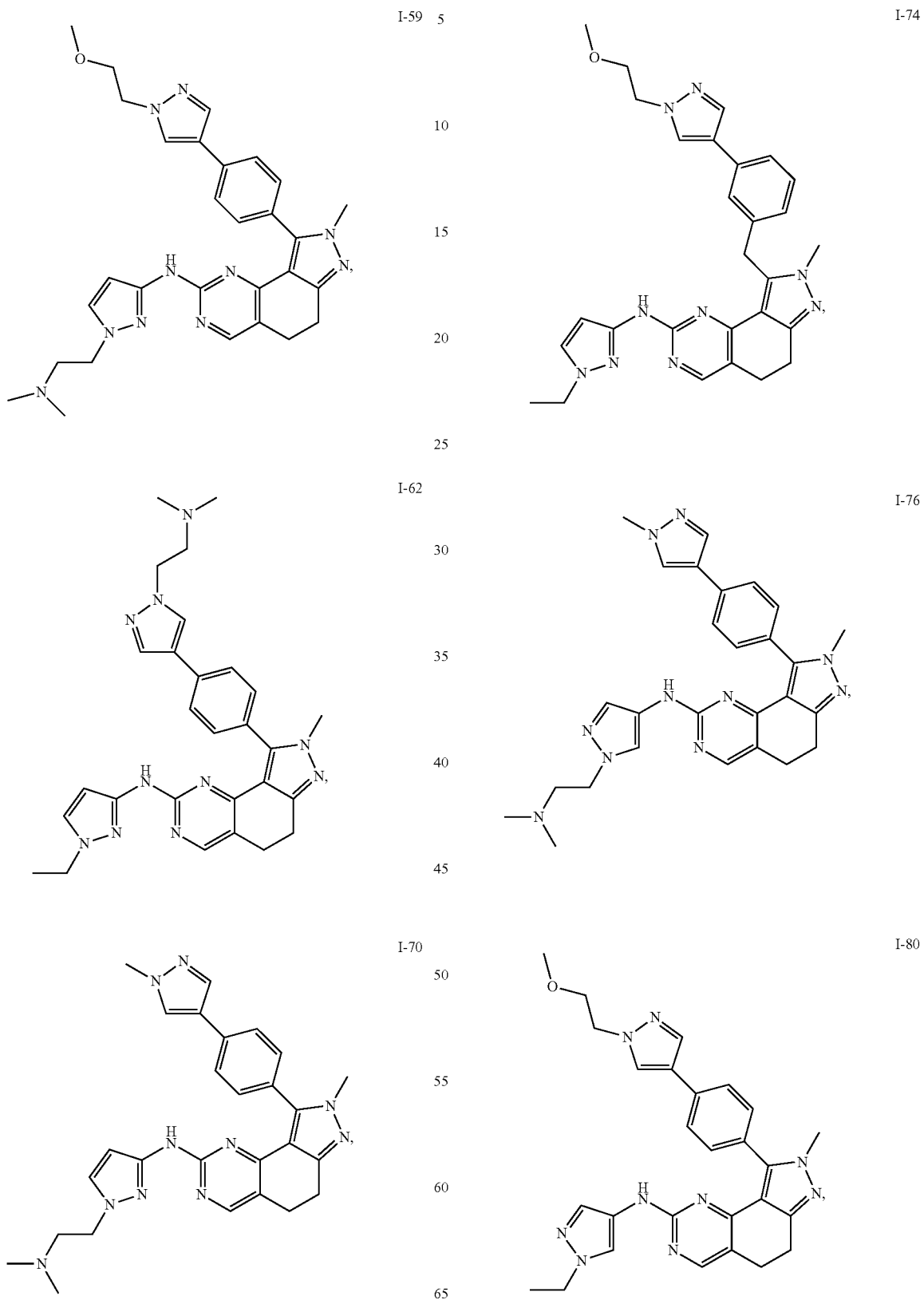

I-84
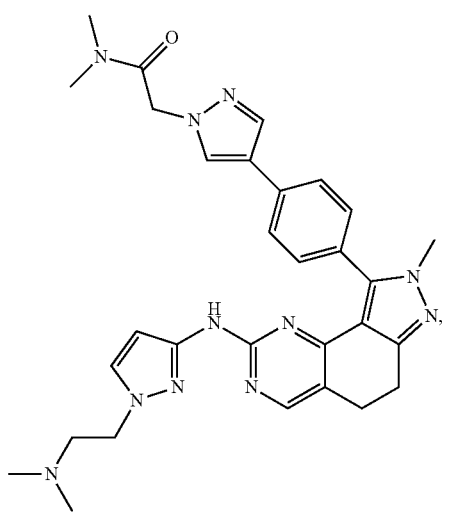
I-94
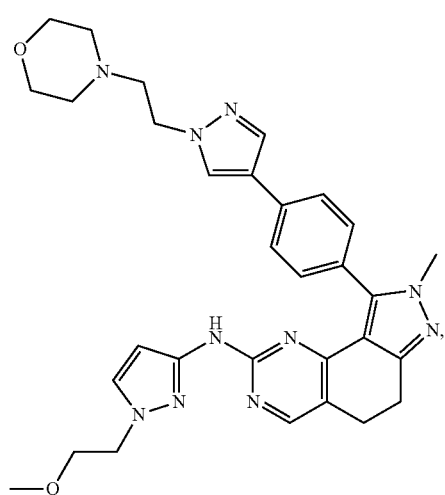
I-97
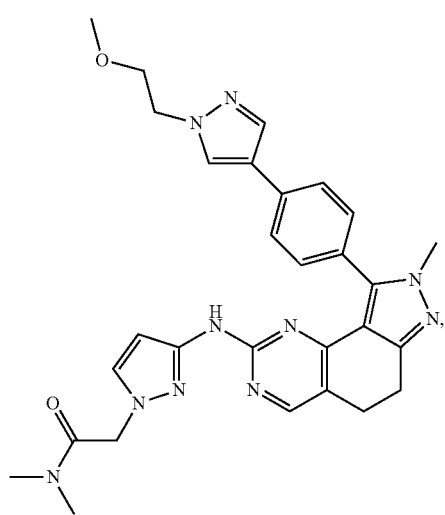
I-99
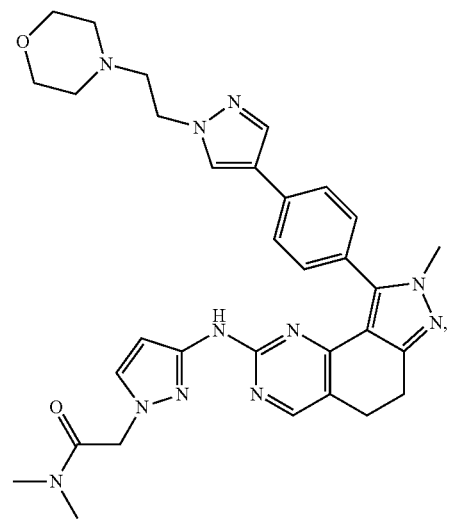
I-107
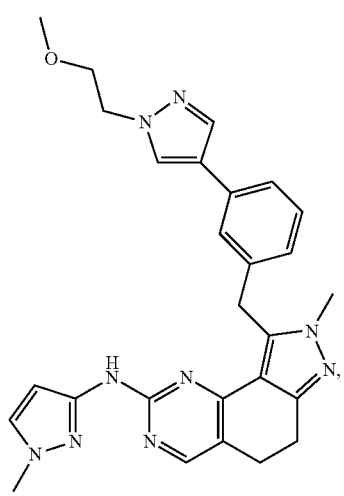
I-108
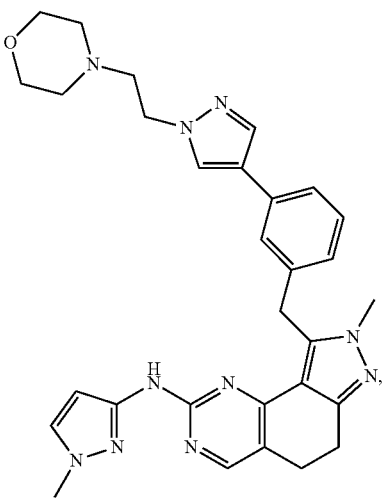

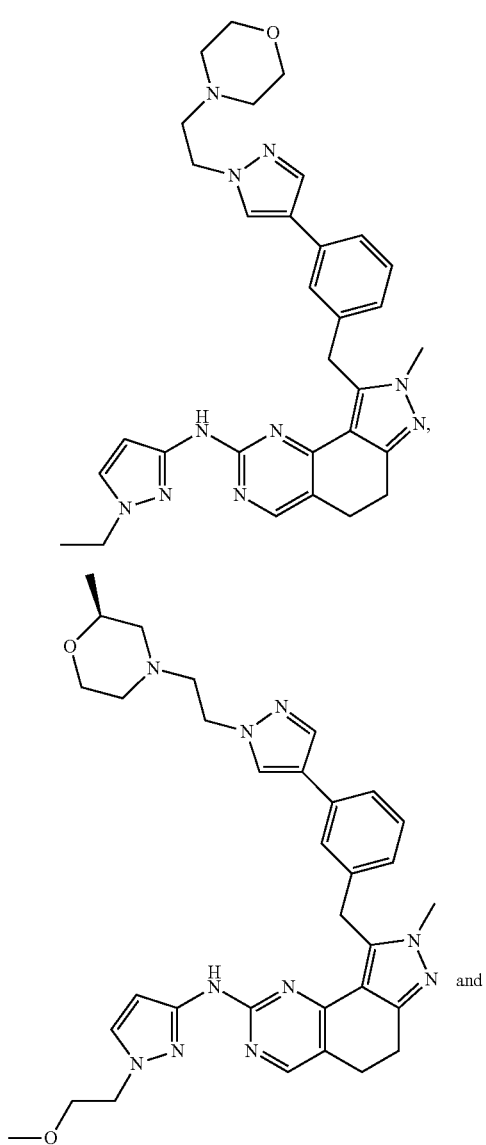
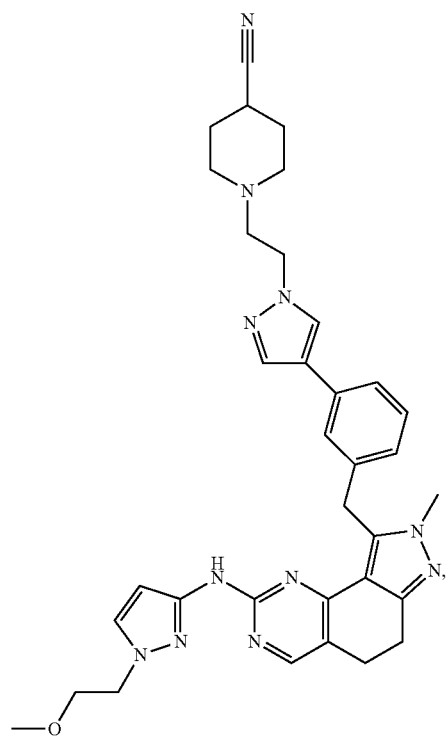
or a tautomer or salt thereof.
29. A pharmaceutically acceptable salt of a compound according to one of claim 1 to 28.
30. A pharmaceutical preparation containing as active substance a compound of formula (I) according to claim 1 or a pharmaceutically acceptable salt thereof and a pharmaceutically acceptable excipient or carrier.
* * * * *